(12) United States Patent
Rustgi et al.

(10) Patent No.: US 8,592,206 B2
(45) Date of Patent: Nov. 26, 2013

(54) CULTURE BASED SCREENING ASSAY AND METHODS OF USE THEREOF TO IDENTIFY AGENTS WHICH MODULATE TUMOR DEVELOPMENT, INVASION AND DIFFERENTIATION

(76) Inventors: Anil K. Rustgi, Villanova, PA (US); Carmen Z. Michaylira, King of Prussia, PA (US); Douglas B. Stairs, Philadelphia, PA (US)

(*) Notice: Subject to any disclaimer, the term of this patent is extended or adjusted under 35 U.S.C. 154(b) by 140 days.

(21) Appl. No.: 12/771,683

(22) Filed: Apr. 30, 2010

(65) Prior Publication Data
US 2011/0053185 A1    Mar. 3, 2011

Related U.S. Application Data

(63) Continuation-in-part of application No. PCT/US2008/081967, filed on Oct. 31, 2008.

(60) Provisional application No. 60/984,190, filed on Oct. 31, 2007.

(51) Int. Cl.
| | |
|---|---|
| C12N 5/00 | (2006.01) |
| C12N 5/07 | (2010.01) |
| C12N 5/10 | (2006.01) |
| C12N 15/00 | (2006.01) |
| C12N 15/09 | (2006.01) |
| C12N 15/113 | (2010.01) |

(52) U.S. Cl.
USPC ........... 435/325; 435/347; 435/373; 435/377; 435/455

(58) Field of Classification Search
USPC .......................... 435/325, 347, 373, 377, 455
See application file for complete search history.

(56) References Cited

U.S. PATENT DOCUMENTS

| | | | |
|---|---|---|---|
| 4,683,195 A | 7/1987 | Mullis et al. | |
| 4,800,195 A | 1/1989 | Burgess et al. | |
| 4,965,188 A | 10/1990 | Mullis et al. | |
| 2002/0068283 A1 | 6/2002 | Boeke et al. | |
| 2004/0175367 A1 | 9/2004 | Herlyn et al. | |
| 2005/0260748 A1 | 11/2005 | Chang et al. | |
| 2005/0272061 A1 | 12/2005 | Petroziello et al. | |
| 2006/0094038 A1 | 5/2006 | Wagner et al. | |
| 2008/0286269 A1* | 11/2008 | Violette et al. ............. | 424/133.1 |

FOREIGN PATENT DOCUMENTS

WO    WO 2007/125288    * 11/2007 ............... C12N 5/00

OTHER PUBLICATIONS

Dawson et al, Burns 22(2):93-100, 1996.*
Turner et al, J. Invest. Dermatol. 109:619-625, 1997.*
Ji et al, Oral Oncology 37:386-392, 2001.*
Palanca-Wessels et al, Carcinogenesis 24(7):1183-1190, 2003.*
Zagorowicz et al, Postgrad. Med. J. 83:529-535, 2007.*
Chung et al, Annals Surg. Onc. 14(11):3260-3267, 2007; available online Jul. 24, 2007.*
Shibata et al, Am. J. Pathol. 164(6):2269-2278, 2004.*
Lanza, 'Handbook of Stem Cells, vol. 2: Adult and Fetal Stem Cells', Elsevier Academic Press, 2004; p. 69 only.*
Nelson and Sun, J. Cell Biol. 97:244-251, 1983.*
Graham et al, Cancer Res. 45:2201-2205, 1985.*
Bellovin et al, Cancer Res. 65(23):10938-10945, 2005.*
Bendardaf et al, Anticancer Res. 24:2519-2530, 2004.*
Macpherson et al, Oncogene 26:5214-5228, 2007.*
Merlino et al, Science 224(4647):417-419, 1984; abstract only.*
Yan, W., et al. "Transduction of a mesenchyme-specific gene periostin into 293T cells induces cell invasive activity through epithelial-mesenchymal transformation." J Biol Chem. Jul. 14, 2006;281(28):19700-8. Epub May 15, 2006.
NCBI "Working List: Human OncoChip Genes" Jun. 4, 1999 [online]. [Retrieved on Feb. 17, 2009]. Retrieved from the Internet: <URL: http://nciarray.nci.nih.gov/gi_acc_ug_title.shtml (pdf pp. 1-16. p. 4 and 9).
Dickson, M.A., et al. "Human keratinocytes that express hTERT and also bypass a p16(INK4a)-enforced mechanism that limits life span become immortal yet retain normal growth and differentiation characteristics." Mol Cell Biol. Feb. 2000;20(4):1436-47.
Steinle, J.J., et al. "Eph B4 receptor signaling mediates endothelial cell migration and proliferation via the phosphatidylinositol 3-kinase pathway." J Biol Chem. Nov. 15, 2002;277(46):43830-5. Epub Sep. 13, 2002.
Lacroix, M., et al. "A low-density DNA microarray for analysis of markers in breast cancer." Int J Biol Markers. Jan.-Mar. 2002;17(1):5-23.
Enzinger, et al. "Esophageal cancer." N. Engl. J. Med. 2003;349:2241-52.
Mandard et al. "Genetic steps in the development of squamous cell carcinoma of the esophagus." Mutat. Res. 2000;462: 335-342.
Metzger et al. "Molecular biology of esophageal cancer." Onkologie 2004;27: 200-206.
Sunpaweravong et al. "Epidermal growth factor receptor and cyclin D1 are independently amplified and overexpressed in esophageal squamous cell carcinoma." J Cancer Res Clin Oncol. Feb. 2005;131(2):111-9. Epub Oct. 19, 2004.
Okano et al. "Genetic alterations in esophageal cancer." Methods Mol Biol. 2003;222:131-45.
Unger et al. "The tissue microenvironment as an epigenetic tumor modifier." Methods Mol Biol. 2003;223:315-47.
Beacham, et al. "Stromagenesis: the changing face of fibroblastic microenvironments during tumor progression." Semin Cancer Biol. Oct. 2005;15(5):329-41.
Amatangelo et al. "Stroma-derived three-dimensional matrices are necessary and sufficient to promote desmoplastic differentiation of normal fibroblasts." Am J Pathol. Aug. 2005;167(2):475-88.
Radisky et al. "Tumors are unique organs defined by abnormal signaling and context." Semin Cancer Biol. Apr. 2001;11 (2):87-95.
Mafhni et al. "The stroma as a crucial target in rat mammary gland carcinogenesis." J Cell Sci. Mar. 15, 2004;117(Pt 8):1495-502. Epub Mar. 2, 2004.
Liotta et al. "Metastatic potential correlates with enzymatic degradation of basement membrane collagen." Nature. Mar. 6, 1980;284(5751):67-8.

(Continued)

*Primary Examiner* — Kevin Hill
(74) *Attorney, Agent, or Firm* — Dann, Dorfman, Herrell & Skillman; Kathleen D. Rigaut

(57) ABSTRACT

A 3D organotypic culture which phenocopies aggressive, invasive cancer and methods of use thereof are provided.

37 Claims, 27 Drawing Sheets

(56) References Cited

OTHER PUBLICATIONS

Gupta, et al. "Cancer metastasis: building a framework." Cell. Nov. 17, 2006;127(4):679-95.
Andl et al. "Epidermal growth factor receptor mediates increased cell proliferation, migration, and aggregation in esophageal keratinocytes in vitro and in vivo." J Biol Chem. Jan. 17, 2003;278(3):1824-30. Epub Nov. 14, 2002.
Harada et al. "Telomerase induces immortalization of human esophageal keratinocytes without p16INK4a inactivation." Mol Cancer Res. Aug. 2003;1(10):729-38.
Takaoka et al. "Ha-Ras(G12V) induces senescence in primary and immortalized human esophageal keratinocytes with p53 dysfunction." Oncogene. Sep. 2, 2004;23(40):6760-8.
Kohn et al. "Construction and characterization of a conditionally active version of the serinetthreonine kinase Akt." J Biol Chem. May 8, 1998;273(19):11937-43.
Levin et al. "The discovery of anthranilic acid-based MMP inhibitors. Part 2: SAR of the 5-position and P1(1) groups." Bioorg Med Chem Lett. Aug. 20, 2001;11(16):2189-92.
Sengtpta et al. "p53: traffic cop at the crossroads of DNA repair and recombination." Nat Rev Mol Cell Biol. Jan. 2005;6(1):44-55.
Joerger et al. "Structures of p53 cancer mutants and mechanism of rescue by second-site suppressor mutations." J Biol Chem. Apr. 22, 2005;280(16):16030-7. Epub Feb. 9, 2005.
Parant et al. "Disrupting TP53 in mouse models of human cancers." Hum Mutat. Mar. 2003;21(3):321-6.
Olive et al. "Mutant p53 gain of function in two mouse models of Li-Fraumeni syndrome." Cell. Dec. 17, 2004;119 (6):847-60.
Reyolds et al. "Emerging roles for p120-catenin in cell adhesion and cancer." Oncogene. Oct. 18, 2004;23(48):7947-56.
Birchmeier et al. "E-cadherin as a tumor (invasion) suppressor gene." Bioessays. Feb. 1995;17(2):97-9.
Okawa et al. "The functional interplay between EGFR overexpression, hTERT activation, and p53 mutation in esophageal epithelial cells with activation of stromal fibroblasts induces tumor development, invasion, and differentiation." Genes Dev. Nov. 1, 2007;21(21):2788-803.
Nakamura et al. "Purification and characterization of a growth factor from rat platelets for mature parenchymal hepatocytes in primary cultures." Proc Natl Acad Sci U S A. Sep. 1986;83(17):6489-93.
Stoker et al. "Scatter factor is a fibroblast-derived modulator of epithelial cell mobility." Nature. May 21-27, 1987;327(6119):239-42.
Peschard et al. "From Tpr-Met to Met, tumorigenesis and tubes." Oncogene. Feb. 26, 2007;26(9):1276-85.
Comoglio et al. "Drug development of MET inhibitors: targeting oncogene addiction and expedience." Nat Rev Drug Discov. Jun. 2008;7(6):504-16.
Comoglio et al. "Invasive growth: from development to metastasis." J Clin Invest. Apr. 2002;109(7):857-62.
Knudsen et al. "Showering c-MET-dependent cancers with drugs." Curr Opin Genet Dev. Feb. 2008;18(1):87-96. Epub Apr. 9, 2008.
Jarvis. "One Pill, Many Uses." Chem. & Engin. News. Aug. 20, 2007;85(34):15-23.
Ren et al. "Hepatocyte growth factor promotes cancer cell migration and angiogenic factors expression: a prognostic marker of human esophageal squamous cell carcinomas." Clin Cancer Res. Sep. 1, 2005;11(17):6190-7.
Takada et al. "Expression of immunoreactive human hepatocyte growth factor in human esophageal squamous cell carcinomas." Cancer Lett. Nov. 6, 1995;97(2):145-8.
Iwazawa et al. "Primary human fibroblasts induce diverse tumor invasiveness: involvement of HGF as an important paracrine factor." Jpn J Cancer Res. Nov. 1996;87(11):1134-42.
Bhowmick et al. "TGF-beta signaling in fibroblasts modulates the oncogenic potential of adjacent epithelia." Science. Feb. 6, 2004;303(5659):848-51.
Orimo et al. "Stromal fibroblasts present in invasive human breast carcinomas promote tumor growth and angiogenesis through elevated SDF-1/CXCL12 secretion." Cell. May 6, 2005;121(3):335-48.
Soman et al. "The TPR-MET oncogenic rearrangement is present and expressed in human gastric carcinoma and precursor lesions." Proc Natl Acad Sci U S A. Jun. 1, 1991;88(11):4892-6.
Kuperwasser et al. "Reconstruction of functionally normal and malignant human breast tissues in mice." Proc Natl Acad Sci U S A. Apr. 6, 2004;101(14):4966-71. Epub Mar. 29, 2004.
Kudo et al. "Periostin promotes invasion and anchorage-independent growth in the metastatic process of head and neck cancer." Cancer Res. Jul. 15, 2006;66(14):6928-35.
Siriwardena et al. "Periostin is frequently overexpressed and enhances invasion and angiogenesis in oral cancer." Br J Cancer. Nov. 20, 2006;95(10):1396-403. Epub Oct. 24, 2006.
Puglisi et al. "Expression of periostin in human breast cancer." J Clin Pathol. Apr. 2008;61(4):494-8. Epub Oct. 24, 2007.
Gillan et al. "Periostin secreted by epithelial ovarian carcinoma is a ligand for alpha(V)beta(3) and alpha(V)beta(5) integrins and promotes cell motility." Cancer Res. Sep. 15, 2002;62(18):5358-64.
Sasaki et al. "Elevated serum periostin levels in patients with bone metastases from breast but not lung cancer." Breast Cancer Res Treat. Feb. 2003;77(3):245-52.
Sasaki et al. "Serum level of the periostin, a homologue of an insect cell adhesion molecule, as a prognostic marker in nonsmall cell lung carcinomas." Cancer. Aug. 15, 2001;92(4):843-8.
Sasaki et al. "Serum level of the periostin, a homologue of an insect cell adhesion molecule, in thymoma patients." Cancer Lett. Oct. 22, 2001;172(1):37-42.
Wang et al. "Small-molecule modulators of p53 family signaling and antitumor effects in p53-deficient human colon tumor xenografts." Proc Natl Acad Sci U S A. Jul. 18, 2006;103(29):11003-8. Epub Jul. 11, 2006.
Rios et al. "Periostin null mice exhibit dwarfism, incisor enamel defects, and an early-onset periodontal disease-like phenotype." Mol Cell Biol. Dec. 2005;25(24):11131-44.
Butcher et al. "Periostin promotes atrioventricular mesenchyme matrix invasion and remodeling mediated by integrin signaling through Rho/PI 3-kinase." Dev Biol. Feb. 1, 2007;302(1):256-66. Epub Oct. 4, 2006.
Tkatchenko et al. "Lack of periostin leads to suppression of Notch1 signaling and calcific aortic valve disease." Physiol Genomics. Nov. 6, 2009;39(3):160-8. Epub Sep. 1, 2009.
Radisky et al. "Tumors are unique organs defined by abnormal signaling and context." Semin Cancer Biol. Apr. 2001;11(2):87-95.
Mafhni et al. "The stroma as a crucial target in rat mammary gland carcinogenesis." J Cell Sci. Mar. 15, 2004:117(Pt 8):1495-502. Epub Mar. 2, 2004.
Puglisi et al. "Expression of periostin in human breast cancer." J Clin Pathol. Apr. 2008;61(4):494-8. Epub Oct. 15, 2007.
Butcher et al. "Periostin promotes atrioventricular mesenchyme matrix invasion and remodeling mediated by integrin signaling through Rho/Pl 3-kinase." Dev Biol. Feb. 1, 2007;302(1):256-66. Epub Oct. 4, 2006.

\* cited by examiner

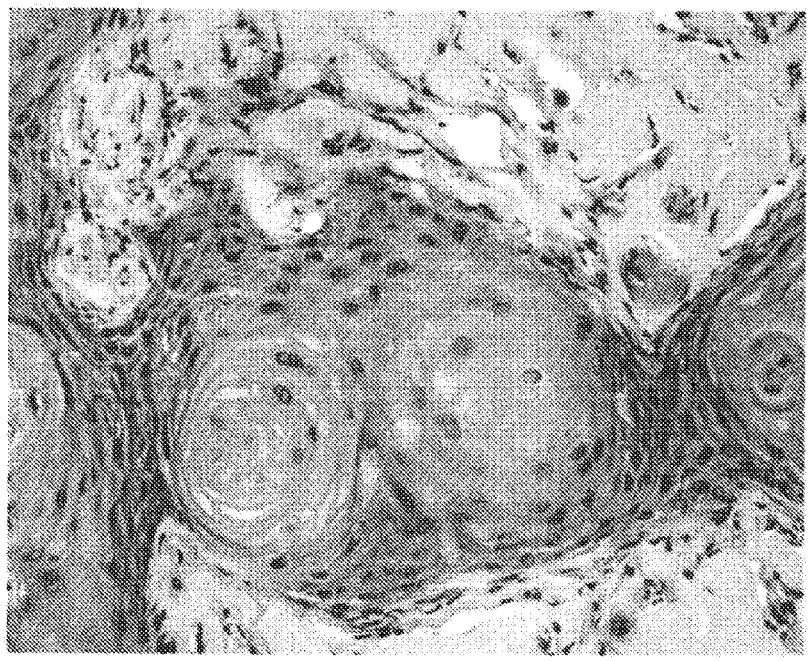
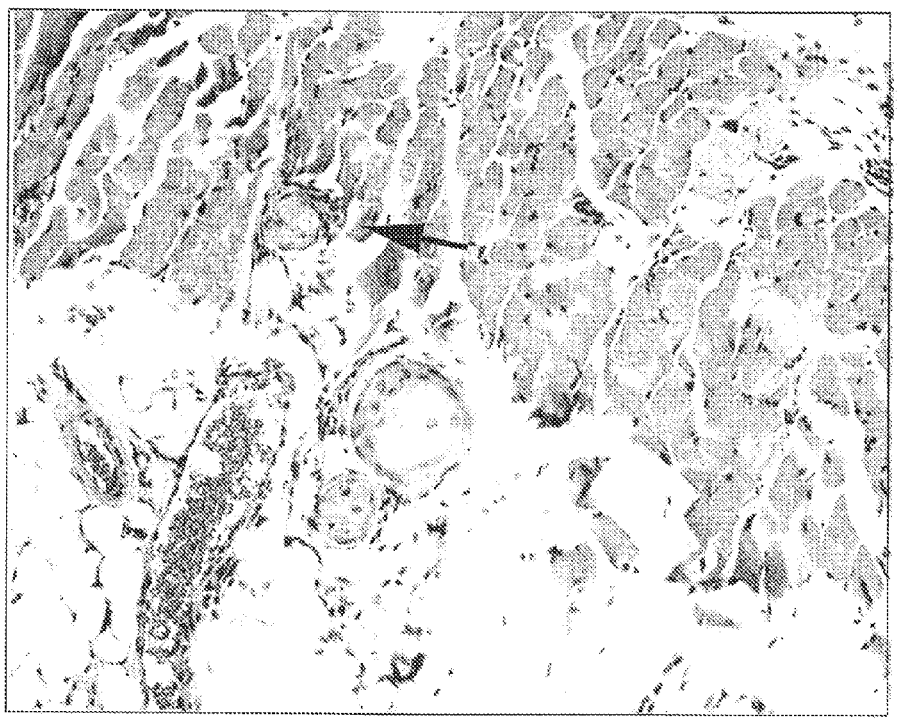
Figure 17

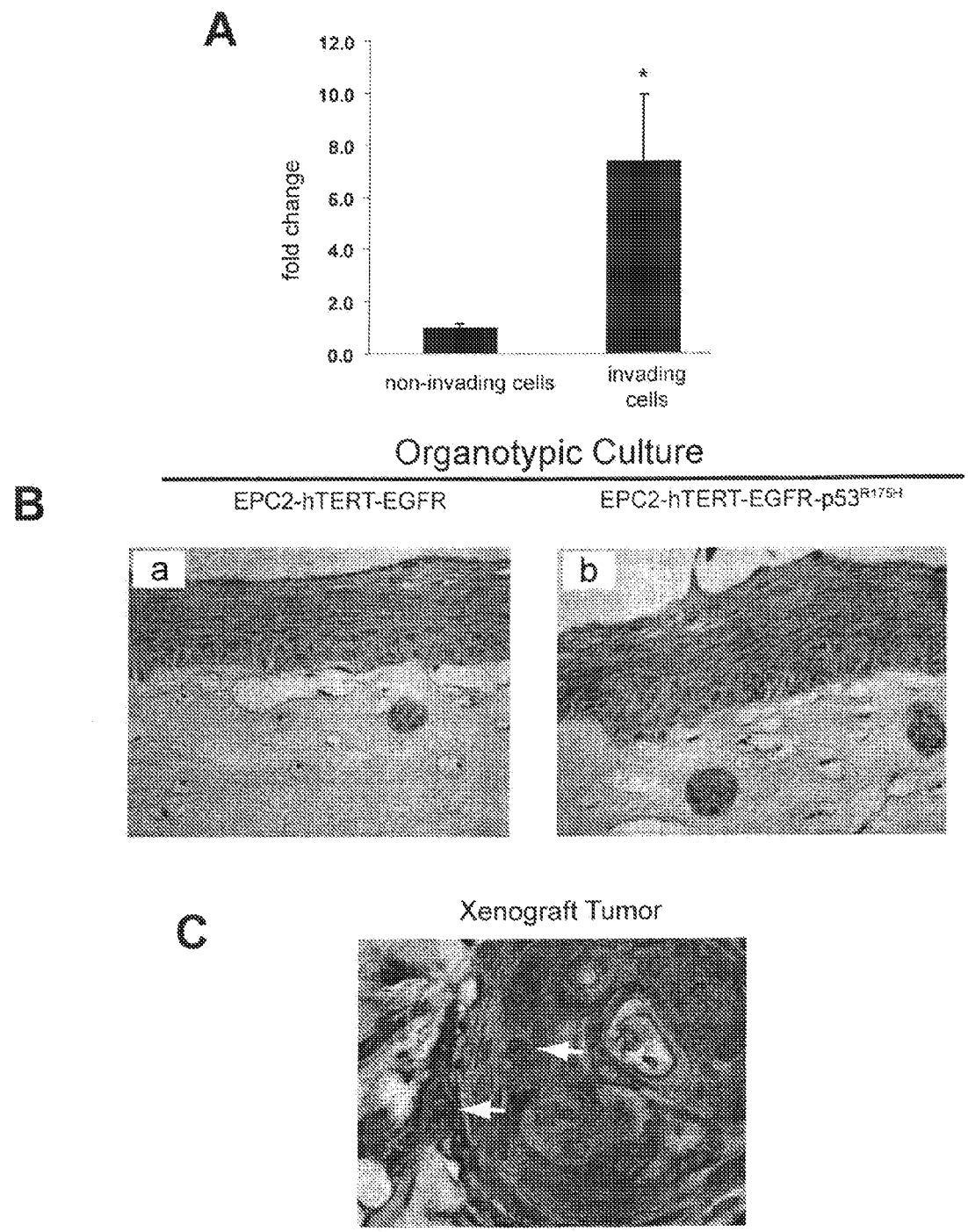

Figure 21
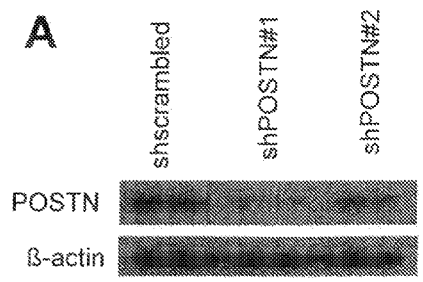
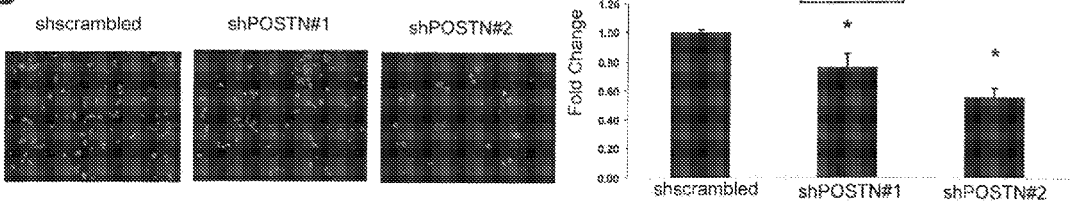
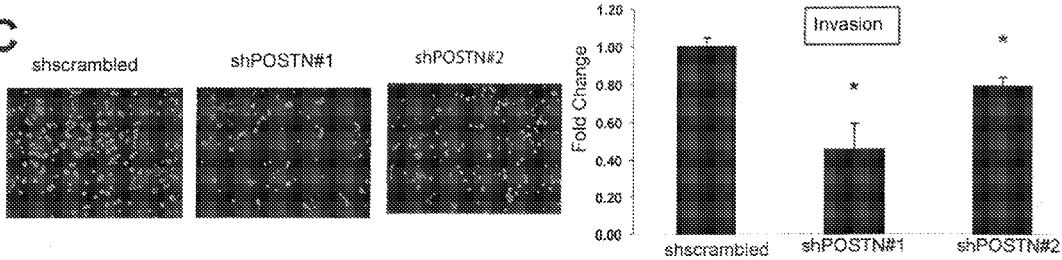
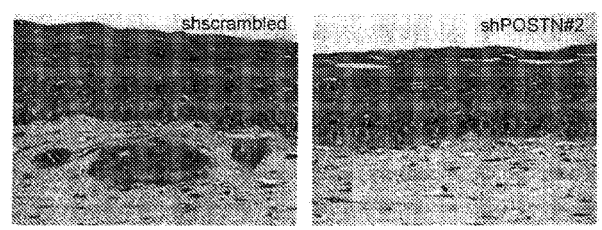
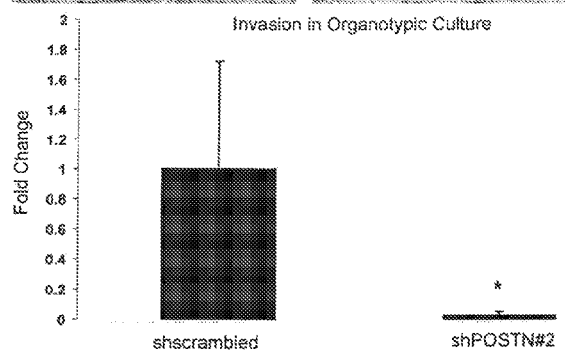

Figure 23
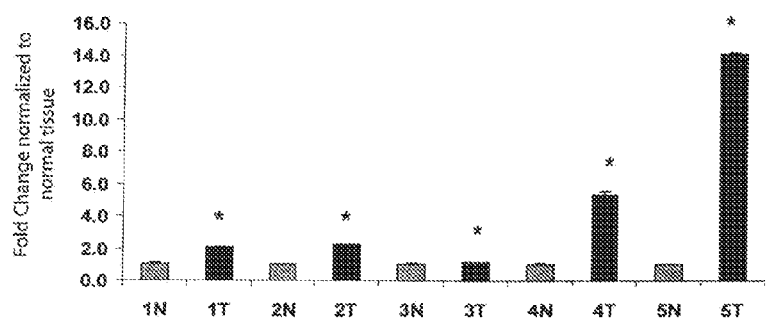
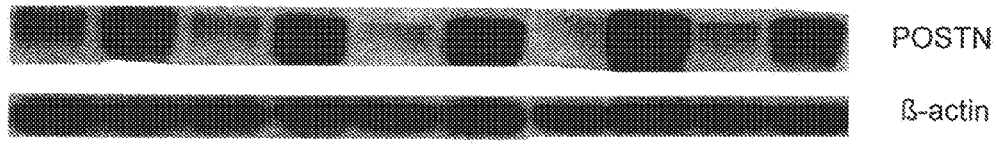
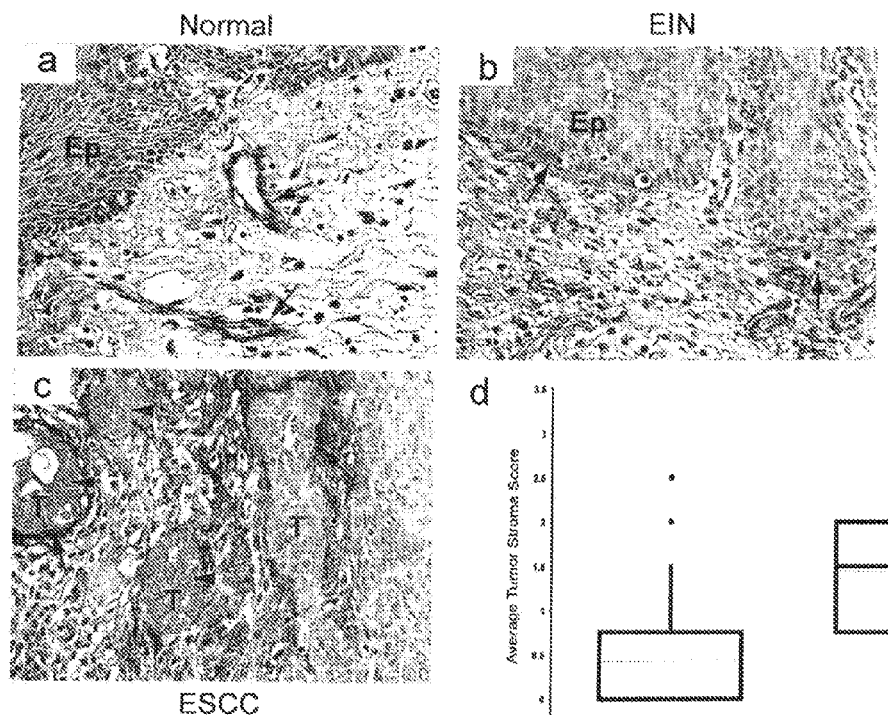

Figure 24
A
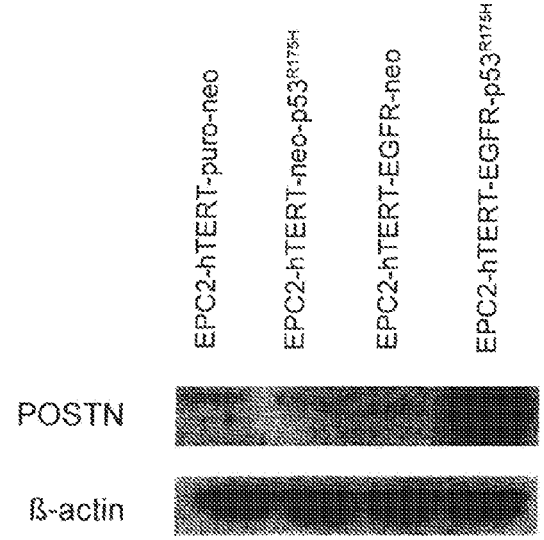
B
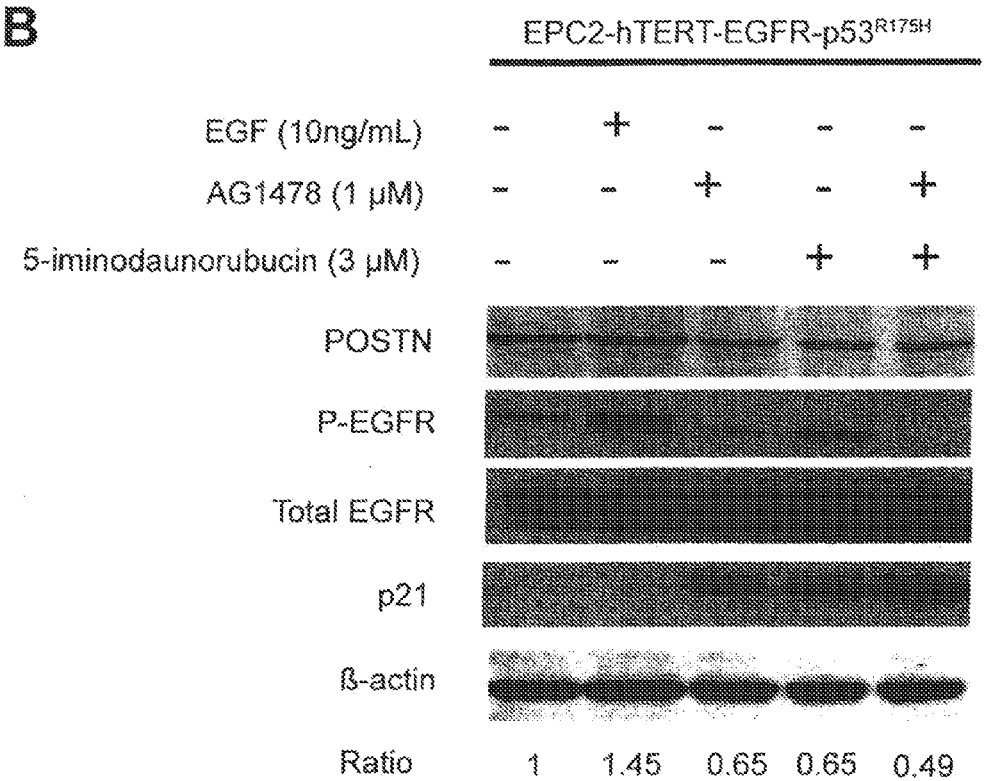

CULTURE BASED SCREENING ASSAY AND METHODS OF USE THEREOF TO IDENTIFY AGENTS WHICH MODULATE TUMOR DEVELOPMENT, INVASION AND DIFFERENTIATION

This application is a §365 application of PCT/US2008/081967 filed Oct. 31, 2008 which in turn claims priority under 35 U.S.C. §119(e) to U.S. Provisional Application 60/984,190, filed Oct. 31, 2007, the contents of each being incorporated herein by reference as though set forth in full.

Pursuant to 35 U.S.C. §202 (c), it is acknowledged that the U.S. Government has certain rights in this invention, which was made in part with funds from the National Institutes of Health, Grant Numbers P01-CA098101, F32-DK075230, K01-DK066205 P30-DK050306, NIH-T32-CA115299, NIH/NRWA F32 DK-082149-01 and U54-CA105008.

FIELD OF THE INVENTION

This application relates to the fields of cancer and the development of diagnostics and therapeutics for cancer. More specifically, the invention provides three-dimensional organotypic cell culture models which facilitate the screening and development of diagnostic and therapeutic agents having efficacy for the treatment of aberrant proliferative disorders, including without limitation, cancer and other hyperplasia and dysplasia related disorders.

BACKGROUND OF THE INVENTION

Several publications and patent documents are cited throughout the specification in order to describe the state of the art to which this invention pertains. Each of these citations is incorporated herein by reference as though set forth in full.

Esophageal squamous cell carcinoma (ESCC) is one of the most aggressive squamous cell cancers compared to those originating at other sites, such as skin, head/neck, lung and anogenital tract. The reasons underlying these differences are somewhat surprising in that there is commonality in the type and frequency of pivotal genetic alterations and environmental exposures. In this context, the prognosis for patients with ESCC remains poor, due to the high rate of local and distant metastases at time of diagnosis (Enzinger and Mayer (2003) N. Engl. J. Med. 349:2241-52) Common genetic alterations identified in ESCC include epidermal growth factor receptor (EGFR) (up to 70%) and cyclin D1 oncogene overexpression (up to 60-70%), inactivation of the p53 (50-60%) and p16$^{INK4a}$ (40-50%) tumor suppressor genes, and hTERT activation (Mandard et al. (2000) Mutat. Res. 462: 335-342; Metzger et al. (2004) Onkologie 27: 200-206); Sunpaweravong et al. (2005) J. Cancer Res. Clin. Oncol. 131:111-119). Cyclin D1 and EGFR overexpression appear to be associated with early events in tumor initiation, in particular with pre-neoplastic (squamous dysplasia) and early neoplastic stages, whereas p53 and p16 inactivation are associated with tumor progression in advanced neoplastic stages (Mandard et al. (2000) supra; Okano et al. (2003) Meth. Mol. Biol. 222:131-145). While these are the canonical genetic alterations that delineate ESCC initiation and progression, genomic approaches have added to the library of other genes and pathways that are important, although not as compelling in terms of high frequency.

Genetic alterations in epithelial tumors, such as squamous cell cancers, help to drive tumor cell migration and invasion into the extracellular matrix. The mesenchymal stroma (or connective tissue) is essential for the maintenance of the epithelium. Genetically altered epithelial cells modify the stromal compartment so as to establish a permissive and supportive environment for cancer cell invasion (Unger and Weaver (2003) Meth. Mol. Biol. 223:315-347). The fibroblasts are one of several cell types involved in the stromal compartment mediated regulation of epithelial cancer (Beacham and Cukierman (2005) Semin. Cancer Biol. 15:329-341). The fibroblastic population is very heterogeneous and it varies from tissue to tissue and from site to site. It is however accepted to define fibroblasts as the cells responsible for producing, maintaining and modifying the extracellular matrices of connective tissue. These cells are normally spindled or stellate in shape and are responsible for maintaining homeostatic equilibrium in connective (or mesenchymal) compartments. Fibroblasts are characterized as being vimentin positive, E-cadherin negative and spindle-shaped in 2D cultures as well as 3D matrices (Amatangelo et al. (2005) Am. J. Pathol. 167:475-488).

The fibroblasts in the cancer stroma are activated myofibroblasts or cancer associated fibroblasts (Beacham and Cukierman (2005), supra. In some cases, the trigger for neoplastic progression may come from signals within the stromal microenvironment (Radisky et al. (2001) Semin. Cancer Biol. 11:87-95; Maffini et al. (2004) J. Cell Sci. 117:1495-1502). It is increasingly apparent that mesenchymal stromal fibroblasts modulate tumor cell migration and invasion through autocrine and paracrine mechanisms involving, in part, secreted growth factors and cytokines. In addition, both epithelial cells and stromal fibroblasts produce enzymes that degrade the epithelial basement membrane, as well as the mesenchymal ECM (Liotta et al. (1991) Nature 284:67-68), such as matrix metalloproteinases (MMPs). Tumor cell invasion into the ECM with subsequent metastasis to distant organs via hematogenous and lymphatic dissemination are critical steps in tumor viability and progression (Gupta and Massague (2006) Cell 127:679-695).

SUMMARY OF THE INVENTION

A well characterized three dimensional cellular model which recapitulates invasive cancer from specific tissues of origin is urgently needed to facilitate the identification of agents having efficacy against this disease. Moreover, such models can be individualized to identify those most likely to benefit and to further create personalized therapy regimens that are appropriate to the patient being treated. Accordingly, provided herein is a cell culture based system which exhibit the aggressive and invasive properties of difficult to treat cancers.

In one embodiment, primary human cells transduced with at least one activated oncogene, and at least one inactivated tumor suppressor gene and grown in 3D culture to produce transformed cells which mimic the features of invasive, metastatic cancer cells are provided. Such primary human cells, include, without limitation, cells of esophageal, colon, cervical, head/neck, oral cavity, tracheal and ano-gentical origin. In a particularly preferred embodiment, the cells are transduced with nucleic acids encoding epidermal growth factor receptor (EGFR), the catalytic subunit of human telomerase (hTERT), and p53$^{R175H}$, genes that are frequently altered in human squamous cell cancers thereby forming cells which demonstrate increased migration and invasion when compared to control cells. This enhanced invasion phenotype provides a powerful read-out for use in screening assays to identify agents which modulate this process.

Thus, another aspect of the invention comprises a method of use of the cultures described above in a screening method to identify agents which modulate the ability of cells to invade the underlying extracellular matrix or induce formation of dysplastic epithelium.

In yet another embodiment, keratinocytes and fibroblasts are obtained from a tumor biopsy and placed in organotypic culture and subjected to the methods disclosed herein. Patient specific cultures such as these provide the means to identify and streamline chemotherapeutic approaches.

Another aspect of the invention comprises a genetic signature associated with increased cellular migration and invasiveness and methods of use thereof for identifying tumor biopsy samples with an increased likelihood to exhibit invasive properties. Organotypic cultures exhibiting these genetic signatures can also be employed in screening assays to identify test compounds which modulate their expression levels, thereby identifying agents having efficacy in the prevention of tumor cell migration and metastasis.

Kits comprising the cells and other reagents necessary to practice the present invention are also provided.

Conditioned media from FEF4736 fetal esophageal fibroblasts±HGF or empty vector (puro) promotes invasion of transformed esophageal epithelial cells. Fluorescence measurements representing invading cells on the bottom filters of Matrige®-coated Boyden chambers with the indicated fibroblast derived conditioned media sample used as the chemoattractant of EPChTERT-EGFR-$p53^{R175H}$ cells seeded atop the filter. (C) H&E sections of organotypic cultures of FEF4736 fibroblasts±HGF seeded into the matrix with EPC-hTERT-EGFR-p53$^{R175H}$ grown above (scale bar=100 μm). Error bars represent±SEM and * indicates p values≤0.05 compared to either empty vector cell line.

Figure 15:
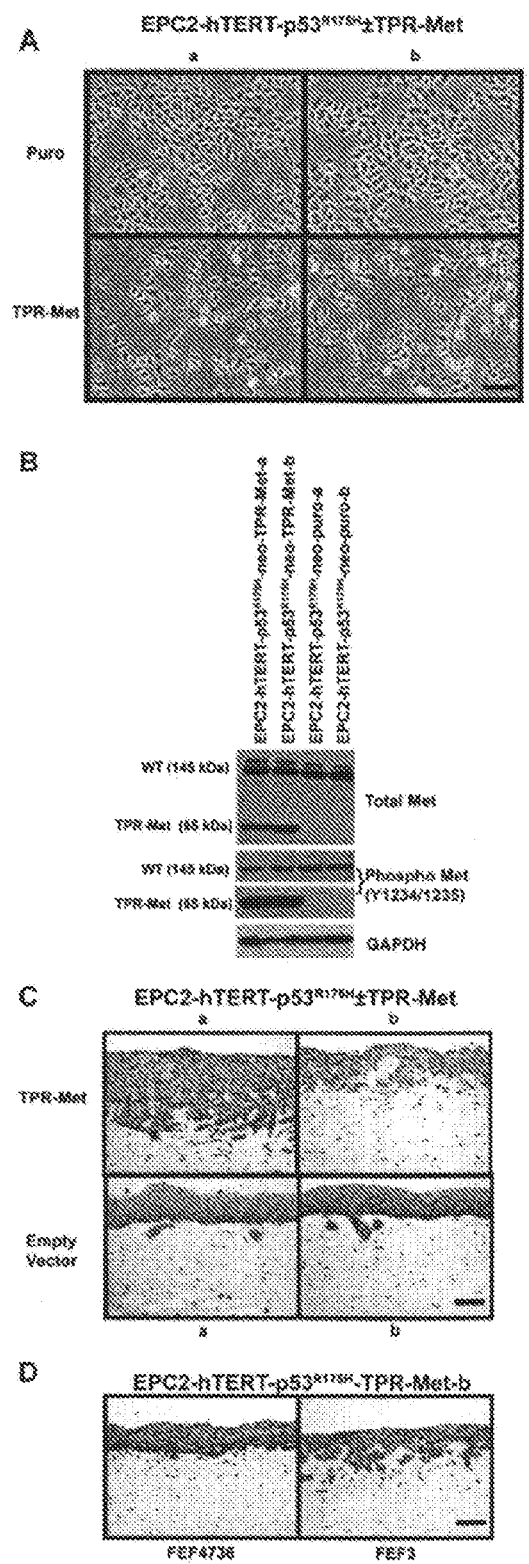

FIG. 15 shows expression of constitutively active Met enhances invasion of transformed esophageal epithelial cells. (A) Phase contrast images of EPC-hTERT-p53$^{R175H}$-TPR-Met or EPC-hTERTp53R175H-puro grown in 2D on tissue culture plastic. Images a and b represent independently generated cell lines with the same genotype (scale bar=100 μm). (B) Western blot of EPChTERT-p53$^{R175H}$-TPR-Met or EPC-hTERT-p53$^{R175H}$-puro whole cell lysates for detection of wild type Met (145 kDa), TPR-Met (65 kDa), as well as phosphorylation status. (C&D) H&E sections of organotypic culture of EPC-hTERT-p53$^{R175H}$-TPR-Met or EPC-hTERT-p53$^{R175H}$-puro cells seeded above matrices containing FEF3 (C&D) or FEF4736 (D) fetal esophageal fibroblasts (scale bar=100 μm).

Figure 16:
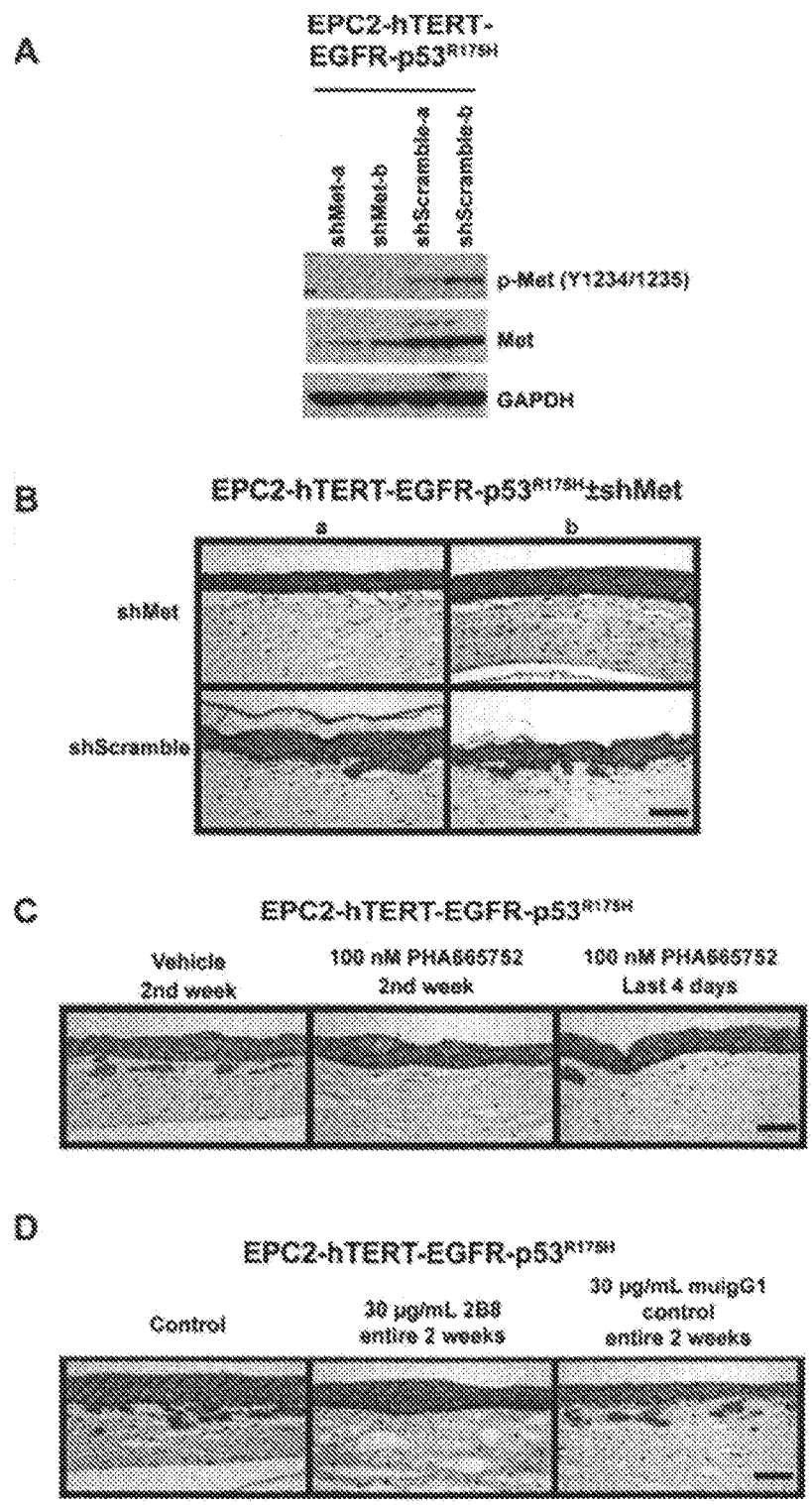

FIG. 16 shows inhibition of HGF/Met pharmacologically or by genetic knockdown in transformed esophageal epithelial cells reduces invasion. (A) Western blot of EPC-hTERT-EGFR-p53$^{R175H}$shMet or EPC-hTERT-EGFR-p53$^{R175H}$shScramble cells (two independent lines of each genotype) to determine extent of Met knockdown of total protein and activation state. (B) H&E sections of organotypic culture of EPC-hTERT-EGFR-p53$^{R175H}$-shMet or EPC-hTERT-EGFRp53$^{R175H}$-shScramble cells seeded above matrices containing FEF3 fetal esophageal fibroblasts. (C) H&E sections of organotypic cultures of EPC-hTERT-EGFR-p53$^{R175H}$ cells seeded above FEF3 matrices treated with DMSO vehicle (days 7-15) or 100 nM PHA665752 (days 7-15 or day 11-15) as indicated. (D) H&E sections of organotypic cultures of EPC-hTERT-EGFR-p53$^{R175H}$ cells seeded above FEF3 matrices treated with 30 μg/mL 2B8 or muIgG1 control antibody (days 0-15) as indicated. Scale bar represent 100 μm in all images.

Figure 17:
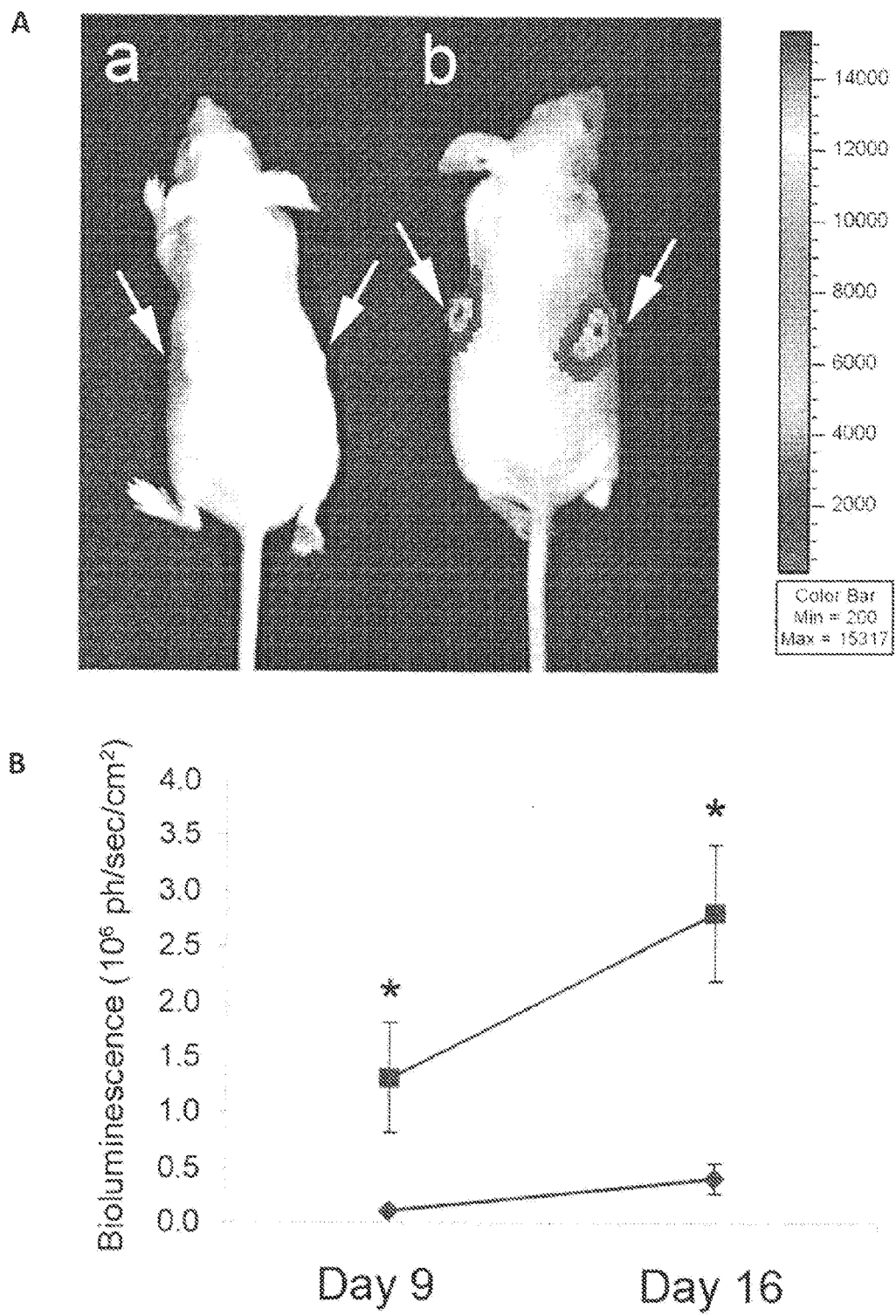

FIG. 17 shows A. In vivo bioluminescence imaging of control EPC2-hTERT-EGFR-puro-Luc (a) and EPC2-hTERT-EGFR-p53$^{R175H}$-Luc (b) cells implanted subcutaneously into athymic nude mice. B. The graph demonstrates average bioluminescence signal (photons per second per square centimeter)±SEM for control (blue) and triple mutant (red) cells; n=12 injection sites per cell line; (*)P<0.02 at day 9 and P<0.002 at day 16 after injection. C. & D. H&E staining of representative tumor formed in vivo by EPC2-hTERT-EGFR-p53$^{R175H}$ cells revealed a squamous cell carcinoma phenotype with invasion (black arrow) through the extracellular matrix into muscle (100×). E. Alpha-smooth muscle actin staining of mouse fibroblasts is observed surrounding the tumor (100-200×).

Figure 18:
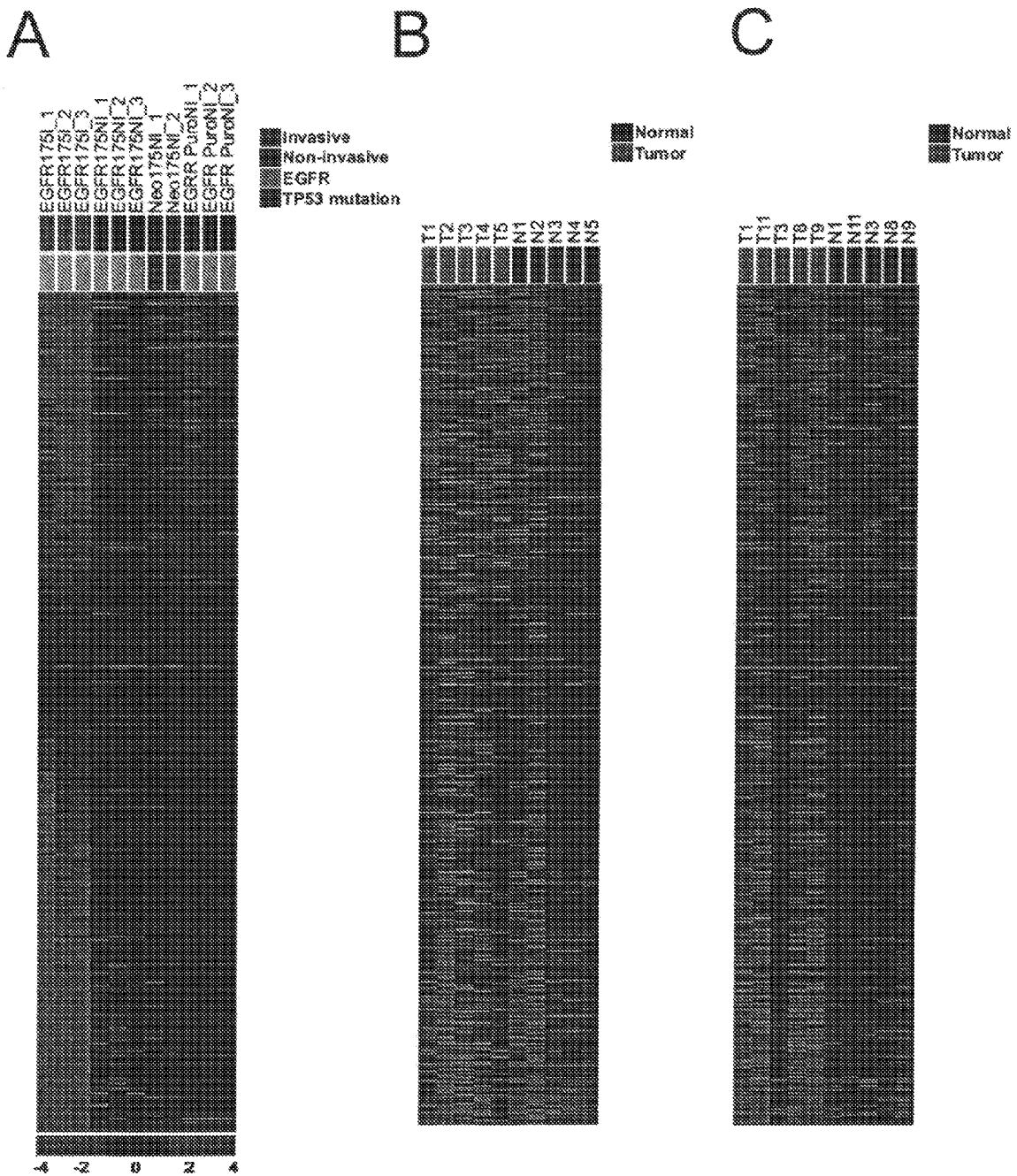

FIG. 18. Invasive signature from EPC2-hTERT-EGFR-p53$^{R175H}$ cells classifies with human ESCC. (A) Microarray analysis of LCM-extracted RNA from invading EPC2-hTERT-EGFR-p53$^{R175H}$ cells grown in organotypic culture (n=3) compared to non-invading EPC2-hTERT-EGFR-p53$^{R175H}$ (n=3) as well as non-invading EPC2-hTERT-EGFR-puro (n=3) and EPC2-hTERT-neop53$^{R175H}$ cells (n=2). Differentially expressed probesets were subjected to supervised hierarchical clustering and expression is based on a $\log_2$ scale where red represents upregulation and green represents downregulation. Heatmap denotes probeset list (PSL) of 939 probesets representing unique tumor invasive signature characterizing invasive phenotype. Tumor invasive signature comprises differentially expressed probesets (p<0.0001). (B and C) Heatmap representation of gene expressing profiles from two independent cohorts each comprising of five paired ESCC tumors classified using the tumor invasive signature from (A). Due to microarray platform difference (U133 v2.0 and U133A) used in 2 independent cohorts, only 648 probesets were shared in both platforms. All probesets are in the same order as seen in (A).

Figure 19A:
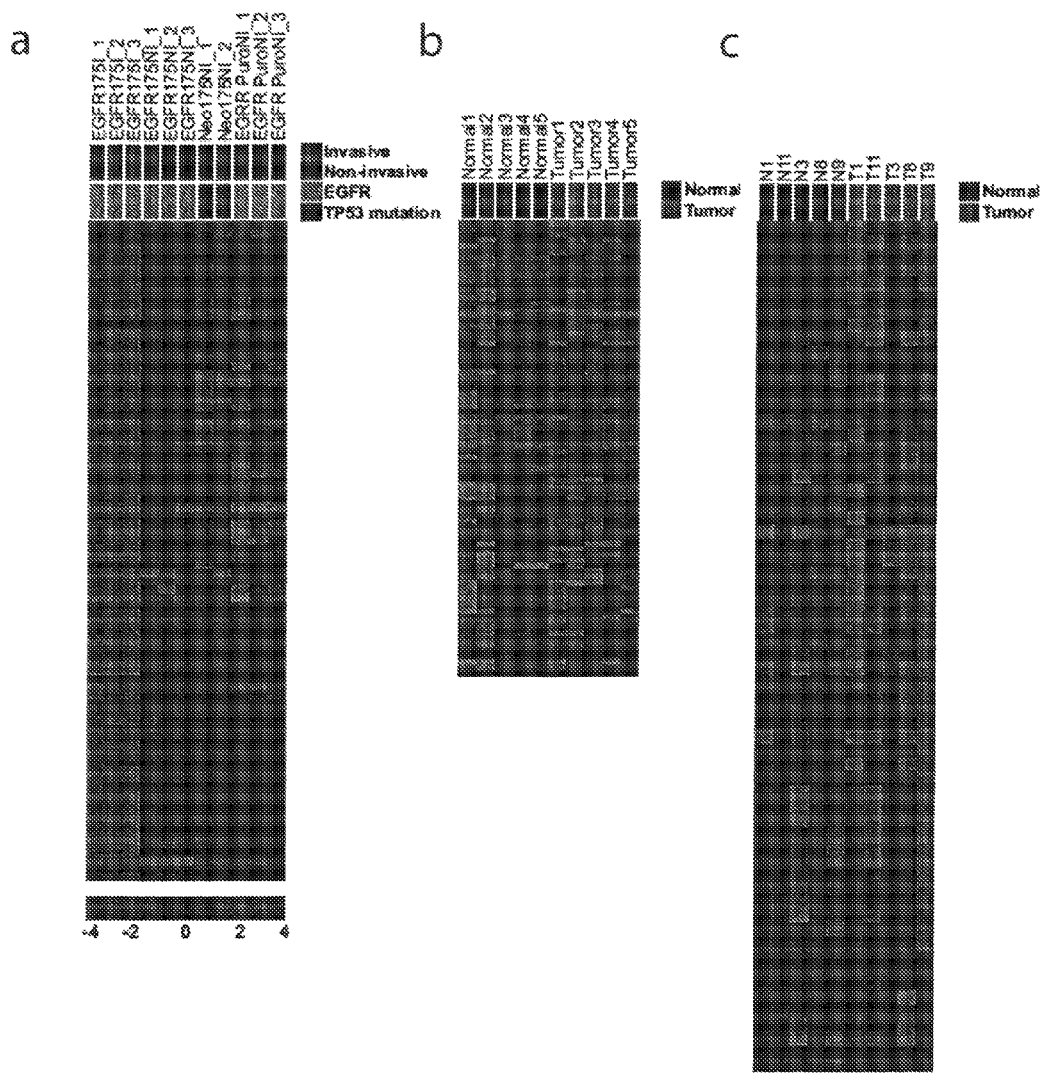
Figure 19B:
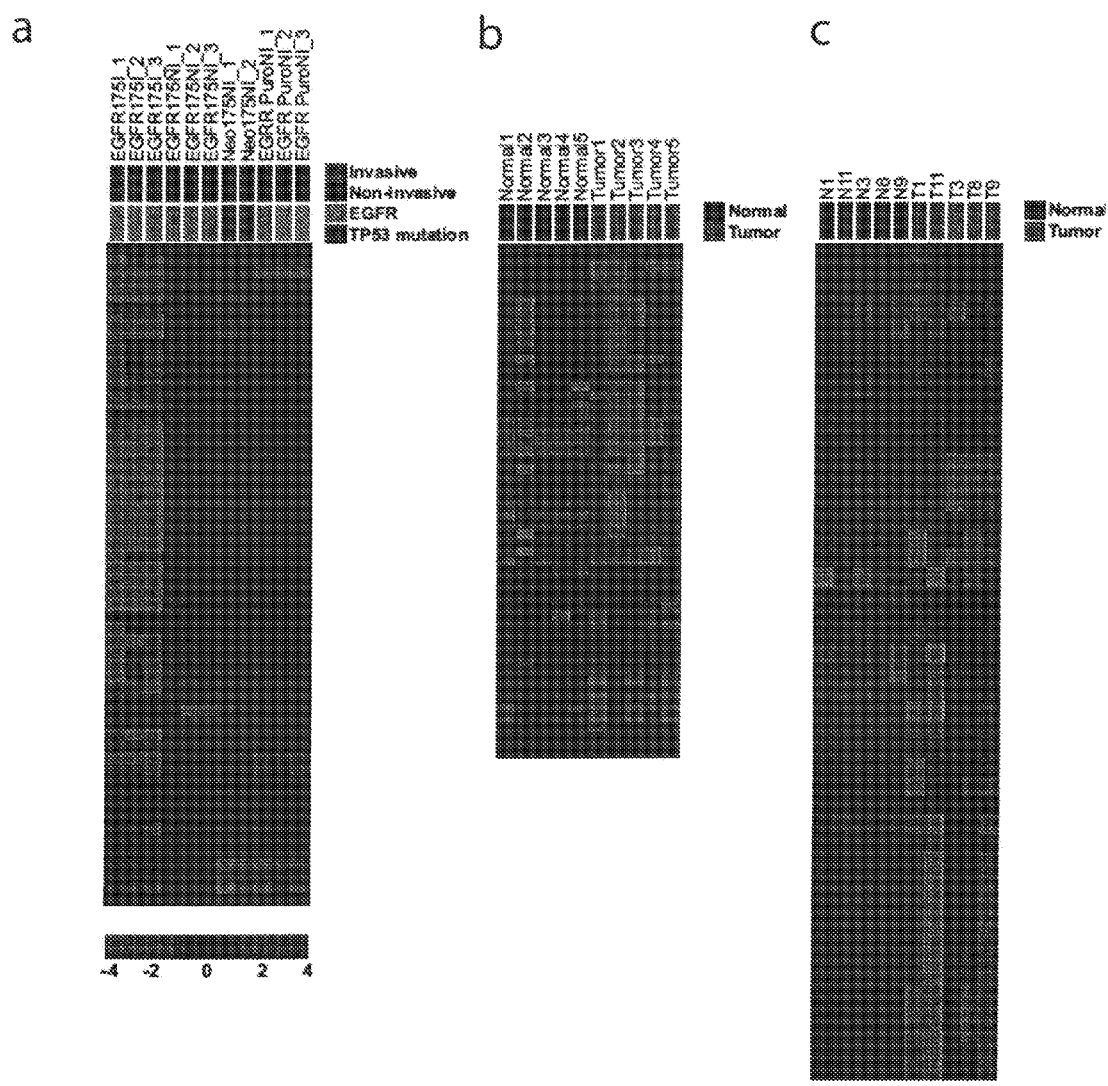
Figure 19C:
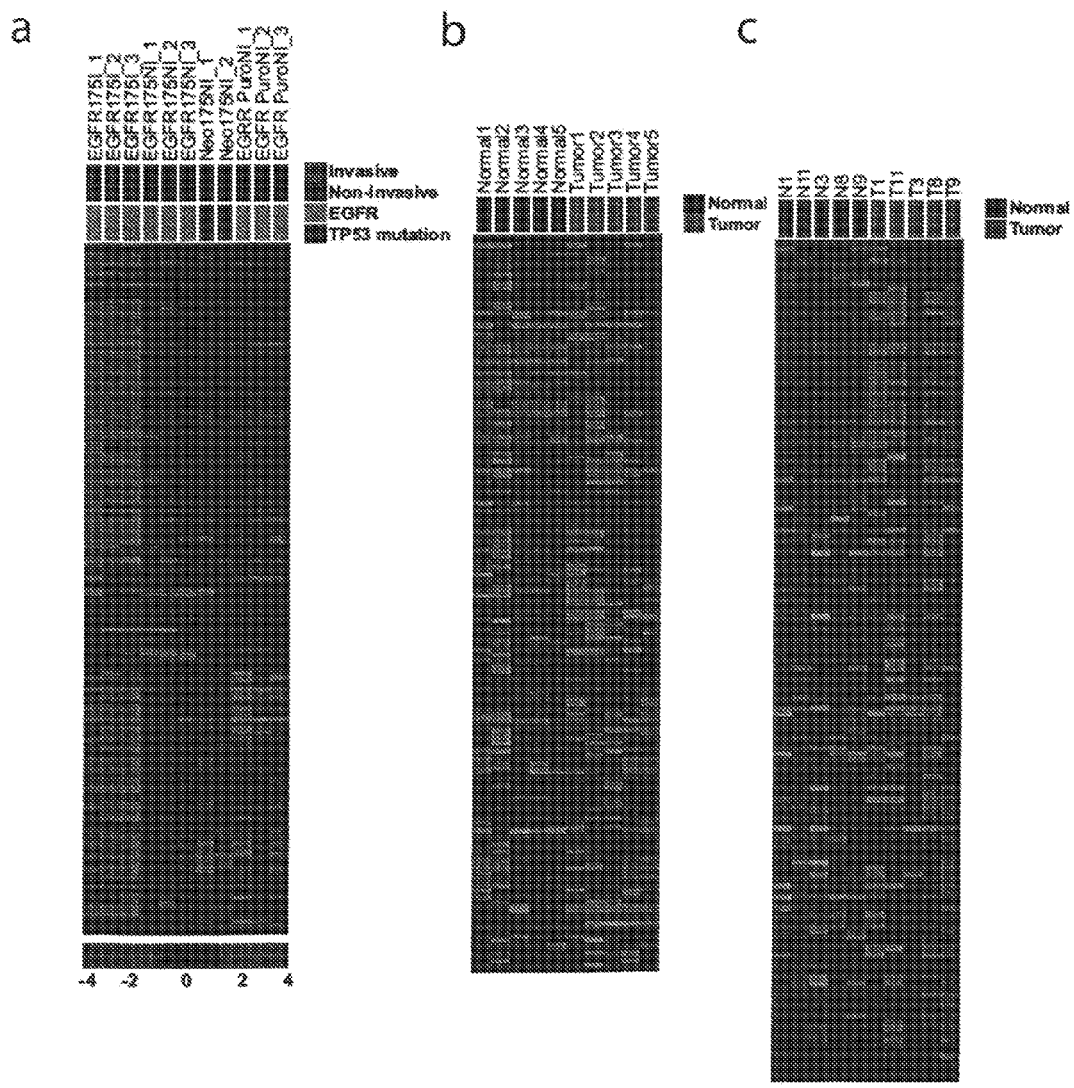

FIG. 19: Heatmap representation of differentially expressed genes enriched in Gene Ontology (GO) Biological Processes in invasive EPC.hTERT.EGFR.p53$^{R175H}$ cell lines versus 2 cohorts of human ESCC using DAVID. (A) Heatmaps representing supervised hierarchical clustering of genes enriched in GO Biological Process cell adhesion and biological adhesion seen in (a) invasive EPC2-hTERT-EGFR-p53$^{R175H}$ cell lines versus non-invasive EPC2-hTERT-EGFR-p53$^{R175H}$/EPC2-hTERT-EGFR/EPC2-hTERT-p53$^{R175H}$,(b) human ESCC (Tumor 1-5) versus non-invasive esophageal tissue (Normal 1-5) and (c) human ESCC (T1,3, 8,9,11) versus non-invasive esophageal tissue (N1,3,8,9,11). (B and C) Similar to FIG. 19A, gene enrichment in Development Processes (S1B) and Cellular Component Organization and Biogenesis (S1C).

FIG. 20: Periostin is expressed preferentially in invading EPC2-hTERT-EGFR-p53$^{R175H}$ cells. (A) Fold change of periostin expression in invading versus non-invading EPC2-hTERT-EGFR-p53$^{R175H}$ cells isolated by LCM from organotypic culture and quantified by qPCR. (*)P-value<0.05 (B) Immunohistochemistry analysis of periostin expression in control EPC2-hTERT-EGFR cells (Left panel a) and invading EPC2-hTERT-EGFR-p53$^{R175H}$ cells (Right panel b) grown in organotypic culture (OTC). Rabbit polyclonal periostin antibody recognizes exogenous and secreted periostin. (C) Periostin expression by immunohistochemistry of tumor formed in vivo by EPC2-hTERT-EGFR-p53$^{R175H}$ cells. Periostin expression in tumor epithelial-stromal interface indicated (white arrows). (200× Magnification)

FIG. 21: Periostin knockdown in EPC2-hTERT-EGFR-$p53^{R175H}$ cells reduces migration and invasion (A) Western blot confirming periostin (90 kDal) knock-down in EPC2-hTERT-EGFR-p53$^{175H}$ cells using two independent shRNA contructs. (B) Representative fluorescent images obtained from bottom filter of a Boyden chamber migration assay show reduced migration in EPC2-hTERT-EGFR-$p53^{R175H}$ cells expressing shRNA to periostin versus control (scrambled) shRNA to periostin. Experiments were performed in triplicate. (*) P<0.04 for shPOSTN#1 vs shscrambled, (*) P<0.001 for shPOSTN#2 vs shscrambled. (C) Images and quantifications of the Matrigel® invasion assay were acquired and processed as in (B). Experiments were performed in triplicate. (*) P<0.02 for shPOSTN#1 vs shscrambled, (*) P<0.05 for shPOSTN#2 (D) H & E staining of organotypic culture comparing shRNA to periostin versus scrambled shRNA showing decreased invasion of EPC2-hTERT-EGFR-p53$^{R175H}$ cells expressing shRNA to periostin. Bar graphs represent fold change in invasion+/−SEM, P=0.015 (200× magnification).

Figure 22:
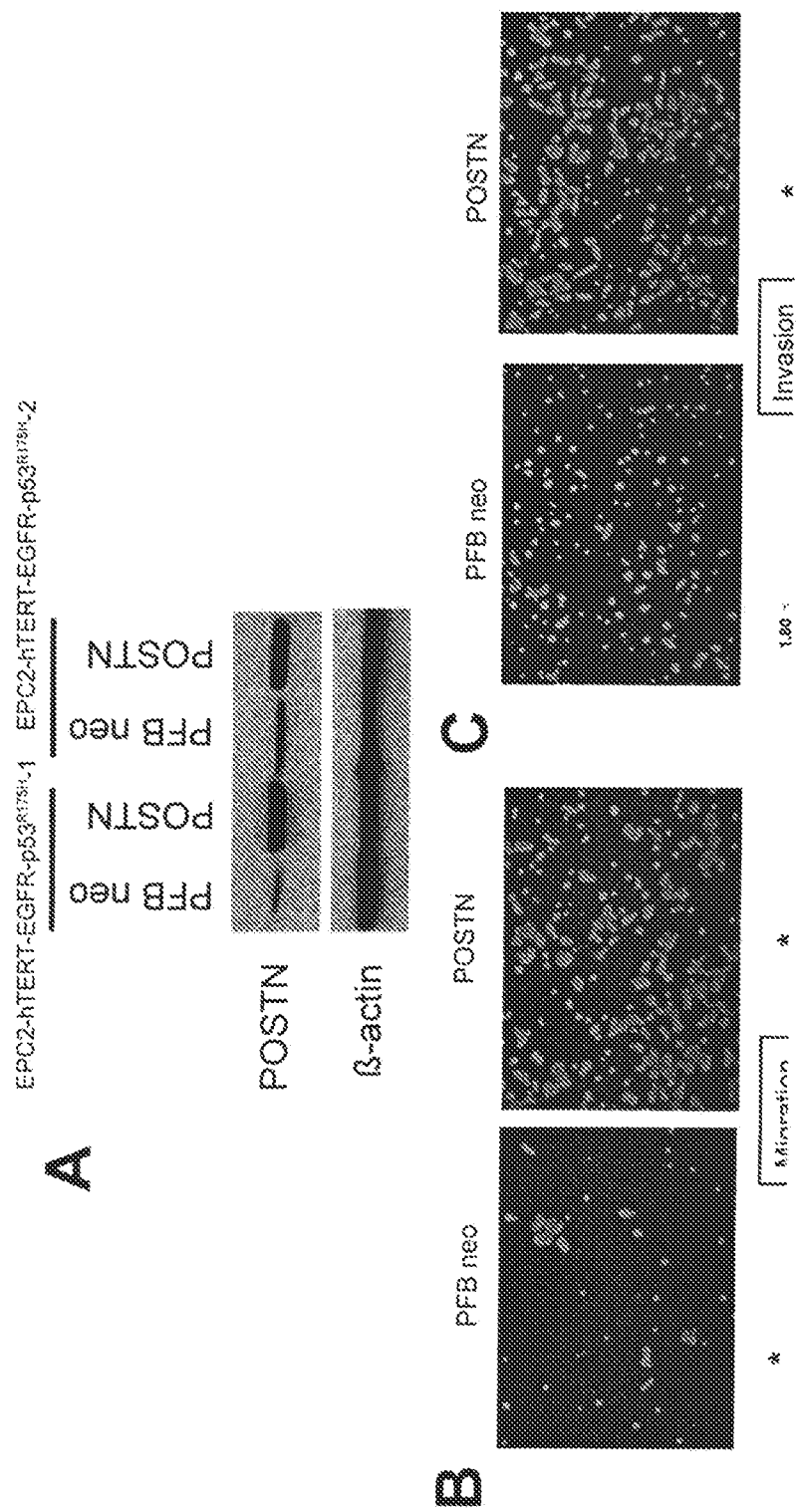

FIG. 22: Periostin overexpression in EPC2-hTERT-EGFR-p53$^{R175H}$ cells promotes increased migration and invasion in vitro and in organotypic culture (A) Western blot confirming periostin (90 kDal) overexpression in two independent EPC2-hTERT-EGFR-p53$^{R175H}$ cell lines. pFB neo was used as an empty control vector. (B) Representative fluorescent images obtained from bottom filter of a Boyden chamber migration assay show enhanced migration in EPC2-hTERT-EGFR-$p53^{R175H}$ cells that overexpress periostin versus control EPC2-hTERT-EGFR-p53$^{R175H}$-neo cells. Bar graphs represent fold changes+/−SEM (*) P<0.01 (Student t-test, EPC2-hTERT-EGFR-p53$^{R175H}$ periostin overexpressing cells vs. control cells). Note that P<0.05 is statistically significant. Experiments were done in triplicate. (C) Images and quantifications of the Matrigel®invasion assay were acquired and processed as in (B). (*) P<0.04 (D) H & E staining of organotypic cultures comparing EPC2-hTERT-EGFR-p53$^{R175H}$ periostin overexpressing cells to empty vector control cells reveal increased invasion of EPC2-hTERT-EGFR-p53$^{R175H}$ periostin overexpressing cells. Bar graphs represent fold change in invasion+/−SEM, (*) P<0.03 (EPC2-hTERT-EGFR-p53$^{R175H}$ periostin overexpressing cells vs empty control vector cells). (200× magnification).

FIG. 23: Periostin is overexpressed in primary ESCC tumors and is associated with ESCC tumor progression (A) Relative periostin mRNA expression measured by real-time PCR in 5 primary ESCC tumor specimens with paired adjacent non-invasive esophageal tissue. (*)P-value<0.05. (B) Western blot analysis of periostin expression in 5 primary ESCC tumor specimens with paired adjacent non-invasive esophageal tissue. Expression of β-actin was used as an internal loading control. (C)Immunohistological analysis of a tissue microarray comprising of 73 human ESCC cases with normal esophageal tissue. Representative photomicrographs of periostin expression in normal esophageal tissue, high grade esophageal intraepithelial neoplasia (EIN) and ESCC. Periostin expression was observed around blood vessels (Left panel a, arrows). Periostin staining observed in EIN epithelial-stroma interface (Right panel b, arrows) and accumulation in tumor stroma (Bottom panel c, arrows) and tumor cells (Bottom panel c, arrowheads). (400× magnification). Stroma in tissue microarray was scored for periostin staining intensity and average score of 2 cores from each case were taken. ESCC cases scored higher levels of periostin expression (n=73, Mean=1.44, s.d+/−=0.97) compared to matched normal controls (n=69, Mean=0.44, s.d+/−=0.68) (panel d). Closed circles represent outliers. Student's t-test, ESCC cases vs matched normal esophagus controls. (**)p-value<0.01

FIG. 24: Periostin expression is dependent upon EGFR signaling and mutant p53 activation (A) Western blot analysis of periostin (90 kDa) in EPC2-hTERT-EGFR-p53$^{R175H}$, EPC2-hTERT-puro-neo, EPC2-hTERT-EGFR-neo and EPC2-hTERT-neo-p53$^{R175H}$ cells. (B) Western blot analysis of periostin expression in EPC2-hTERT-EGFR-p53$^{R175H}$ cell lysates after 24 h treatment with EGF (10 ng/μl), EGFR inhibitior AG1478 (1 μM) and 5-iminodaunorubicin (3 μM). Immunoblotting for total EGFR and phosphorylated EGFR to confirm inhibition of EGFR as well as p21 to indicate restoration of wildtype p53 signaling. β-actin was used as a loading control. Densitometry ratios of periostin/β-actin were calculated and recorded.

Figure 25:
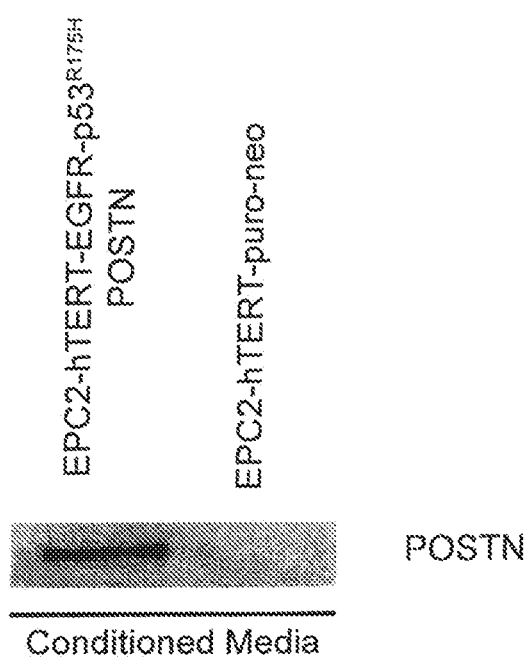

FIG. 25: Western blot analysis comparing secreted periostin (POSTN) expression in conditioned media harvested from EPC2-hTERT-EGFR-p53R175H POSTN and EPC2-hTERT-puro-neo cells.

DETAILED DESCRIPTION OF THE INVENTION

Esophageal cancer is a prototypic squamous cell cancer that carries a poor prognosis, primarily due to presentation at advanced stages. Human esophageal epithelial cells were utilized as a platform to recapitulate esophageal squamous cell cancer, thereby providing insights into the molecular pathogenesis of squamous cell cancers in general. This was achieved through the retroviral mediated transduction into normal, primary human esophageal epithelial cells of epidermal growth factor receptor (EGFR), the catalytic subunit of human telomerase (hTERT), and p53$^{R175H}$, genes that are frequently altered in human esophageal squamous cell cancer. These cells demonstrated increased migration and invasion when compared to control cells. When these genetically altered cells were placed within the in vivo like context of an organotypic three-dimensional (3D) culture system, the cells formed a high-grade dysplastic epithelium with malignant cells invading into the stromal extracellular matrix (ECM). The invasive phenotype was in part modulated by the activation of matrix metalloproteinase-9 (MMP-9). Using pharmacological and genetic approaches to decrease MMP-9, invasion into the underlying ECM could be suppressed. In addition, tumor differentiation was influenced by the type of fibroblasts within the stromal ECM. To that end, fetal esophageal fibroblasts (FEFs) fostered a microenvironment conducive to poorly-differentiated invading tumor cells, whereas fetal skin fibroblasts (FSFs) supported a well-differentiated tumor as illustrated by keratin "pearl" formation, a hallmark feature of well-differentiated squamous cell cancers. When inducible AKT was introduced into fetal skin esophageal fibroblasts, a more invasive less-differentiated esophageal cancer phenotype was achieved. Invasion into the stromal ECM was attenuated by genetic knockdown of AKT1 as well as AKT2.

Thus, in accordance with the present invention an organotypic culture based system and screening method are provided. While the methods described herein can be extrapolated to other cancer types, a well characterized three dimensional cellular model which recapitulates esophageal cancer is described herein which will assist in the identification of agents have efficacy against this disease.

Due to the limitations of the ability to design effective screening tools, individualized therapy has been difficult to achieve using the culture methods currently available. The organotypic culture system described herein offers a unique opportunity to combine methodologies to accurately deliver a diagnostic screening tool to individualize a patient's cancer therapy. Upon isolation of a patient's tumor cells (and their tumor stem cells) and the tumor-associated fibroblasts in tissue culture, these cells can be utilized in the organotypic culture system provided. These cells would then be screened for their resistance and susceptibilities to various known (and potentially novel) therapeutics to assess the best therapy for their particular tumor. This has several advantages:
1) development of the most effective treatment of a particular patient's tumor to maximize the efficacy of the treatment
2) minimization of toxic side effects
3) facilitation of rapid testing of combination therapies
4) streamline assessment of treatment regimens directed at both primary and metastatic lesions from the same patient to assess the differential effects of therapies to both lesions
5) a means for testing of novel compounds on patients who fail remission and have traditional therapy-resistant tumors
6) extrapolatable to a wide array of tumor types including (but not limited to): esophagus, lung, skin (including melanoma), colon, breast, cervical and head and neck cancers.

Insofar as is known, drug testing has not been done to date in 3D models. Information and insights gained will guide future human clinical trials. To that end, we describe multi-well plate assays (e.g., 384 wells) plates to test compounds that specifically impair tumor cell migration and invasion for the tumors noted above. For example, bioluminescence assays would be employed in each well as read outs for tumor cell migration and invasion. Identification of agents which disrupt tumor progression before metastases develop is particularly desirable as prognosis is poor when metastases develop regardless of the site of cancer origin. A combinatorial chemistry approach will be employed to identify molecules with greatest activity and then iterations of these molecules will be developed for further cycles of screening. These assays should facilitate identification of therapeutic agents for their ability to modulate tumor cell migration and invasion. Such agents include, without limitation, nucleic acids, polypeptides, small molecule compounds, peptidomimetics. Anti-mitotic and cytotoxic drugs conventionally utilized to treat hyperproliferative disorders can also be tested in the organotypic culture system described herein, thereby facilitating characterization of combinations of drugs that inhibit tumor cell migration. In certain embodiments, candidate agents can be screened from large libraries of synthetic or natural compounds. Such compound libraries are commercially available from a number of companies, including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, they can be formulated into pharmaceutical compositions and utilized for the treatment of malignant disease.

A second application of the 3D organotypic cultures of the invention would be in the development of diagnostics. For example, 1. Provision of 3D culture (organotypic culture) from epithelial cancers of different cellular origin, e.g., esophagus, cervical, ovarian, breast, head/neck, prostate, lung), expressing the oncogenes, and/or lacking the tumor suppressor genes described herein, and assembling a genetic signature of markers which are associated with tumor migration and invasion in each particular cancer type.
2. Provision of 3D organotypic cultures from individual patients to identify genetic signatures in patients being treated, thereby formulating the most effective protocol for cancer therapy.

Definitions:

The phrase "3D organotypic culture" as used herein refers to a three dimensional culture system which recapitulates the epithelium and surrounding stroma and when transduced with activated oncogenes and inactivated tumor suppressor genes phenocopies human cancer. Methods for producing such cultures are provided below.

The terms "compound and agent" are used interchangeably herein to refer to small molecules, pharmaceuticals, nucleic acid molecules (e.g., siRNA, shRNA, miRNA, antisense) or any substance which modulates a particular biochemical pathway or phenotypic process.

The term "activated oncogene" includes, without limitation, EGFR and related family members, ras and related family members, myc and related family members, cyclin D1, CDK4, and CDK 6.

The term "inactivated tumor suppressor gene" refers to p53 and mutants thereof p16, p120, BRCA1, BRCA2, components of the notch signaling pathway, components of the hedgehog signaling pathway and components of the wnt signaling pathway.

The phrase "extra cellular matrix (ECM)" refers to the extracellular part of animal tissue that usually provides structural support to the cells in addition to performing various other important functions. The extracellular matrix is the defining feature of connective tissue in animals. Extracellular matrix includes the interstitial matrix and the basement membrane. Interstitial matrix is present between various cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest.

The phrase "cellular migration and invasive process altering agent" refers to agents which include, without limitation small molecules or inhibitory nucleic acid molecules that interfere with the function of MMP-9 or AKT, thereby inhibiting tumor cell migration and invasion.

"Fibroblasts" can be obtained from many sources which include, without limitation, human adult fibroblasts, human fetal fibroblasts (which may be obtained from the same or a different tissue source from which the keratinocytes are obtained), human fetal skin fibroblasts and fibroblast stem cells. In a preferred embodiment of the invention, the fibroblasts and keratinocytes will be obtained from the same tissue source. The phrase "activated fibroblast" is used to refer to fibroblasts that are induced during tumor invasion.

A "genetic signature" indicative of increased likelihood of tumor invasion and migration, refers to a subset of biomarkers which are differentially expressed as a tumor begins to migrate and invade adjacent tissues. Exemplary biomarkers include those listed in Table 1 and in Table 2.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, infection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "reporter gene" refers to a nucleic acid sequence which encodes a readily assayable protein. Reporter genes include without limitation, green fluorescent protein, yellow fluorescent protein, luciferase, chloramphenicol acetyl transferase or any other signal producing protein moiety.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

The following materials and methods are provided to facilitate the practice of the example below.

Cell Culture

Primary human esophageal keratinocytes, designated as EPC2, were established as described previously (Andl et al. 2003) infra. Cells were maintained at 37° C. and 5% $CO_2$ using keratinocyte-SFM medium (KSFM) (Invitrogen, Carlsbad, Calif., USA) supplemented with 40 µg/ml bovine pituitary extract (Invitrogen), 1.0 ng/ml EGF (Invitrogen), 100 units/ml penicillin and 100 µg/ml streptomycin (Invitrogen). TE12 cells, an established esophageal squamous cancer cell line, were cultured under standard conditions as described previously (Okano et al. 2000). For EGFR phosphorylation studies, cells were starved overnight in keratinocyte basal medium (KBM) that does not contain EGF, (Cambrex Bio Science, Walkersville, Md.) followed by stimulation with EGF (10 ng/ml).

Antibodies

The antibody against EGFR (Ab-12) used for immunoblotting was obtained from NeoMarkers (Fremont, Calif.). The EGFR (SC-03) antibody used for immunohistochemistry was obtained from Santa Cruz Biotechnology Inc. (Santa Cruz, Calif.). The antibodies against phospho-EGFR (Tyr845, Tyr1045, Tyr1068, and 1173), phospho-Akt (Ser 473 and Thr 308) and total-AKT were purchased from Cell Signaling (Beverly, Mass.). The MMP-9 antibody was purchased from Chemicon International Inc. (Temecula, Calif.). The monoclonal antibody against p53 (Ab-6) was obtained from Oncogene Research Products (Cambridge, Mass.) and for immunohistochemistry a p53 (DO7) antibody was purchased from Vector Laboratories (Burlingame, Calif.). The mouse monoclonal anti-E-cadherin was from Transduction Labs (Franklin Lakes, N.J.), the chicken anti-vimentin was from Novus Biologicals (Littleton, Colo.). Control anti-β-actin antibody was purchased from Sigma (St Louis, Mo.). Anti-mouse and anti-rabbit horseradish peroxidase (HRP)-conjugated antibodies were purchased from Amersham Pharmacia Biotech (Piscataway, N.J.). Biotinylated anti-chicken was detected with an ABC kit (Vector). Met antibody (C-28) Santa Cruz Biotechnology (Santa Cruz, Calif.), p53 (Ab-6) Calbiochem (Gibbstown, N.J.), alpha-smooth muscle actin (1A4) Sigma, and GAPDH Chemicon/Millipore (Billerica, A). Recombinant human HGF was purchased from R&D Systems (Minneapolis, Minn.). PHA665752 was obtained from Tocris Bioscience (Ellsville, Mo.). 2B8 (mouse anti-human HGF IgG1 generated from hybridoma) was obtained from AVEO Pharmaceuticals (Cambridge, Mass.). Mouse IgG1 control antibody was obtained from R&D Systems. Rabbit polyclonal periostin (Abcam, ab 14041), p21 (Oncogene Research Products), WAF1 (ab-1), were also used. β-actin (Sigma) was used as a loading control. For immunohistochemistry periostin antibody was obtained from Abcam, ab 14041.

Western Blotting

For Western blot analysis, cells were lysed in lysis buffer (10 mM Tris.HCl, pH 7.4, 150 mM NaCl, 1% Nonidet P-40, 0.1% sodium deoxycholate, 0.1% SDS, 1 mM EDTA, 2 mM sodium orthovanadate and a protease inhibitor tablet, Roche Molecular Biochemicals, Indianapolis, Ind.). Protein concentration was determined by the Bio-Rad protein assay (Bio-Rad, Hercules, Calif.). 15 µg of protein were run on a 4-12% SDS-PAGEgel (Invitrogen) and transferred to a polyvinylidene difluoride membrane (Immobilon-P, Millipore, Bedford, Mass.). Membranes were blocked in 5% nonfat milk (Bio-Rad) in TBS-T (10 mM Tris, 150 mM NaCl, pH 8.0 and 0.1% Tween® 20) for 1 h at Room temperature. Membranes were then probed with primary antibody diluted in 5% milk in TBS-T overnight at 4° C., washed with TBS-T and incubated with anti-mouse or anti-rabbit horseradish peroxidase-conjugated secondary antibodies (GE Biotech, 1:3000 in TBS-T) for 1 h at room temperature and washed in TBS-T. The signal was visualized using an enhanced chemiluminescence solution (ECL Plus, Amersham Pharmacia Biotech) and exposed to Blue Lite Autorad film (ISC-BioExpress, Kaysville, Utah). To confirm secreted periostin expression, conditioned media was collected and protein concentration was determined by Bio-Rad protein assay (Bio-Rad) and Western blot analysis was performed as described above.

ShRNA and SiRNA Constructs for MMP-9, AKT1 and AKT2

Human retroviral shRNAmir against MMP-9, AKT1 and AKT2 and Expression Arrest™ eGFP control shRNA vector as a control, were purchased from Open Biosystems (Huntsville, Ala.). The control siRNAs and siRNAs specific for human AKT1 and AKT2 (validated siRNA) and MMP-9 were purchased from Ambion (Austin, Tex.). Cells were transfected with a cationic lipid (LipofectAMINE™ 2000, Invitrogen, Carlsbad, Calif.) according to the manufacturer's protocols. The effectiveness of knockdown was confirmed by Western blotting with specific antibodies. SiRNA molecules which are effective to down regulate expression for most known nucleic acid sequences are commercially available from Dharmacon.

Genetic Knockdown of Met and Overexpression Studies.

Human lentiviral shRNAmir against Met (shMet clone V2HS_76544) and non-silencing control shRNAmir retroviral vector (shScramble) were purchased from Open Biosystems (Huntsville, Ala.). Human pBABE-TPR-Met and pBABE-HGF were purchased from Addgene (Cambridge, Mass.). Two different Silencer® Select Pre-designed siRNA targeting HGF (siHGFs: siRNA ID #s6529, siHGF3: siRNA ID #s6530) were purchased from Applied Biosytems along with the Silencer® Select Negative Control #1 siRNA (si-Control) (Austin, Tex.). For HGF knockdown studies, early passage fibroblasts were transfected with 10 nM siRNA the day before embedding in organotypic culture matrix using Lipofectamine™ 2000 (Invitrogen) following the manufacturers' recommendations. For HGF overexpression, early passage fibroblasts were infected with pBABE-HGF or pBABE-puro. Overexpression cells were selected for using puromycin (0.5 µg/mL) for more than 72 hours. Overexpression and knockdown of HGF secretion was monitored by ELISA. EPC-hTERT-EGFR-p53$^{R175H}$ cells were infected with pGIPZ-shMet or pSM2c-shScramble. Cells were selected for with puromycin (shScramble) or by flow cytometry cell sorting for GFP (shMet) on a FACSVantage™ SE with FACSDiVa™ Option (BD Biosciences). Met knockdown was monitored by Western blot. EPC-hTERT-p53$^{R175H}$-neo, EPC-hTERT-EGFR-zeo, and EPC-hTERT-neo-zeo cells were infected with pBABE-TPR-Met and pBABE-puro. Cells were selected for with puromycin as above and overexpression monitored by Western blot.

Retroviral Vectors and Stable Transduction

Stable transduction of primary esophageal cells with retroviral vectors was described previously (Andl et al. (2003) J. Biol. Chem 278:1824-1830; Harada et al. (2003) Mol. Cancer Res. 1:729-738; Takaoka et al. (2004) Oncogene 23:6760-6768). Briefly, the pFB-neo retroviral vector (Stratagene, La Jolla, Calif.) containing the entire coding sequence for the human EGFR (pFB-neo-WT-hEGFR) or pBabe-zeo-p53$^{R175H}$ or pBabe-puro-p53$^{R175H}$ were transfected into Phoenix-Ampho packaging cells (gift of Dr. Garry Nolan, Stanford University, Palo Alto, Calif.) using LipofectAMINE™ 2000 reagent (Invitrogen), according to manufacturer's instructions. Similar procedures were used for the p53$^{V143A}$, p53$^{R248W}$, and p53$^{R273H}$ mutants. Culture supernatants from individual Phoenix-Ampho cells were used to infect to EPC2-hTERT cells. Cells were passaged 48 hours after infection and selected with G418 (300 µg/ml), puromycin (0.5µg/ml) or zeocin (10 µg/ml) (Invitrogen) for a period of 7 days, resulting in generation of control EPC2-hTERT-neo-zeo or EPC2-hTERT-neo-puro, EPC2-hTERT-neo-p53 neo-p53 EPC2-hTERT-EGFR-zeo or EPC2-hTERT-EGFR-puro, and EPC2-hTERT-EGFR-p53$^{R175H}$ cells. Independent infections and selections were performed to generate two additional cell lines of each genotype.

The retroviral vector pWZLneo was used to express the conditionally active AKT construct myrAKT Δ4-129-ER (myrAKTER) (Kohn et al. (1998) J. Biol. Chem 273:11937-11943). This myristolated AKT, fused to the estrogen receptor, permits constitutive localization to the cell membrane with activation induced by tamoxifen addition to the culture medium resulting in the activation of ectopically expressed AKT.

For experiments assessing periostin's role in the tumor microenvironment periostin cDNA was used (Open Biosystems) and subcloned into the pFBneo retroviral vector. Two periostin short hairpin RNAs (shRNA#1 5'-CCCATG-GAGAGCCAATTAT-3'and shRNA#2 5'-CTCTGACA TCATGACAACAAAT-3') were used (Open Biosystems). For all virus production, plasmids were transfected into Phoenix-Ampho packaging cells (gift of G. Nolan) using Lipofectamine™ 2000 reagent (Invitrogen). Supernatants of the retroviruses encoding EGFR, mutant p53, periostin over-expression and shRNA vector constructs were collected 48 hrs. and 72 hrs. after transfection. For retrovirus infection, 30% confluent EPC-hTERT cells were infected with retrovirus supernatant in the presence of 4mg/ml polybrene (Sigma). 48 hours after infection, cells were selected in 300 µg/ml G418, 0.5 µg/ml puromycin, 2 mg/ml zeocin or 5 mg/ml blastocidin for 5 days. Overexpression of EGFR, mutant p53 and periostin, as well as periostin knock-down was confirmed by Western blot analysis.

qPCR

LCM was repeated to isolate invading and non-invading EPC-hTERT-EGFR-p53$^{R175H}$ cells grown in organotypic culture. Amplification and cDNA synthesis was performed using WT-Ovation™ RNA Amplification System (NuGen Technologies) according to manufacturer's instructions. Real-Time PCR was performed and analyzed using ABI PRISM® 7000 sequence detection system software (PE Applied Biosystems) and using Power SYBR® Green PCR Master Mix (PE Applied Biosystems) for β-actin according to the manufacturer's instructions. Taqman® assays for periostin were run using Taqman® Universal PCR Master Mix (PE Applied Biosystems) according to manufacturer's instructions.

Tumor Specimens

Esophageal tumor tissue specimens and adjacent normal tissue were surgically procured from patients at the Okayama University Hospital (Drs. Shirakawa and Naomoto, Japan). All tumor specimens were pathologically diagnosed as esophageal squamous cell carcinomas (Grade III). All of the clinical materials were obtained from informed-consent patients in accordance with Institutional Review Board standards and guidelines.

Specimens were immediately snap-frozen for RNA and protein analyses. Human ESCC tissue microarray was purchased from Tissue Array Network for immunohistochemistry analysis using polyclonal anti-periostin antibody and scored for periostin expression as follows; Negative (0), Marginal considered negative (0.5), mild positive stain (1), moderate positive stain (2), and intense positive stain (3). Scores>0.5 are considered positive. Each case on the tissue microarray comprises of 2 cores and the mean scores of 2 cores were taken.

Migration and Invasion Assays

For migration assays, Boyden chambers (8 µm pore size, FluoroBlok™-HTS inserts, BD Biosciences) were used. For invasion assays, insert-plates (8 µm pore size, FluoroBlock™, 24 well insert) coated with BD Matrigel® matrix were used. Inserts were placed in a 24-well plate containing Full KSFM medium with serum to stimulate cell migration and invasion. $5 \times 10^4$ cells in serum-free medium were placed in each insert. Twenty-four hours later, migrating or invading cells were labeled with 4 µg/ml Calcein AM dye (Invitrogen) in HANKS buffer for 1 hour. The labeled cells were then read on A Synergy HT multi-detection microplate reader (BIOTEK, Woburn, Mass.) at 485 nm excitation and 528 nm detection. All experiments were performed in triplicate in three independent cell lines for each genotype.

Fibroblast Isolation and Characterization

For fibroblast isolation, tissues were washed four times with sterile DMEM with antibiotics (20% FBS, 0.25% gentamycin, 0.1% Fungizone). Tissues were then cut lengthwise under sterile conditions, mixed with dispase and incubated overnight in 50 ml conical tubes with slow shaking at 4° C. The dermis or esophageal submucosa were then carefully peeled away from the epidermis or mucosa, respectively. The dermis or esophageal submucosa were then placed in 0.5% trypsin for 10 min at 37° C. followed by washing with 5× volume of 250 mg/L soybean trypsin inhibitor. Individual cells were then collected and washed in medium containing antibiotics and placed in 10% DMEM. To verify the purity of the fibroblasts, western blotting was performed to confirm that cells were vitmentin positive and E-cadherin negative. Functionally, the fibroblasts are tested to for the ability to induce constriction of the extracellular matrix in organotypic culture.

Organotypic Culture

To grow human esophageal epithelial cells (keratinocytes) in organotypic culture, 3D collagen/Matrigel® matrices, containing 76.7% bovine tendon acid-extracted collagen (Organogenesis, Canton, Mass.), Matrigel® Matrix (BD Bioscience), 1× minimal essential medium with Earle's salts (BioWhittaker, Walkersville, Md.), 1.68 mM L-glutamine (Cellgro, Herndon, Va.), 10% fetal bovine serum (Hyclone, Logan, Utah), 0.15% sodium bicarbonate (Bio Whittaker), and $7.5 \times 10^4$ human fetal or adult esophageal fibroblasts, or human fetal skin fibroblasts were generated. These matrices were allowed to contract for 7 days at which point $5 \times 10^5$ human esophageal epithelial cells were seeded on top of the matrices. Following addition of keratinocytes, cultures were fed with Epidermalization I medium for 2 days, which is Dulbecco's modified Eagle's medium (JRH Biosciences, Lenexa, Kans.)/Ham's F-12 (Invitrogen) (3:1) supplemented with 4 mM L-glutamine, 0.5 µg/ml hydrocortisone, 0.1 mM O-phosphorylethanolamine, 20 pM triiodothyronine, 0.18 mM adenine, 1.88 mM CaCl2, 4 pM progesterone (Sigma); 10 µg/ml insulin, 10 µg/ml transferrin, 5 mM ethanolamine, 10 ng/ml selenium (ITES) (Bio Whittaker); and 0.1% chelated newborn calf serum (Hyclone). For the following 2 days, cultures were fed with Epidermalization II medium, which is identical to Epidermalization I medium except it contains 0.1% un-chelated newborn calf serum (instead of chelated). Then, cultures were raised to an air-liquid interface and cultured in Epidermalization III medium, containing the same growth supplements as Epidermalization I and II except no progesterone is added and 2% newborn calf serum is used, for 6 days. Cultures were then harvested by fixing in 10% formaldehyde (Fisher, Pittsburg, Pa.) and later paraffin embedded. Conditioned medium was also collected at the time of harvesting.

Pharmacological MMP-9 and AKT Inhibition

For MMP-9 inhibition studies, an MMP-9 inhibitor purchased from EMD Biosciences (San Diego, Calif.) was used. (Catalog number: 444278) The MMP-9 inhibitor is a potent and selective inhibitor of MMP-9 (IC50=5 nM). It inhibits MMP-1 at IC50=1.05 µM. This inhibitor complexes with the zinc cofactor that is required to keep MMP-9 in an active state (Levin et al. (2001) Bioorg. Med. Chem. Lett. 11:2189-2192). The MMP-9 inhibitor was added to the Epidermalization III medium (beginning at day 11) in increasing doses from 0.5 nM to 500 nM. AKT inhibition in organotypic cultures was performed using the AKTi 1/2 inhibitor purchased from Calbiochem (San Diego, Calif.). (Catalog number: 124018 AKTi 1/2 is a cell-permeable, potent and selective inhibitor of Akt1/Akt2 activity (IC50=58 nm, 210 nM, and 2.12 uM for AKT1, AKT2 and AKT3, respectively, in in vitro kinase assays). The inhibition is reported to be pleckstrin homology (PH) domain-dependent. To specifically target the fibroblasts, the AKTi 1/2 ihibitor (50 nM) was added to the media during the period of matrix contraction and prior to the addition of epithelial cells (days 1-7).

Real-time PCR

RNA was isolated from cells using Trizol reagent (Invitrogen), and cDNA was synthesized using the Superscript® first strand synthesis system for RT-PCR (Invitrogen) according to the manufacturer's instructions. Primers for SYBR® green real time PCR were designed using the TaqMan® probe software and synthesized by Invitrogen. The following oligonucleotides were used as primers; a)human MMP-9 5'-GGA CGA TGC CTG CAA CGT-3'(forward primer; SEQ ID NO: 1); 5'-ACA AAT ACA OCT GGT TCC CAA TC-3'(reverse primer; SEQ ID NO: 2), b) human glyceraldehydes-3-phosphade dehydrogenase (GAPDH) 5'-CAC CCA CTC CTC CAC CTT T-3'(forward primer; SEQ ID NO: 3); 5'-TCC ACC ACC CTG TTG CTG TAG-3'(reverse primer; SEQ ID NO: 4). GAPDH was used as internal control. SYBR® green real time PCR was performed and analyzed using ABI PRISM® 7000 sequence detection system software (PE Applied Biosystems, Foster City, Calif.) with reagents from the SYBR® green PCR kit (PE Applied Biosystems) according to manufacturer's instruction.

Immunohistochemistry

Immunohistochemistry was performed with the Vecta Elite kit (Vector Laboratories, Burlingame, Calif.) following the manufacturer's protocol. Briefly, paraffin sections were pretreated with xylene and then microwaved for 10 min in the presence of 10 mM citric acid buffer. Endogenous peroxidases were quenched using hydrogen peroxide before sections were blocked in avidin D blocking reagent and biotin blocking reagent. Sections were incubated with primary antibody overnight at 4° C. and secondary antibody for 30 min. at 37° C., and then signal was developed using the DAB substrate kit for peroxidase (Vector Laboratories). For tumor microarray (TMA) analysis in the HGF studies, 73 paired paraffin blocks representing tumors containing esophageal squamous cell cancer as well as squamous dysplasia and the corresponding adjacent normal mucosa were provided us by Dr. Michiyuki Kanai at Kitano Hospital (Osaka, Japan). All of the clinical materials were procured via surgery from informed-consented Japanese patients (62 male and 13 female) in accordance with Institutional Review Board (IRB) standards and guidelines. We constructed four TMAs of paired normal esophageal mucosa and tumor (SCC) from 73 patients (totaling 292 cores, each patient was represented by 4 cores, 2 normal mucosa and 2 SCC cores). Antibody staining was done following standard protocols that have been described previously (5). To score the Met staining of tumor microarrays, the slides were evaluated by an expert pathologist using the following scale: 0.5 is marginal, 1=moderate, 2=intense staining.

Zymography

Gelatin zymography was performed on 10% Novex precast polyacrylamide gel (Invitrogen) in the presence of 0.1% gelatin. Conditioned media (20 µl) were loaded and SDS-PAGE was performed using tris-glycine SDS buffer. Protein standards were run concurrently and approximate molecular weights were determined. Protein content was assayed by the method of Bradford and samples were mixed with equal volume of 2× SDS sample buffer (Invitrogen, Carlsbad, Calif.). Samples were incubated at room temperature for 15 min and were applied to gelatin or casein zymography gels. After electrophoresis (125 V, 90 min) proteins were renatured within zymography renaturing buffer (Invitrogen) for 30 min at room temperature under continuous shaking conditions and were then placed at 37° C. overnight in developing buffer (Invitrogen). Substrate was visualized by Coomassie brilliant blue staining (0.1% Coomassie brilliant blue, 45.5% methanol, 9% acetic acid).

MMP-9 Activity Assay

Conditioned media of organotypic cultures were collected on day 15, centrifuged at 10K×g at 4° C. and 100 ul was used to detect MMP-9 enzymatic activity in duplicate using the SenzoLyte® Plus MMP-9 assay kit from Anaspec (San Jose, Calif.) according to the manufacturer's instructions. In brief, a specific MMP-9 antibody was used in combination with an MMP-9 fluorogenic substrate 5-FAM/QXL™ 520. In addition, 1 mM p-Aminophenylmercuric Acetate (AMPA) was used to activate a pro-MMP-9 standard and pro-MMP-9 in samples. Fluorescent signal was monitored at Excitation/Emission=490-520 nm upon MMP-9 induced cleavage of the QXL™ FRET substrate using a fluorescence microplate reader Bio-Tek FLx800 (Richmond, Va.).

Extracellular Matrix Stiffness Measurements

Stiffness of 3D organotypic culture ECMs was assessed by measuring the dynamic shear modulus (G') with a Rheometrics RFS-II instrument using cone-and-plate geometry with titanium surfaces. The cone had a diameter of 8 mm. Cut-outs of extracellular matrix of 8 mm in diameter and 1.7 mm-4.0 mm in thickness were measured by a strain controlled dynamic sweep test. Time-dependent measurements were done for 150 s with one time point every 15 s at 5 rad/s and 2.0% strain. An average of all measurements was then calculated. All samples were tested in triplicate.

Soft Agar Colony Formation Assays

To assess anchorage independent growth in soft agar, cells were suspended in 0.67% agarose containing DMEM-KBM (1:1) medium supplemented with 5% FCS, 30 µg/ml BPE, and 0.5 ng/ml EGF, overlaid on top of a 1% agarose containing the medium ($2.5 \times 10^4$ cells per well), and allowed to form colonies for two weeks at 37° C. under 5% $CO_2$. Colonies were counted under an Eclipse TS100 inverted microscope (Nikon, Melville, N.Y.).

Laser Capture Microdissection

Laser capture microdissection (LCM) was used to isolate invading cells and control non-invading cells followed by microarray analysis. For these studies, frozen organotypic cultures performed in triplicate for all cell genotypes were sectioned to 8 µm onto membrane mounted metal frame slides (MMI, Switzerland) using a Microm HM 505E cryostat (Richard Allen Scientific, Kalamazoo) located in the Morphology Core. One at a time, sections were be fixed, stained and dehydrated (75% ethanol, DEPC-water, hematoxylin, DEPC-water, 95% ethanol, 100% ethanol, xylene) before laser capture microdissection. LCM was performed with a Nikon Eclipse TE 2000-5 microscope with a UV laser (MMI, Switzerland) also located in the Morphology Core. RNA was obtained from the LCM experiments using the Arcturus PicoPure RNA isolation kit, amplified at the Penn Microarray Facility using the Affymetrix GeneChip Expression 3'-Amplification Two-Cycle cDNA Synthesis Kit and used on Affymetrix U133Plus 2.0 oligonucleotide microarrays. Affymetrix Microarray Suite 5.0 was used to quantitate mRNA expression levels.

Primary analysis of data obtained from the microarray studies was performed. These genes provide new targets for therapy. Expression changes of all genes obtained from the microarray studies will be validated by quantitative real-time PCR analysis. The protein expression of candidate genes will also be assessed by Western blot analysis and localized in the organotypic cultures by immunohistochemistry.

Data Processing

Affymetrix array cel files were processed in R using an algorithm that uses genes in the least variant set (LVS) to normalize the expression data (31). In the analysis of invasive and non-invasive cells, we then identified 6106 probe sets for subsequent statistical analysis that had a minimum expression level (expression greater than 100 in all samples) and that had significant variability among the 11 cell lines (standard deviation was greater than 150). The background correction, summarization and normalization of Affymetrix cel files were done in the same manner independently for each of the two tumor/normal studies. Gene Expression Omnibus (GEO) database accession number: GSE21293

Statistical Analysis

All statistical analyses used natural log transformed expression data. Using the arrays of cells from the organotypic culture model, a multivariate regression model was fit for each gene that included two independent binary variables. The first variable indicated cells with both EGFR overexpression and P53 mutation only and the second indicated cells with EGFR overexpression, P53 mutation and invasion. The third group (the reference group) included cells with a non-invading phenotype that had either EGFR overexpression or P53 mutation. The p-values from the test that the regression model was significant (F-statistic, 2df) were adjusted using the Benjamini-Hochberg technique; probe sets with a False Discovery Rate (FDR)<0.05 were selected for further investigation (32). Genes on this list were compared to annotated Gene Ontology biologic processes and a functional annotation cluster analysis was done using the online DAVID tool (niaid.abcc.ncifcrf.gov/). Annotations were derived from the DAVID databases. Supervised hierarchical clustering used in the heat maps was based on Euclidean distance. The statistical analyses were done using SAS/STAT software version 9.2 of the SAS System for PC.

The following examples are provided to illustrate certain embodiments of the invention. They are not intended to limit the invention in any way.

EXAMPLE I

Esophageal cancer is common and represents the fifth most frequent cancer in males worldwide. The American Cancer Society estimates that in the United States about 14,500 new cases of esophageal cancer will be diagnosed annually and approximately 13,700 deaths will occur from esophageal cancer in 2008. Given the poor survival rate, advanced stage of the disease at diagnosis and the increasing frequency of the disease, it is essential to understand the molecular mechanisms underlying the initiation of these tumors and the basis of their invasion into the extracellular matrix (ECM) and ultimate metastasis. The data presented herein show that the interplay of the EGFR oncogene with the dysregulation of the p53 and p120-catenin (p120ctn) tumor suppressor genes alters the tumorigenic potential of esophageal cells, thereby resulting in increased cell migration and invasion. Data showing that changes in the mesenchymal compartment of the esophagus occur during tumorigenesis whereby tumor activated fibroblasts interact in a paracrine manner to induce increased esophageal tumor cell migration and invasion is also disclosed. These studies reveal the genetic signatures that mediate tumor cell migration and invasion and to elucidate how stromagenesis (activation of mesenchymal stromal fibroblasts) affects epithelial mediated tumorigenesis. This information provides viable targets for combinatorial therapy of esophageal cancer with clear applications to other squamous cancers (e.g., skin, head/neck, lung, cervical, and, anogenital).

Oncogenes in Esophageal Cancer

Figure 1:
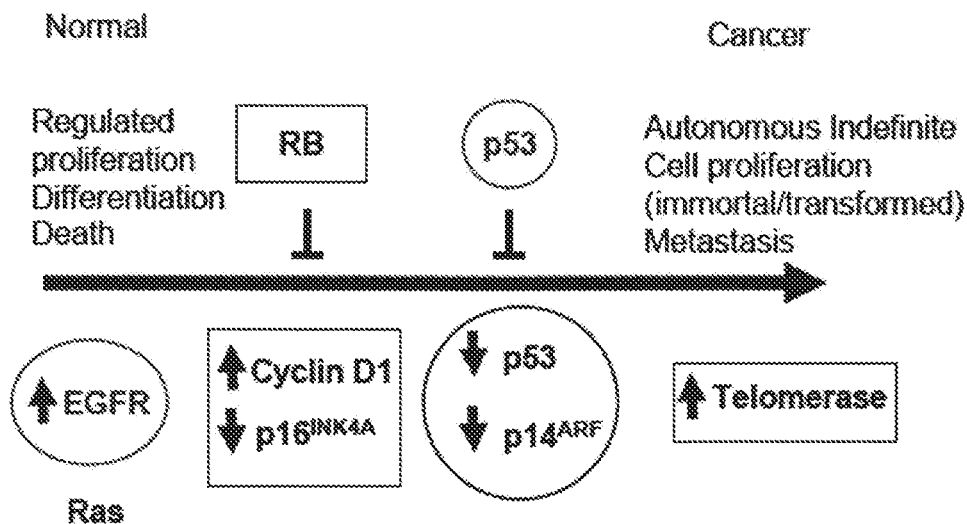
FIG. 1 is a schematic diagram of genetic pathways in esophageal squamous cell carcinogenesis.

Several classic oncogenes and tumor suppressor genes have been associated with ESCC (FIG. 1). EGFR and cyclin D1 are both commonly overexpressed or activated in ESCC and thought to be early events in the development of these tumors. In the adult esophagus, EGFR is localized to the basal and suprabasal layers and little or no receptor is found in the surface epithelium. EGFR over-expression and amplification have been detected as well as the over-expression of one of its ligands, transforming growth factor (TGF)-alpha. Additionally, EGFR over-expression is correlated with poor prognosis. EGFR over-expression is felt to be an early or initiating event in esophageal squamous carcinogenesis. Likewise, cyclin D1 over-expression and amplification have been detected in both tumor types as well as their precursor lesions. Studies have determined that 16-36% of tumors have amplified the gene and 29-75% harbor overexpression of the protein.

p53 Function and Mutations p53 is a tetrameric multidomain transcription factor that plays an important role in genome stability. This transcription factor activates a number of genes in response to cellular stresses including DNA damage, UV irradiation and hypoxia. The genes activated by p53 encode proteins responsible for G1 and G2 cycle arrest and apoptosis. p53 is one of the most commonly mutated genes in human cancer. This tumor suppressor plays an important role in suppressing oncogenic transformation by interrupting the G1 phase of the cell cycle to assess and allow for repair of damaged DNA. If damage is irreparable, p53 induces apoptosis. p53 mutation results in unsuccessful cell cycle checkpoints and completion of mitosis with damaged DNA giving rise to aberrant daughter cells. p53 binds DNA at a specific p53-binding site (PBS) to activate or suppress a large number of target genes (Sengtpta et al., (2005) Nat. Rev. Mol. Cell Biol 6:44-55). The majority of p53 mutations occur in the DNA-binding domain and over 80% of these mutation are missense mutations leading to a dominant negative-effect resulting in loss of function of wild-type p53 (Sengupta et al., supra). Six hot spot sites in the DNA binding domain are most frequently mutated in human cancers ($Arg^{175}$, $Gly^{245}$, $Arg^{248}$, $Arg^{273}$ and $Arg^{282}$) (Joerger et al., (2005) J. Biol Chem. 280:16030-7)). We analyzed the activity of mutations in three of these sites, $Arg^{175}$, $Arg^{248}$ and $Arg^{273}$ and an additional site $Val^{143}$. All of the mutants used in these studies carry missense mutations that abrogate protein-DNA contact either by disrupting the protein conformation (V143A and R175H) or disrupting the DNA-binding surface (R248W and R273H). Mutations R175H, R248W and R273H occur most frequently in ESCC and are considered to have growth advantages to progress to invasive squamous cell carcinoma. V143A is a temperature sensitive mutant, which has a mutant conformation at 38° C. and a wild-type conformation at 32° C. Our data indicated that p53 mutants preferentially collaborate with EGFR overexpression in the development of ESCC.

Mouse models have provided insight into the role of p53 in tumorigenesis (Parant et al. (2003) Hum Mutat 21:321-326). These models have supplied information regarding the initiation of tumors, the rate of growth and the tumor spectrum. These findings could not have been obtained with the sole use of in vitro models. Mice lacking one or both p53 alleles are predisposed to multiple tumor types, including lymphomas, sarcomas and lung tumors. However, because more than 50% of human tumors contain p53 mutations, the p53 null mice do not recapitulate the tumor incidence of p53 mutations.

To address this issue, mice containing specific missense p53 mutations have been generated. These include two models of Li-Fraumeni Syndrome (LFS) previously described. Olive et al. (2004) Cell 119: 847-60). LFS is a familial cancer predisposition syndrome characterized by p53 point mutations resulting in a number of malignancies. The LFS mouse models generated contain targeted mutations of p53 in the endogenous gene locus. One mouse model harbors a p53R172H mutation equivalent to the human R175H mutation. The second mouse contains a p53R270H mutation equivalent to the human R273H mutation. An advantage of these mouse models is that they contain a transcriptional STOP sequence flanked by LoxP sites (LSL) upstream of the mutant p53 sequence, allowing for targeted expression of the mutant protein by crossing with promoter specific Cre mice. These $p53^{LSL-R172H}$ and $p53^{LSL-R270H}$ mice provide the in vivo compliment of two of the mutations used in in vitro studies described above.

p120-Catenin as a Tumor Suppressor p120-catenin (p120ctn) defines a family of catenin proteins related to β-catenin that bind to E-cadherin in adherens junctions (Reyolds et al. (2004) Oncogene 23:7947-56)). p120ctn contains an N-terminal coiled coil domain, a regulatory domain containing most of its phosphorylation sites followed by an armadillo repeat domain containing 10 repeats. Many isoforms of p120ctn exist resulting from differential splicing. Alternative splicing at the 5' end results in the utilization of 4 different ATG start codons while three alternatively spliced exons, one in the armadillo repeat domain and two in the C-terminal region, may be included/excluded. Isoforms that utilize the first ATG start site are preferentially expressed in mesenchymal, motile cells while isoforms that utilize the third start site are expressed in epithelial, non-motile cells. Our data indicate that differential expression of p120ctn isoforms appears to regulate esophageal cell migration and invasion.

p120ctn also contains 16 different phosphorylation sites, comprising eight tyrosine and eight serine/threonine. p120ctn was initially discovered as a target for Src phosphorylation and has been demonstrated to be phosphorylated by several Src family members. Additionally, cell stimulation with many growth factors induces phosphorylation of p120ctn. Interestingly, EGFR activation induces phosphorylation of Y228, although it is unclear whether this is a direct or indirect phosphorylation event. We have also demonstrated that EGFR regulates p120ctn availability in binding E-cadherin. Given the number of phosphorylation sites and its interaction with kinases and phosphatases that likely regulate its phosphorylation, we hypothesis that p120ctn phosphorylation is likely to regulate its various functions.

Analysis of p120ctn expression in tumors has demonstrated its downregulation in colon, prostate, lung and breast cancers. Interestingly, decreased expression is not typically seen in the entire tumor but rather in regions of the tumor, similar to that seen for E-cadherin suggesting it is a late event in tumor progression (Birchmeier et al., (1995) Bioessays 17:97-98). Unlike β-catenin, p120ctn does not bind to APC. As a result, loss of E-cadherin does not always lead to a loss of p120ctn; instead it (p120ctn) is redistributed to the cytosol and nucleus. This shift in localization of p120ctn can result in increased cell motility and invasiveness by inhibiting RhoA activity and increasing Rac and cdc42. Additionally, knockdown experiments using shRNA to p120ctn have demonstrated that loss of p120ctn induces invasion. See FIG. 2. This relocalization may at least partially explain the increased metastasis in tumors that have lost E-cadherin expression and retained p120ctn.

Knockdown of p120ctn Expression.

Figure 2:
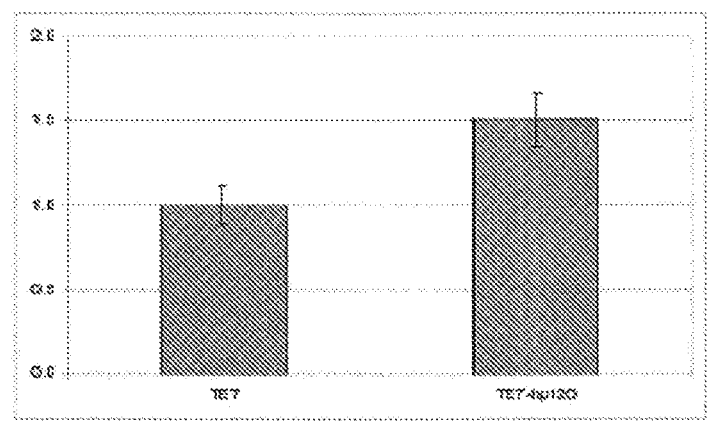
FIG. 2 shows a graph of results from migration assays of TE7 cells. Boyden chamber assay were performed on TE7 parental and the pooled shRNA1 cell line which has 80-90% knockdown of p120ctn. CalceinAM staining was performed and green fluorescent intensity of migrating cells was determined using a plate reader. Knockdown cells have 50% greater motility than the parental cells.

To verify that TE7 cell invasion is dependent upon p120ctn, we have to knockdown its expression and perform migration and invasion assays. To that end, we have used shRNAs that can specifically decrease either human or mouse p120ctn. Western analysis of these stable, pooled cell lines and independent clones demonstrate approximately 80-90% knockdown of l120ctn in the shRNA1 pooled cell line and varying amounts of knockdown in the independent dines (data not shown). Clones 1, 17 and 19 have similar p120ctn expression as the pooled cell line. Preliminary migration assays of TE7 parental cells with the shRNA1 pooled cell line demonstrate a 50% increase in motility as assayed by Boyden chamber assays, p=0.03 (FIG. 2). Control cells do not have increased invasion (data not shown).

Combination of EGFR Overexpression and p53 Inactivation in Esophageal Epithelial Cells.

Figure 3:
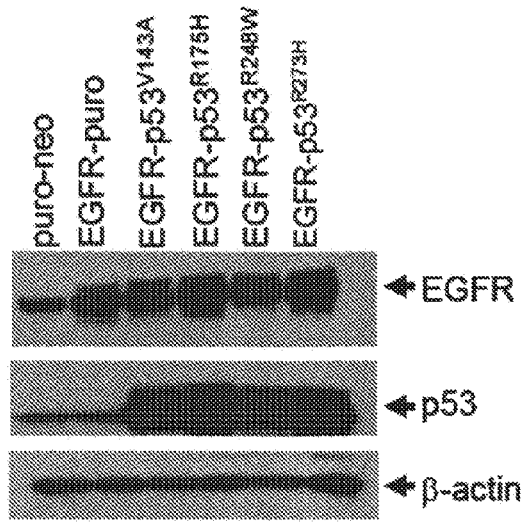
FIG. 3 is a western blot confirming generation of EPC-hTERT cells overexpressing EGFR and mutant p53 following retroviral infection. Puro is the empty vector control for mutant p53, while neo is the empty vector control for EGFR.

Esophageal primary cells (EPC) have been immortalized by over-expression of the catalytic subunit of telomerase (hTERT) (EPC-hTERT cells) (Harada et al., (2003) Mol. Can. Res. 1:729-738). EGFR and four human p53 mutants (V143A, R175H, R248W or R273H) have been over-expressed in these cells by retroviral transduction. Overexpression was confirmed by western blot analysis. Similar levels of EGFR and mutant p53 overexpression were observed between the cell lines. β-actin was used as a loading control (FIG. 3). Increased EGFR phosphorylation was also observed in cells over-expressing EGFR (data not shown), indicating that the over-expressed receptor is functional.

Increased Migration and Invasion in Organotypic Culture of EPC-hTERT Cells Overexpressing EGFR and mutant p53.

Figure 4:
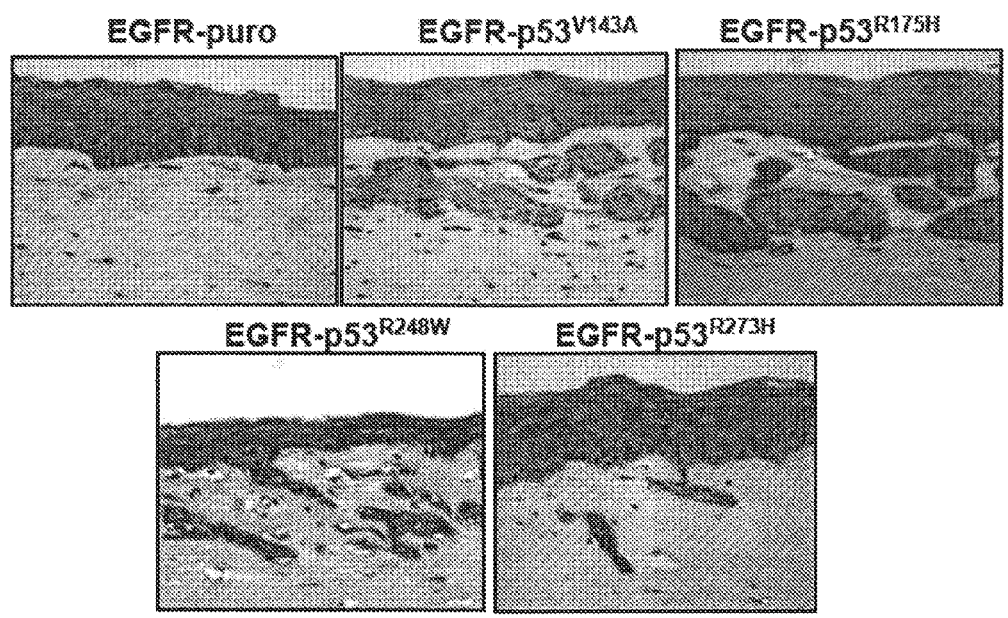
FIG. 4 is a micrograph showing invasion in organotypic culture by EPC-hTERT cells expressing EGFR alone or in combination with different p53 mutants which were tested for migration and invasion capacities.

Cells overexpressing EGFR and the different p53 mutants showed moderate to severe dysplasia in the basal layer and invasion of epithelial cells into the extracellular matrix (data not shown). Control cell lines expressing the individual p53 mutants alone did not result in invasion into the underlying matrix (data not shown), indicating that invasion results from the combinatorial effects of EGFR overexpression and p53 mutation. Interestingly, when grown in organotypic culture, differences in invasion capabilities were observed between the different p53 mutants, highlighting the value of this more physiological type of culture. The R175H and V143A mutants resulted in the greatest invasion and the R273H mutant showed the least invasion capacity. These results suggested that different p53 mutants, in combination with EGFR overexpression, yield different biological behaviors in the tumor microenvironment (FIG. 4).

Laser Capture Microdissection (LCM) and Microarray Analysis.

Figure 5:
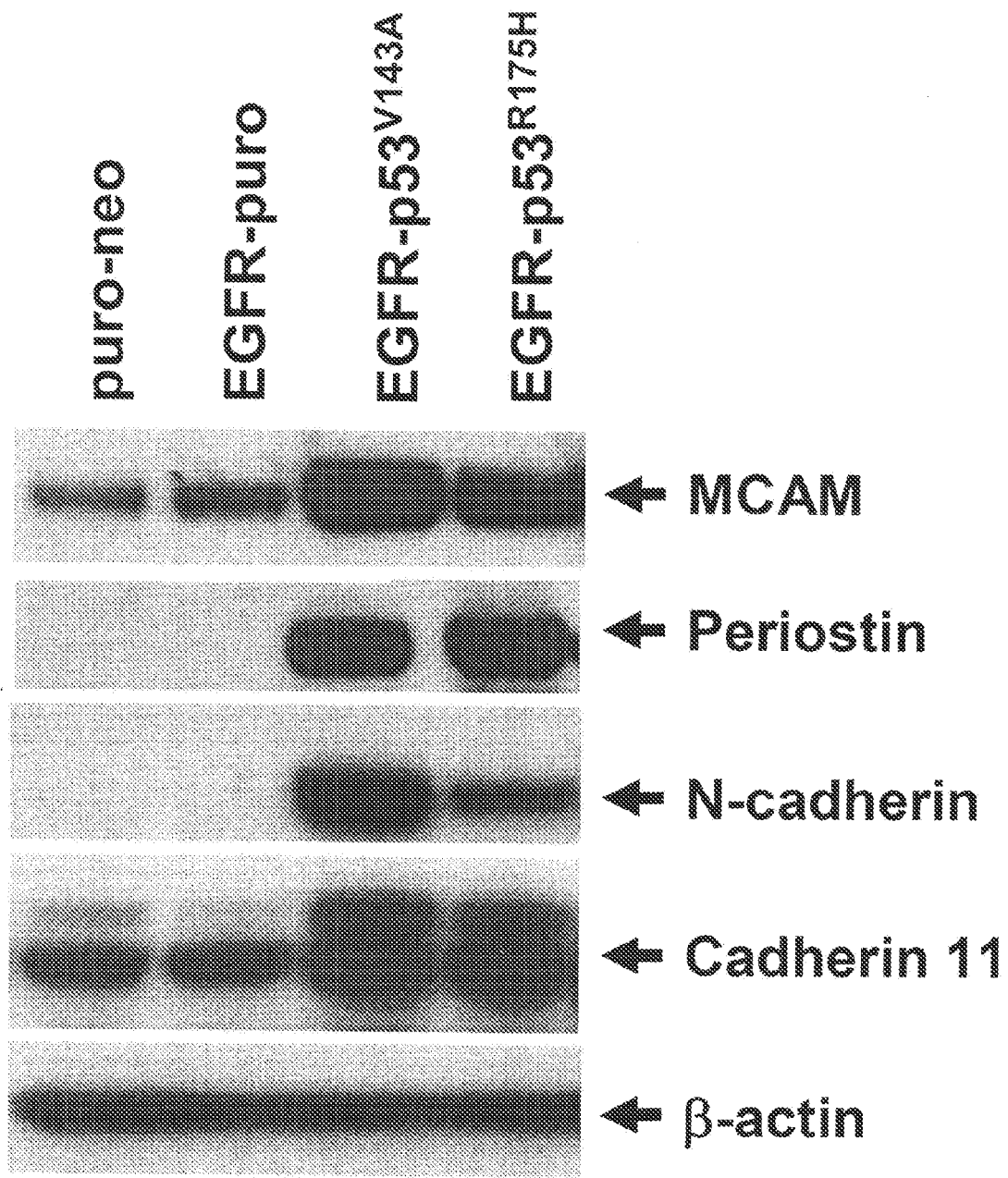
FIG. 5 is a blot showing validation of gene array results. Western immunoblots confirming increased expression of MCAM, Periostin, N-cadherin and Cadherin-11 in EPC-hTERT cells overexpressing EGFR and mutant p53.

In order to identify genes that may play a role in promoting invasion in the organotypic culture model, laser capture microdissection (LCM) was used to isolate invading cells. Cells from the normal basal layer were also microdissected from each sample to serve as control. RNA was extracted and following 2 rounds of amplification, was used for microarray analysis. Initial comparisons focused on the genetic signatures of invading vs. non-invading (normal control) cells within the same cell genotype. Table 1 depicts key cell adhesion genes found to be deregulated in invading EPC-hTERT-EGFR-$p53^{R175H}$ cells (2 way ANOVA, p=0.01). Increased expression of four of these cell adhesion molecules in EPC-hTERT cells overexpressing EGFR and mutant p53 compared to control non-invading cells was confirmed by western blot analysis (FIG. 5).

The specifically hybridizing nucleic acids or antibodies immunologically specific for the biomarkers listed in Table 1 can be used to advantage in assays and kits to diagnose those patients having cancer cells which exhibit an increased likelihood for tumor cell migration and invasion. Once a tissue biopsy is performed, the sample can be assessed for genetic signature expression levels or profiles and/or protein production levels, relative to non-invading cells. Such reagents can be combined in a kit. Thus, an aspect of the invention comprises a kit including without limitation, antibodies having binding affinity for the proteins listed in Table 1 and reagents suitable for conducting an ELISA The kit can include immobilized target antigens for use as a positive control and the reagents may optionally be immobilized on a solid support.

TABLE 1

Differentially expressed cell adhesion molecules in invading vs. non-invading cells

| Gene Name | Fold Change (invading vs. non-invading) |
| --- | --- |
| Cadherin 2, type 1, N-cadherin | 13.7 |
| Melanoma cell adhesion molecule | 2.5 |
| Periostin, osteoblast specific factor | 4.8 |
| Cadherin 11, type 2, OB-cadherin | 3.5 |
| Claudin 1 | −1.6 |
| Claudin 4 | −3.1 |
| Claudin 7 | −11.9 |
| Occludin | −9.7 |

EXAMPLE II

Esophageal Cancer and the Tumor Microenvironment

Differences in the activation of stromal fibroblasts appear to determine the rate of tumor cell migration and invasion in the ECM and eventually distant metastasis. ESCC tumors often include a desmoplastic response in the mesenchymal compartment where a significant portion of the tumor is comprised of dense abnormally deposited ECM proteins by activated fibroblasts. Poorly-differentiated tumors have invading tumor cells that migrate in a seemingly stochastic fashion. Our 3D cell culture systems, alternatively referred to as organotypic cultures, precisely recapitulate the in vivo malignant, invasive ESCC. Furthermore, we are able to modulate the degree of tumor differentiation in the ECM by modifying the origin of fibroblasts (skin vs. esophageal). Although skin squamous cell cancers share genetic features with esophageal, head/neck and lung squamous cell cancers, their outcomes are divergent.

The mechanism by which tumor cells promote stromagenesis, such as through transforming growth factor-beta (TGF-beta), have been identified. TGF-beta is produced and secreted by normal epithelial cells, tumors, and stromal fibroblasts as a latent molecule, and is activated by extracellular proteases (including metalloproteinases MMP-2, MMP-9, MT1-MMP) and receptors (including integrins) on the surface of fibroblasts or early stage tumor cells. TGF-beta initially suppresses the growth of an emerging population of tumor cells. At later stages of stroma-dependent tumorigenesis, TGF-beta is indirectly tumor supportive, because during tumor development, its receptors are down-regulated on the tumor cell surface, causing a loss of TGF-beta-responsive growth inhibition in tumor cells. However, because tumor cells continue to produce TGF-beta and stromal fibroblasts maintain high levels of its receptor(s), TGF-beta continues to drive fibroblastic responses (e.g., type I collagen fibrillogenesis), promoting the differentiation of stromal fibroblasts into myofibroblasts. TGF-beta is not the only secreted factor implicated in stromagenesis and an increased invasive potential of tumor cells. Other growth factors can be secreted by fibroblasts including PDGF, HGF, EGF family members, and FGFs. These data suggest that not only is there an interaction between fibroblasts and tumor cells, this interaction is likely to be synergistic. Proliferation, migration and the invasion of tumor cells may well be increased in the environment of a strong desmoplastic response.

Our data and model indicate that alterations in canonical oncogenes (e.g. EGFR) and tumor suppressor genes (e.g. p53, p120ctn) conspire to transform esophageal epithelial cells, thereby fostering tumor cell migration and invasion through the basement membrane into the submucosa, which comprises the extracellular matrix, and cell types such as fibroblasts and endothelial cells. In turn, our work reveals that esophageal tumor cells induce the activation of fibroblasts that create a milieu augmenting tumor invasion. Strikingly, phosphorylated AKT is a critical signature of the activated fibroblasts, which is dependent upon the origin and type of these fibroblasts (fetal esophageal vs. adult esophageal vs. skin). These findings, in aggregate, support a model of interplay of the epithelial and mesenchymal compartments in the tumor microenvironment that have translational implications in combinatorial therapy for ESCC.

Identification of Critical Signaling Pathways in Activated Fibroblasts Involved in Paracrine Signaling to Tumor Cells that Increase Tumor Cell Migration and Invasion into the Tumor Microenvironment: The Origin or Type of Stromal Fibroblasts Differentially Modulates Esophageal Tumorigenesis.

Figure 6:
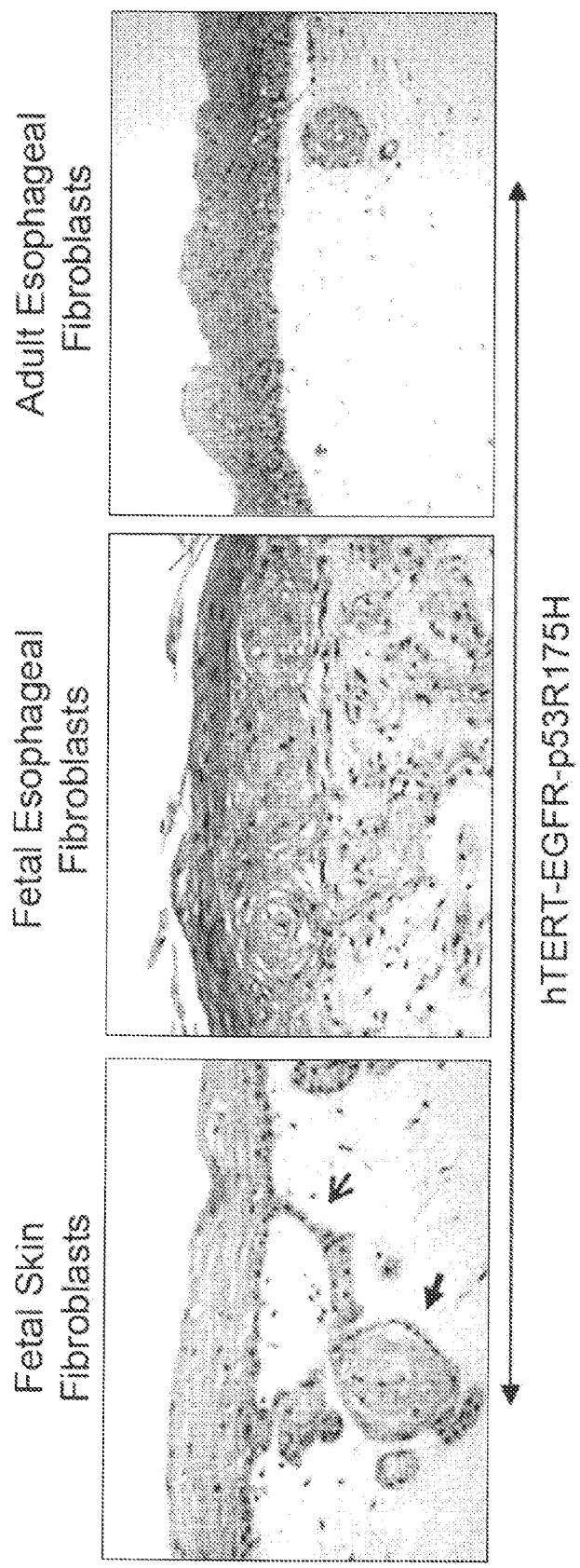
FIG. 6 shows H&E staining of organotypic cultures of triple mutant EPC2-hTERT-EGFR-p53 R175H cells with fibroblasts—fetal skin, fetal esophageal or adult esophageal—in the stromal 3-D matrix. (120×). The invasive phenotype of triple mutant cells reveals hallmark features of ESCC namely keratin "pearls" (closed arrow), epithelial down growth (open arrow), and an aggressive poorly differentiated phenotype (fetal esophageal).

We have demonstrated recently that the source of fibroblasts used in organotypic culture can determine the extent of tumor invasion and the degree of tumor differentiation (Okawa et al. (2007) Genes and Dev. 21:2788-2803). Comparisons were made between human adult and human fetal esophageal fibroblasts and human fetal skin fibroblasts embedded in the matrix with genetically defined transformed esophageal epithelial cells seeded on top (normal human primary esophageal cells, designated as EPC2, with EGFR overexpression, hTERT inactivation and p53 mutation. As shown in FIG. 6, fetal skin fibroblasts in the matrix resulted in well-differentiated ESCCs with the distinctive hallmark feature of keratin "pearl" formation and invasive epithelial down growth. However, when fetal esophageal fibroblasts were embedded in the matrix, the transformed cells invaded in a more aggressive manner with a tendency to a poorly differentiated ESCC phenotype. Adult esophageal fibroblasts appear to be less activated as there was little evidence of invasion into the surrounding matrix. This suggests that the source and activation level of the fibroblasts is important to permitting or restraining tumor growth and invasion, an observation not previously appreciated or recognized.

AKT Phosphorylation is a Key Determinant of the Invasive Promoting Phenotype of Fibroblasts.

Figure 7:
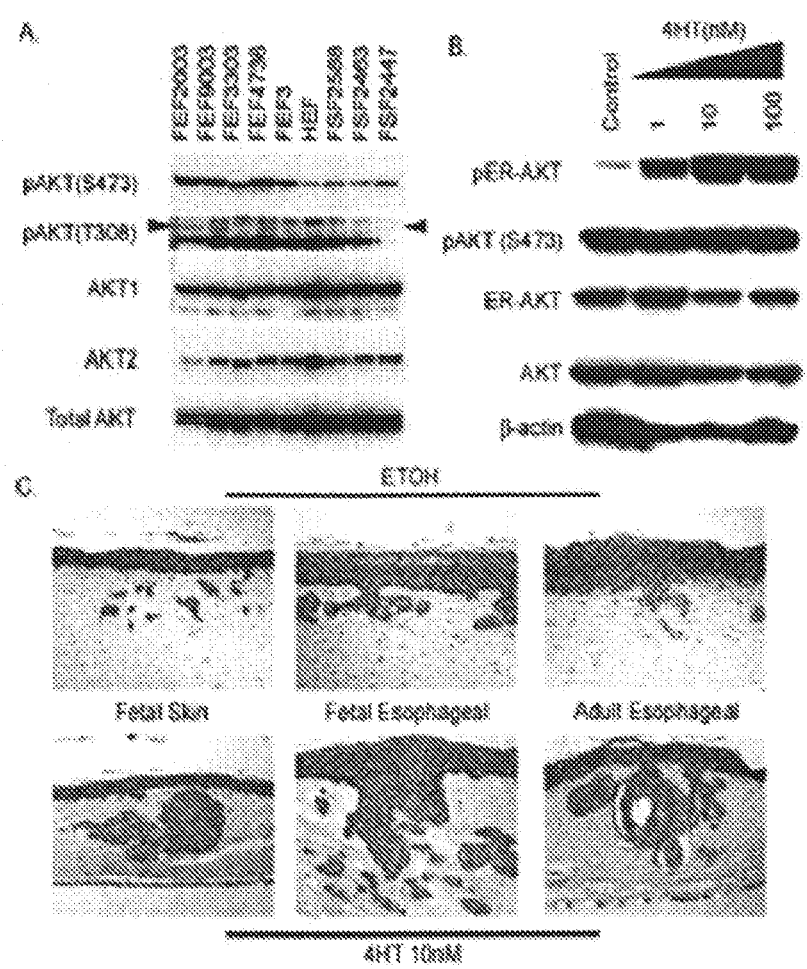
FIG. 7 shows A. Western blots of phospho-AKT (ser 473) and total AKT levels expressed by fibroblast panel using beta-actin as loading control where FEF=fetal esophageal fibroblasts, HEF=adult esophageal fibroblasts and FSF=fetal skin fibroblasts. B. Fibroblasts were infected with pWXL-myrAKT-HA-ER and then stimulated by 4-hydroxy-tamoxifen (4-HT). Levels of ectopic phospho-ERAKT, endogenous phospho-AKT, total ER-AKT, and actin are shown (Fetal skin is shown, similar results with fetal and adult esophageal lines). C. H&E staining of organotypic cultures upon activated ER-AKT overexpression in the different fibroblasts with EPC2-hTERT-EGFR-p53 R175H cells invading into the matrix (60×).

We next investigated which molecules might be differentially activated in the fetal esophageal, fetal skin and adult esophageal fibroblasts. We observed a higher level of AKT phosphorylation in a panel of fetal esophageal fibroblasts when compared to either the fetal skin fibroblasts or adult esophageal fibroblasts (FIG. 7A). We transduced inducible AKT into the fibroblast lines where AKT was myristoylated and fused to the estrogen receptor, ensuring proper location to the plasma membrane and the ability to be activated by tamoxifen. Dose dependent induction of AKT phosphorylation was observed upon tamoxifen treatment in the various fibroblasts lines (FIG. 7B and data not shown). Increased invasion into the matrix was observed in all three fibroblasts lines upon increased AKT phosphorylation (FIG. 7C). In parallel, knockdown of either AKT1 or AKT2 in the matrix embedded fibroblasts significantly reduced the invasive capacity of the transformed esophageal epithelial cells (data not shown). Taken together, these experiments indicate that AKT activation is likely to contribute to differences in the invasion promoting phenotype observed with the different fibroblast lines.

Hepatocyte Growth Factor Secretion is Observed from Fetal Esophageal Fibroblasts Permissive to Tumor Cell Invasion.

We hypothesize that cancer associated fibroblasts (CAFs) create an environment primed for growth and invasion through the secretion of factors. We find that fibroblast secretion of hepatocyte growth factor (HGF) fosters the ability of transformed esophageal epithelial cells to invade into the ECM, although other unidentified factors may cooperate with HGF. Genetic modifications of both HGF in fibroblasts and its receptor Met in epithelial cells along with pharmacologic inhibition of HGF and Met, underscore the importance of this pathway in ESCC invasion and progression. Furthermore, Met activation is increased upon combinatorial overexpression of epidermal growth factor receptor (EGFR) and p53R175H, two common genetic mutations in ESCC. These results highlight the potential benefit of the therapeutic targeting of HGF/Met signaling in ESCC and potentially other squamous cancers where this pathway is deregulated.

HGF (also known as scatter factor) was identified originally because of its ability to induce cell scattering and act as a mitogen of hepatocytes (Nakamura, T. et al. (1986) *Proc Natl Acad Sci USA* 83(17):6489-6493; Stoker, M. et al., (1987) *Nature* 327(6119):239-242). It is expressed ubiquitously and known to impact migration, proliferation, scattering, survival, and branching tubulogenesis. HGF is produced by mesenchymal cells including fibroblasts and binds to the receptor tyrosine kinase Met that is expressed on epithelial and endothelial cells, thereby providing a platform of cross-talk between the epithelial and stromal compartments (Peschard, P. et al. (2007) *Oncogene* 26(9):1276-1285). HGF/Met signaling activates a complex program of responses that has been described collectively as invasive growth necessary both during normal embryonic development and adult tissue repair (Comoglio, P. M. et al. (2008) *Nat Rev Drug Discov* 7(6):504-516; Comoglio, P. M. et al. (2002) *J Clin Invest* 109(7):857-862). HGF/Met signaling is well established to be important for cancer pathogenesis in a wide variety of tumor types largely through Met overexpression, although rare receptor mutations have been detected (Knudsen, B. S. et al. (2008) *Curr Opin Genet Dev* 18(1):87-96). Pharmacologic agents targeting this pathway are under clinical development with some promising preliminary results (Jarvis L M (2007) *Chemical and Engineering News* 85(34):15-3).

In ESCC, pre-therapy serum HGF levels were found to be significantly elevated in patients when compared to control samples. Higher levels of serum HGF correlated with advanced tumor stage and survival (Ren Y, et al. (2005) *Clin Cancer Res* 11(17):6190-6197; Takada N, et al. (1995) *Cancer Lett* 97(2):145-148). HGF was identified as a secreted factor from ESCC-associated fibroblasts and reported to influence cell invasion and migration via activation of VEGF and IL8 expression (Iwazawa T, et al. (1996) *Jpn J Cancer Res* 87(11):1134-1142). We find that HGF is secreted exclusively from fibroblasts which promote matrix invasion of transformed esophageal epithelial cells in organotypic culture and that HGF/Met signaling is activated in human ESCC samples, ESCC cell lines, and upon EGFR and p53$^{R175H}$ overexpressionin our genetically defined model system. Novel genetic and pharmacologic inhibition of HGF/Met attenuates invasion in a dramatic fashion, indicating that this pathway is essential for tumor invasion, and therefore, it may represent a novel approach to ESCC therapy targeting in the early steps of metastasis.

Esophageal CAFs and Fetal Esophageal Fibroblasts Promote Matrix Invasion of Transformed Epithelial Cells.

Figure 8:
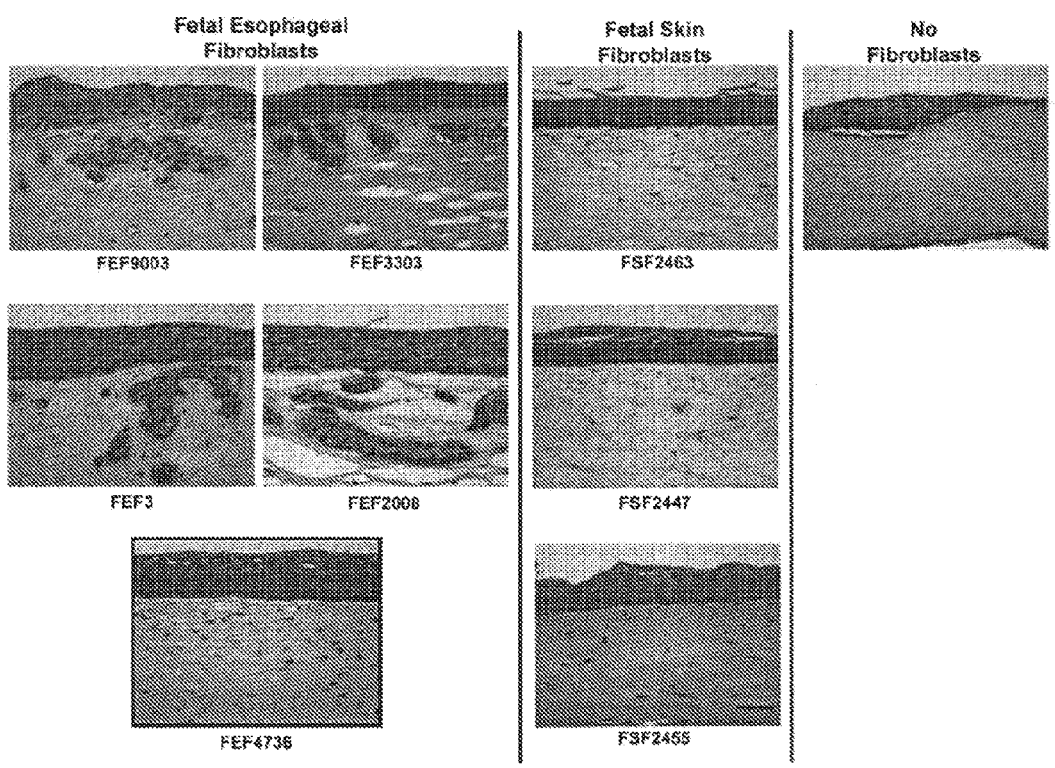
FIG. 8 shows invasion of genetically transformed esophageal epithelial cells occurs into matrices of fetal esophageal fibroblasts. H&E sections of organotypic culture of EPCh-TERT-EGFR-p53$^{R175H}$ seeded above matrices containing the indicated fibroblast sample or no fibroblasts at all (scale bar=100 µm).
Figure 9:
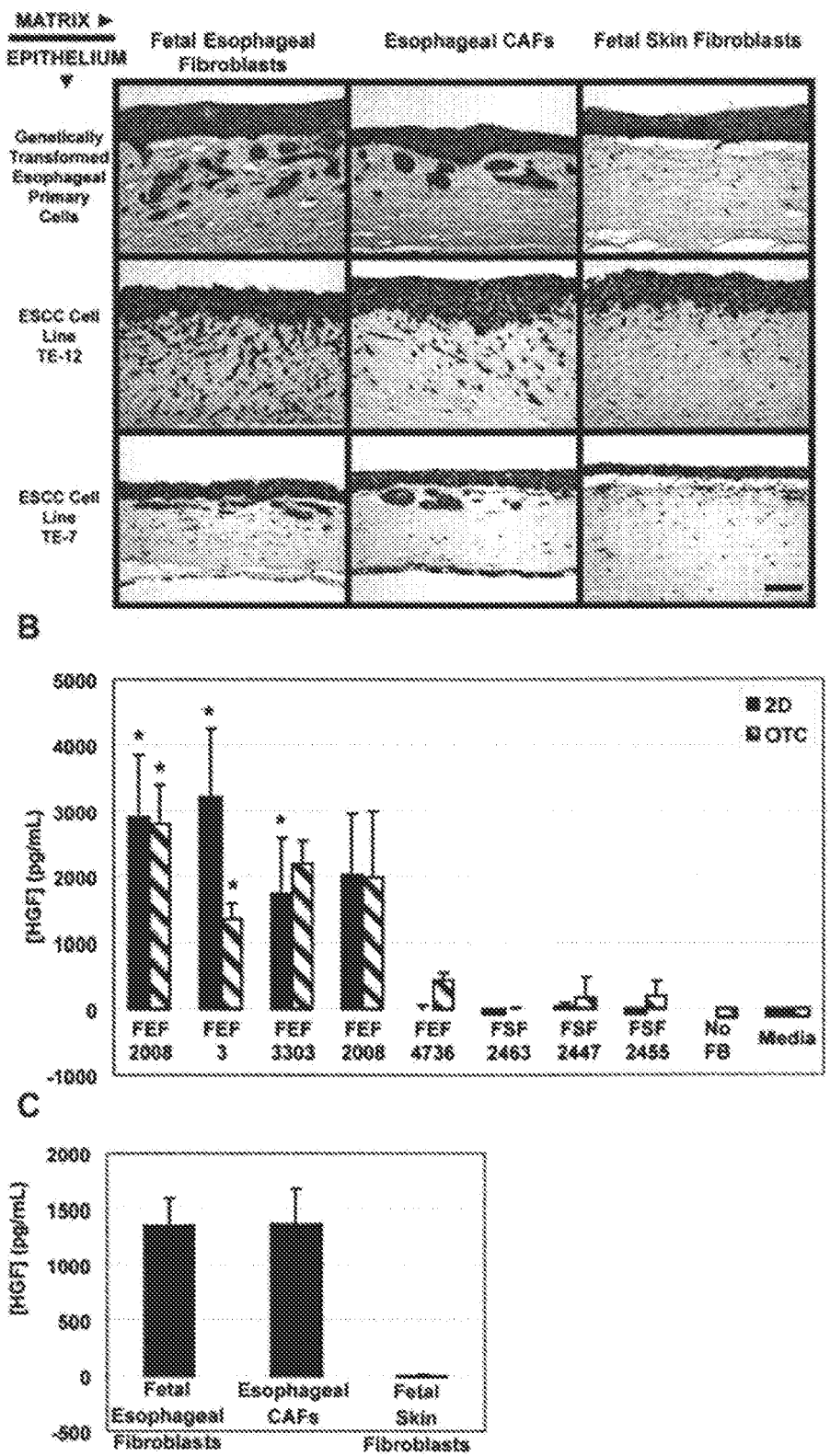
FIG. 9 illustrates that HGF is secreted from tumor esophageal and fetal esophageal fibroblasts which promote invasion of ESCC cells. (A) H&E sections of organotypic culture where EPC-hTERT-EGFRp53$^{R175H}$ (genetically transformed esophageal primary cells), TE12, or TE7 cells were seeded above matrices containing fetal esophageal fibroblasts (FEF3), fetal skin fibroblasts (FSF2463), or esophageal CAFs (TEF1947F1). (B) Level of human HGF detected in conditioned media collected from the indicated fibroblast sample set up either alone in 2D culture or in organotypic culture as measured by ELISA. (C) Level of HGF detected in conditioned media from the organotypic cultures containing fetal esophageal fibroblasts (FEF3), fetal skin fibroblasts (FSF2463), or esophageal CAFs (TEF1947F1). Error bars represent ±SEM and * indicates p values≤0.05 when compared to media (9B, 2D), no fibroblasts (9B, OTC) or fetal skin fibroblasts (9C). Scale bar represents 100 µm.

As described above, we determined that the most aggressive invasion was promoted by fetal esophageal fibroblasts in the matrix as four of the five fetal esophageal fibroblast lines tested supported invasion (FIG. 8). This raised the possibility that fetal esophageal fibroblasts are primed or activated to support invasion and suggests that these closely resemble CAFs in vivo. In order to test this premise, a CAF line derived from a primary ESCC human tumor was obtained and tested for its ability to promote invasion of transformed EPC-hTERT-EGFR-p53$^{R175H}$ cells. Invasion of the epithelium into the ECM was observed when either the esophageal CAFs or fetal esophageal fibroblasts were seeded into the matrix, but not when fetal skin fibroblasts were used (FIG. 9A). We determined if this fibroblast effect was limited only to our genetically transformed esophageal epithelial cells (EPC-hTERT-EGFR-p53$^{R175H}$) by testing two established ESCC cell lines (TE7 and TE12) in organotypic culture seeded on top of matrices containing the respective fibroblast types. We observed the same pattern in both TE7 and TE12 cells with preferential invasion into matrices containing either esophageal CAFs or fetal esophageal fibroblasts when compared to fetal skin fibroblasts (FIG. 9A). Thus, the invasion promoting effects of the fetal esophageal and esophageal CAFs are not limited to our genetically defined model system, but also hold true in human ESCC lines.

HGF is Secreted Only by Fibroblasts Capable of Promoting Epithelial Cell Matrix Invasion.

Figure 10:
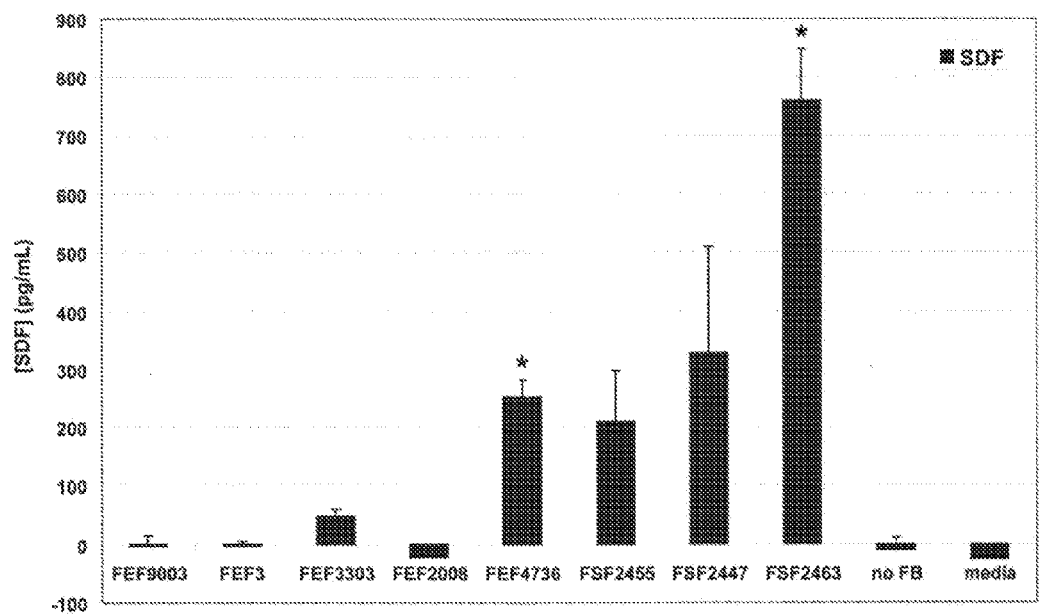
FIG. 10 shows that SDF-1 is secreted by fibroblasts that are not permissive to invasion of transformed esophageal epithelial cells. Level of human SDF-1 detected in conditioned media collected from the indicated fibroblast sample set up in organotypic culture and measured by ELISA. Error bars represent ±SEM and * indicates p values≤0.05 when compared to no fibroblast sample.

In order to identify factors that are secreted differentially by the fibroblasts that promoted invasion, we collected conditioned media from the fibroblasts cultured in 2D culture and in organotypic culture. We chose to screen for two important growth factors in the tumor microenvironment, namely HGF and SDF-1, previously identified in other tissues as fibroblast secreted factors that promote tumor progression (Bhowmick N A, et al. (2004) *Science* 303(5659):848-851; Orimo A, et al. (2005) *Cell* 121(3):335-348). Interestingly, we observed that HGF was secreted only by the four fetal esophageal fibroblasts that promoted invasion in organotypic culture, but not by fetal skin fibroblasts or the one fetal esophageal fibroblast line (FEF4736) that did not promote invasion (FIG. 9B; FIG. 8). HGF was not detected in conditioned media from organotypic cultures established without fibroblasts, but could be detected in matrices established without epithelia, suggesting that the measured HGF is fibroblast-derived (FIG. 9B). The pattern of SDF-1 secretion did not mirror the invasive pattern, but was instead secreted preferentially by the fibroblasts that did not foster invasion (FIG. 10). We next measured HGF secretion from the esophageal CAF line and found HGF levels in conditioned media of esophageal CAFs to be comparable to the levels observed from fetal esophageal fibroblasts (FIG. 9C). Collectively, these results suggest that fibroblast derived HGF, but not SDF-1, can promote esophageal tumor invasion, and prompted us to focus upon HGF as well as the HGF-Met axis.

Figure 11:
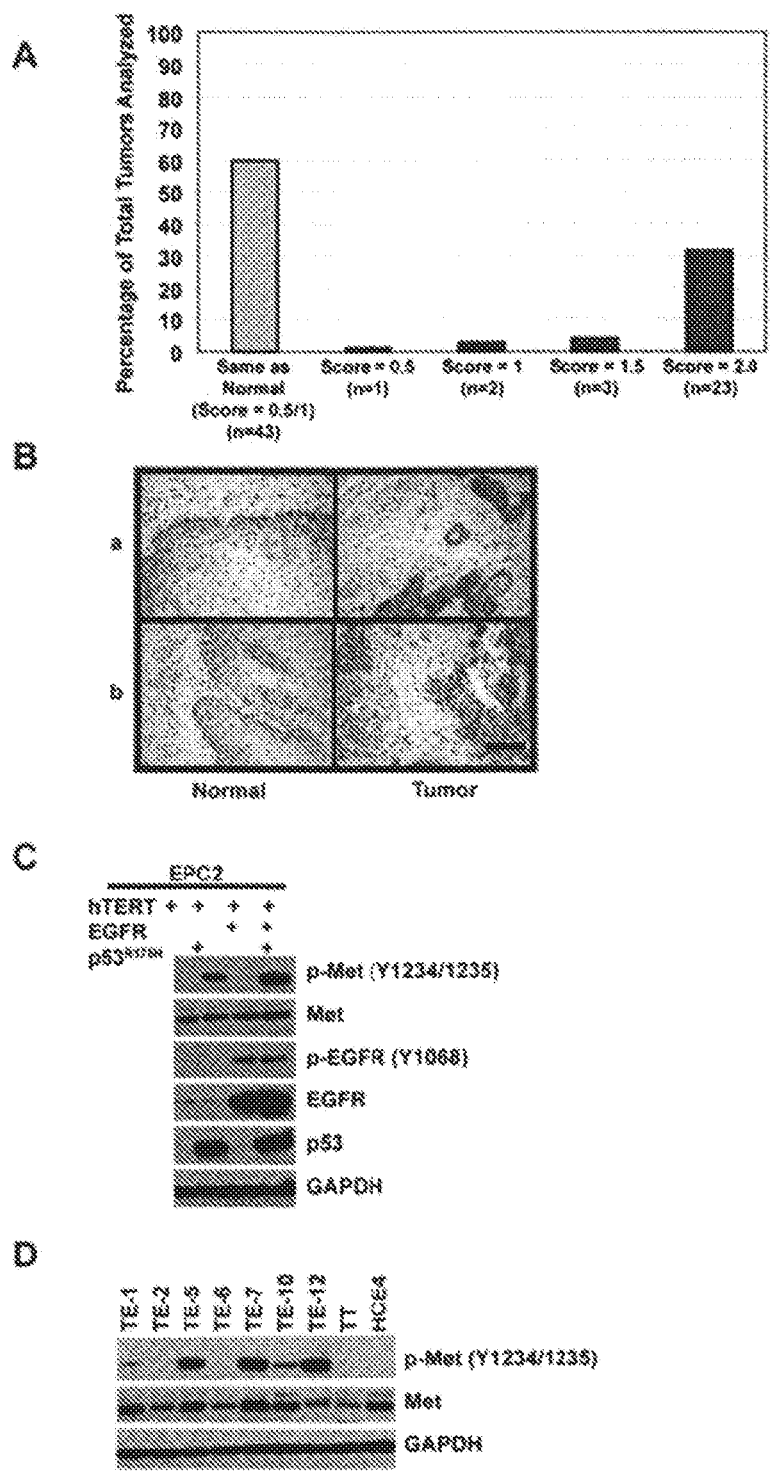
FIG. 11 shows that the HGF receptor Met expression is elevated in human ESCC tumors and activated upon EGFR and p53$^{R175H}$ overexpression. (A) Met IHC staining results of 72 ESCC human tumor microarray samples. (B) Representative images of two ESCC human tumor samples with matched normal mucosa stained for Met (scale bar=100 µm). (C&D) Levels and phosphorylation status of the indicated proteins were measured by Western blotting in whole cell lysates of EPC-hTERT, EPC-hTERT-EGFR-puro, EPC-hTERT-p53$^{R175H}$-neo, and EPChTERT-EGFR-p53$^{R175H}$ cells (C) or a panel of ESCC cell lines (D).
Figure 12:
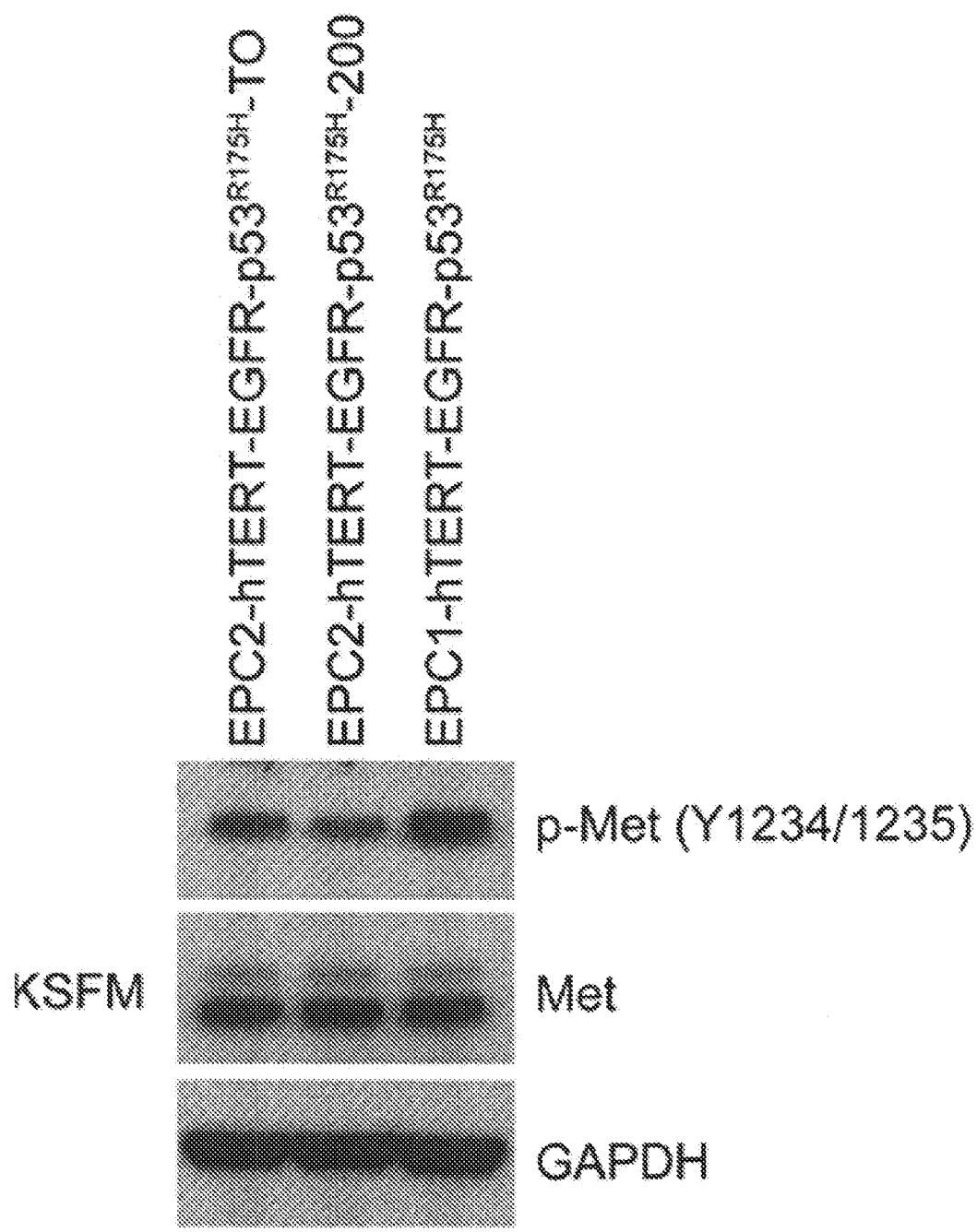
FIG. 12 shows increased Met activation in three independent EPC-hTERT-EGFR-p53$^{R175H}$ cell lines. Levels and phosphorylation status of Met and GAPDH were measured by Western blotting in whole cell lysates of EPC-hTERT-EGFR-p53$^{R175H}$-TO (main cell line used in studies), EPC-hTERT-EGFR- p53R175H-200 (independently generated cell line of same genotype and parental cell), and EPC1-hTERT-EGFR-p53R175H (different parental esophageal primary cell with identical genotype as main cell line used).

Met is overexpressed and activated in ESCC and upon EGFR and mutant p53R175H overexpression. Forty percent of tumors showed increased Met levels in the tumor when compared to the paired normal tissue (FIGS. 11A and 11B) in a human ESCC tumor microarray. In the previous example we have described an increased invasive phenotype in esophageal primary cells transformed by overexpression of EGFR and mutant p53. We now show that these cells preferentially invade in HGF-containing matrices. We next interrogated whether there was a change in the level of Met expression in EPC-hTERT cells upon transformation with EGFR and p53$^{R175H}$ as Met overexpression is a hallmark of aggressive tumors. Interestingly, while we did not observe a difference in Met protein levels upon overexpression of EGFR and/or p53$^{R175H}$ in EPC-hTERT cells, an increase in Met phosphorylated at tyrosine residues 1234/1235 was evident upon expression of p53R175H and further enhanced by increased EGFR (FIG. 11C; FIG. 12). This suggests that the combination of mutant p53$^{R175H}$ and EGFR overexpression leads to increased Met activation and may result in increased dependence upon HGF/Met signaling. Additionally, we observed an increase in both Met protein and its activity (phosphorylation) in a number of ESCC cell lines, including both TE-12 and TE-7 cells (FIGS. 11D and 9A) which we identify as able to invade into HGF rich matrices.

Figure 13:
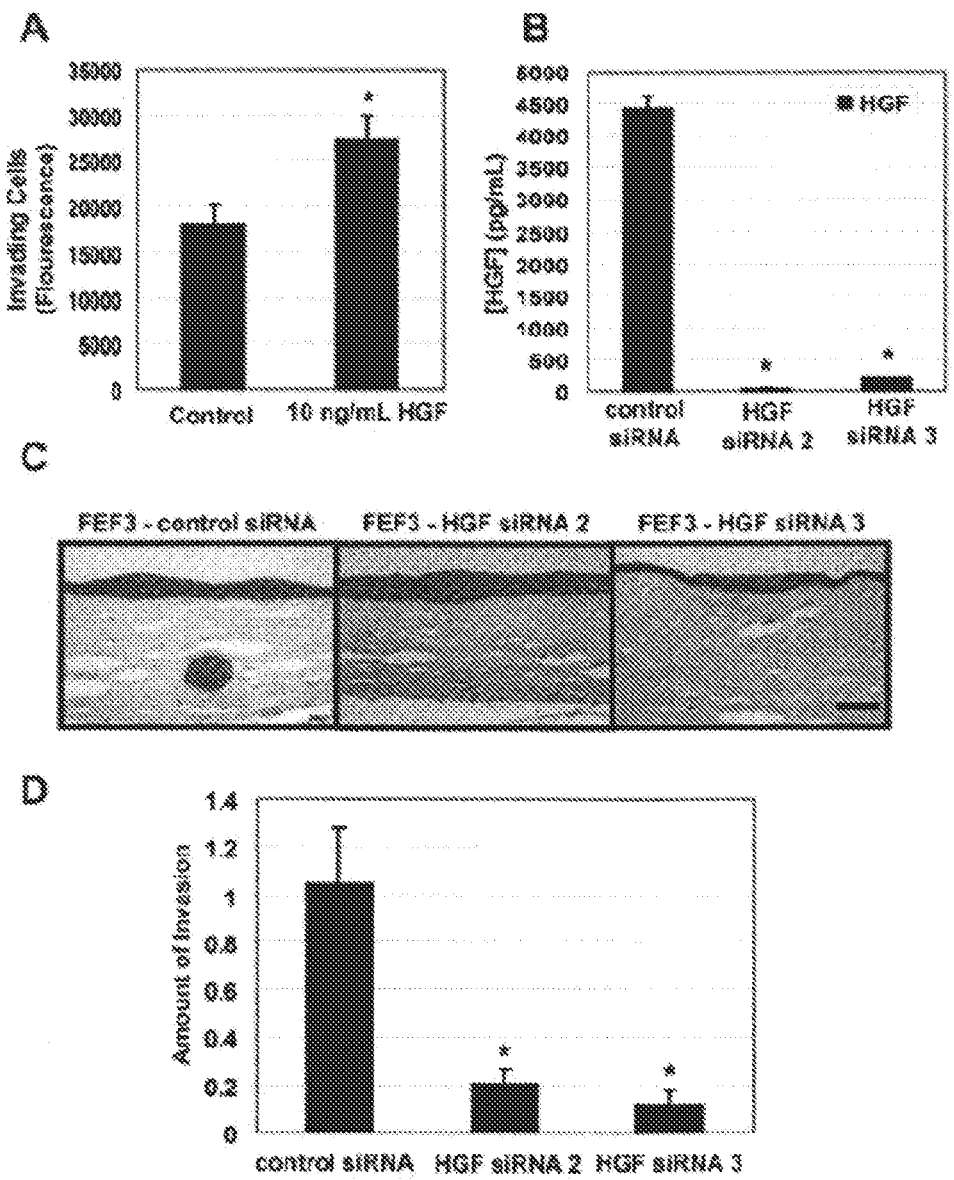
FIG. 13 shows that HGF promotes invasion and HGF knockdown in fetal esophageal fibroblasts blocks invasion of transformed esophageal epithelial cells. (A) Fluorescence measurements representing invading cells on the bottom filters of a Matrigel®-coated Boyden chamber where HGF was added as the chemoattractant of EPC-hTERT-EGFR-p53$^{R175H}$ cells seeded atop the filter. (B) Level of secreted HGF in conditioned media from FEF3 fibroblasts±HGF siRNA set up in organotypic culture and detected by ELISA. (C) H&E sections of organotypic cultures of FEF3 fibroblasts±HGF siRNA seeded into the matrix with EPC-hTERT-EGFR-p53$^{R175}$ grown above (scale bar=100 µm). (D) Quantification of invasion in entire organotypic culture imaged in (C). Error bars represent±SEM and * indicates p values≤0.05 when compared to the control.

Fibroblast derived-HGF is necessary for transformed esophageal epithelial cell matrix invasion. We next tested the direct effect of HGF as a chemo-attractant in a Boyden chamber invasion assay. We observed significantly increased levels of invading EPC-hTERT-EGFRp53 $^{R175H}$ cells when stimulated by HGF (FIG. 13A). In order to determine if HGF is necessary for invasion of EPC-hTERT-EGFR-53$^{R175H}$ cells in organotypic culture, the expression level of HGF was engineered to be reduced in the fibroblasts by means of siRNA targeting HGF. Fetal esophageal fibroblasts (FEF3) with reduced HGF levels were generated following transfection with two independent siRNAs targeting HGF. HGF knockdown was monitored by ELISA of the respective fibroblast conditioned media and secreted levels were reduced more than 95% with either siRNA construct when compared to levels observed using the scrambled siRNA control fibroblasts (FIG. 13B). These HGF knockdown fibroblasts were embedded in the matrices of organotypic culture (24 hours after knockdown) and the effect of HGF level on the ability of EPC-hTERT-EGFR- p53$^{R175H}$ to invade was evaluated. As demonstrated in FIGS. 13C and 13D, invasion was almost completely blocked upon HGF siRNA transfection in fetal esophageal fibroblasts with an 80% and 88% reduction (siRNA 2 and siRNA 3, respectively) in invading cells (EPC-hTERT-EGFR-p53$^{R175H}$).

Figure 14:
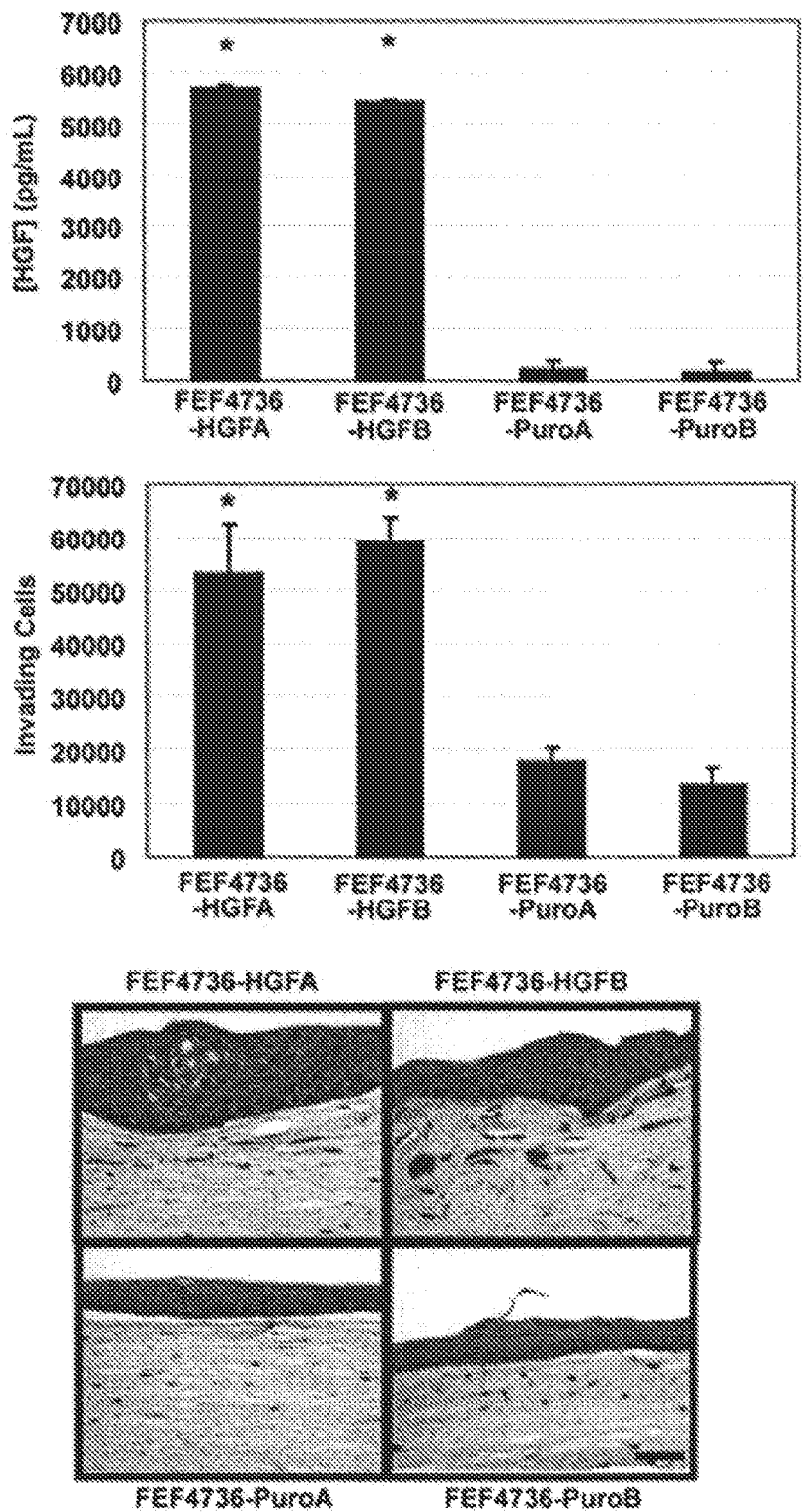
FIG. 14 shows that overexpression of fibroblast secreted HGF promotes transformed esophageal epithelial cell proliferation and invasion. (A) Level of secreted HGF in conditioned media from FEF4736 fibroblasts±HGF overexpression set up in organotypic culture and detected by ELISA. (B)

As shown in FIG. 8, one fetal esophageal fibroblast line (FEF4736) did not secrete HGF or support invasion of ESCC cells. We utilized these fibroblasts to generate two independent cell lines that stably overexpressed HGF and compared them to two empty vector expressing cell lines (FIG. 14A). Conditioned media collected from FEF4736-HGF dramatically enhanced invasion of EPC-hTERT-EGFR-p53$^{R175H}$ cells compared to FEF4736-puro conditioned media in a Boyden chamber invasion assay (FIG. 14B). These fibroblasts were seeded in organotypic culture matrices and tested for their ability to promote invasion of EPChTERT-EGFR-p53$^{R175H}$ cells. HGF overexpression in FEF4736 matrix fibroblasts did not result in conversion to the invasive phenotype observed with the four other HGF-secreting fetal esophageal fibroblasts highlighting the apparent diversity of fibroblasts obtained from the same tissue. However, increased keratin pearl formation (consistent with carcinoma in situ) and dysplasia (FIG. 14C, panel 1) in the epithelium were apparent in the cells seeded atop matrices containing FEF4736-HGF. Small regions of invading areas were also evident (FIG. 14C, panel 2). In combination with the knockdown studies, these results suggest that HGF is necessary for ESCC invasion.

Constitutive activation of Met enhances invasion dramatically. Met was identified originally as part of the oncogene TPR-Met that is the product of a chromosomal translocation induced in carcinogen treated human osteosarcoma cells that fuses translocated promoter region (TPR) to the kinase domain and carboxy terminus of MET. TPR encodes a dimerization leucine zipper motif that when fused to the cytosolic region of MET results in a ligand independent constitutively active dimerized Met protein (Peschard, P. et al., (2007) Oncogene 26(9):1276-1285). TPR-Met has been detected in rare cases of human gastric cancer and has been used widely to study the effects of Met constitutive activation (Soman, N. R. et al., (1991) Proc Natl Acad Sci USA 88(11):4892-4896). We tested the effect of expressing TPR-Met in the non-invasive EPC-hTERTp53$^{R175H}$ cells as another approach to investigate tumor cell invasion in 3D organotypic culture. Two independent lines of stable EPC-hTERT-p53$^{R175H}$-TPR-Met cells were generated along with empty vector control cells (EPC-hTERT-p53$^{R175H}$-puro) for comparison. Stable cell lines could not be generated without the coexpression of mutant p53 due to the oncogenic strength of TPR-Met and subsequent induction of both apoptosis and senescence. In 2D culture, TPR-Met overexpression resulted in a phenotypic change in the cells with decreased cell-cell contact and increased mesenchymal features such as elongated cellular morphologies (FIG. 15A). Expression of TPR-Met was confirmed by Western blotting and shown to be constitutively active (FIG. 15B). Using the EPC-hTERT cells expressing p53$^{R175H}$ and TPR-Met, we tested whether constitutive active Met could promote invasion in conjunction with p53R175H similar to the EGFR/p53$^{R175H}$ combination. As shown in FIG. 15C, matrix invasion was dramatically increased upon expression of TPR-Met when compared to the empty vector control. The epithelium formed by control cells (empty vector) showed a few well differentiated and organized epithelial down growths into the matrix, whereas cells expressing TPR-Met showed a diffuse pattern of invasion characterized by the presence of dysplastic cells penetrating the subepithelial matrix on a broad front and in a haphazard orientation. This pattern of invasion was aggressive and reminiscent of un-differentiated transformed ESCC tumor cells. Interestingly, EPC-hTERT-p53$^{R175H}$-TPR-Met cells did not invade into matrices containing the low HGF expressing FEF4736 fetal esophageal fibroblasts (FIG. 15D).

Pharmacologic or Genetic Inhibition of Met Blocks Invasion.

In order to test the functional importance of Met directly, experiments using shRNA targeting Met were conducted. Stable EPC-hTERT-EGFR-p53R175H-shMet cells were generated with decreased levels of Met protein and activation (FIG. 16A). Two independent lines with Met knockdown were assessed in organotypic culture and compared to lines expressing the shScramble control. As shown in FIG. 16B, while the overall invasion was reduced in these experiments, it is clearly revealed that knockdown of Met decreased the amount of invasion by the EPC-hTERT-EGFR-p53$^{R175H}$ cells±shMet.

In order to test if invasion can be affected by therapeutically targeting HGF/Met, two independent means of pharmacologic inhibition were pursued. A Met receptor tyrosine kinase inhibitor, PHA665752, inhibited invasion of EPC-hTERT-EGFR-p53$^{R175H}$ cells when treated for seven days following epithelial cell seeding or for the final four days when invasion occurs (FIG. 16C). In parallel, 2B8, a mouse anti-human HGF antibody (IgG1) generated from a hybridoma, was tested in organotypic culture. Treatment with 2B8 blocked matrix invasion of EPC-hTERT-EGFR-p53$^{R175H}$ cells when added to the organotypic culture for the entire two week protocol, but not if added only for the final four days when invasion occurs, whereas the control mouse IgG1 antibody had no effect on invasion (FIG. 16D). The timing difference of the two therapeutics is likely due to the technical aspects of the organotypic culture protocol. HGF acts as a trigger to catalyze cell invasion via its effector receptor Met. Since HGF is secreted by the matrix embedded fibroblasts which reside within these cultures throughout the two week protocol, 2B8 treatment was necessary for the entire time in order to penetrate the ECM protein rich matrix and constitutively inhibit HGF. Treatment with the small molecule PHA665752, which inhibits the epithelial receptor, was only necessary in week 2 when the Met-expressing epithelial cells were seeded on top of the fibroblast-embedded matrices.

We have demonstrated that HGF secretion from both esophageal CAFs and fetal esophageal fibroblasts promotes invasion of EPC-hTERT-EGFR-p53$^{R175H}$ cells and ESCC cells into the ECM. Using genetic and pharmacologic methods to inhibit HGF and its receptor Met, we have established the functional importance of this signaling pathway to ESCC invasion. Collectively, our results highlight the dependency of ESCC tumor invasion upon stromal HGF and that HGF/Met signaling is potentiated by EGFR and mutant p53$^{R175H}$. These findings suggest that ESCC and potentially other squamous cancers are excellent candidates for HGF/Met therapeutic studies. This is of importance as the five-year survival rate for patients with esophageal cancer is less than 20% and the extent of tumor invasion and metastasis at time of initial diagnosis influences dramatically survival and treatment options. Thus, targeting tumor invasion by HGF/Met inhibition should provide an efficacious means to interfere with this process.

HGF is expressed ubiquitously and plays an important role in the tumor stromal microenvironment, apart from its functions in organogenesis, regeneration and wound healing. Secreted by mesenchymal cells, HGF acts upon epithelial and endothelial cells. TGF-131 is a known suppressor of HGF. Increased HGF expression from Tgfbr2FSPKO fibroblasts was identified as one mechanism for promoting carcinoma in the mouse forestomach and mammary gland (Bhowmick N A, et al. (2004) *Science* 303(5659):848-851). Genetic modification of human mammary fibroblasts to express HGF prior to xenograft implantation with clinically normal mammary epithelial cells resulted in outgrowth of malignant lesions (Kuperwasser C, et al. (2004) *Proc Natl Acad Sci USA* 101 (14):4966-4971). The HGF/Met signaling pathway has been found to be activated in a number of human tumor types, including ESCC where elevated HGF serum levels correlate with disease severity. Our HGF knockdown studies reveal that the stromal produced HGF is an important component of transformed esophageal epithelial cell invasion. However, this does not preclude the likely involvement of other growth factors and/or cytokines. For example, overexpression of HGF in the FEF4736 esophageal fibroblast line (the single esophageal fibroblast line that was not permissive for invasion) did not result in tumor cell invasion in organotypic culture and EPC-hTERT-p53$^{R175H}$-TPR-Met cells could not invade into FEF4736 containing matrices. Another compelling finding is the enhanced Met activation that is obtained upon EGFR overexpression and p53 mutation in transformed esophageal cells. Moreover, Met phosphorylation is increased in genetically engineered cells expressing p53$^{R175H}$. This phosphorylation is augmented further by EGFR co-expression and is activated in multiple ESCC cell lines derived from tumors. Evidence exists in the literature to support cross-talk between EGFR and Met. Most intriguingly, upregulation of Met signaling has been identified as a mechanism of resistance to EGFR tyrosine kinase inhibition where treatment with a Met inhibitor could rescue the resistance phenotype. The mechanism for increased Met phosphorylation upon p53$^{R175H}$ and EGFR expression in esophageal cells is currently unknown. Autocrine HGF production was not detected in EPC-hTERT-EGFR-p53$^{R175H}$ cells, nor was Met phosphorylation inhibited upon treatment with the AG1478 EGFR kinase inhibitor (data not shown).

Agents to target the HGF/Met signaling pathway are in preclinical and clinical development (Comoglio et al., supra). We present novel data that invasion can be blocked by a Met tyrosine kinase inhibitor (PHA665752), which has a closely related compound that is in clinical development for human treatment and by an antibody directed at HGF (2B8), whose humanized version SCH900105 is in clinical development. Our data argue for clinical trials using HGF/Met inhibition in combination with standard chemotherapy or other receptor tyrosine kinase-directed inhibitors (e.g. EGFR inhibition) as in ESCC and potentially other similar squamous cell cancers. Activated Mouse Fibroblasts are Recruited to Subcutaneous ESCC Tumors.

Figure 17E:
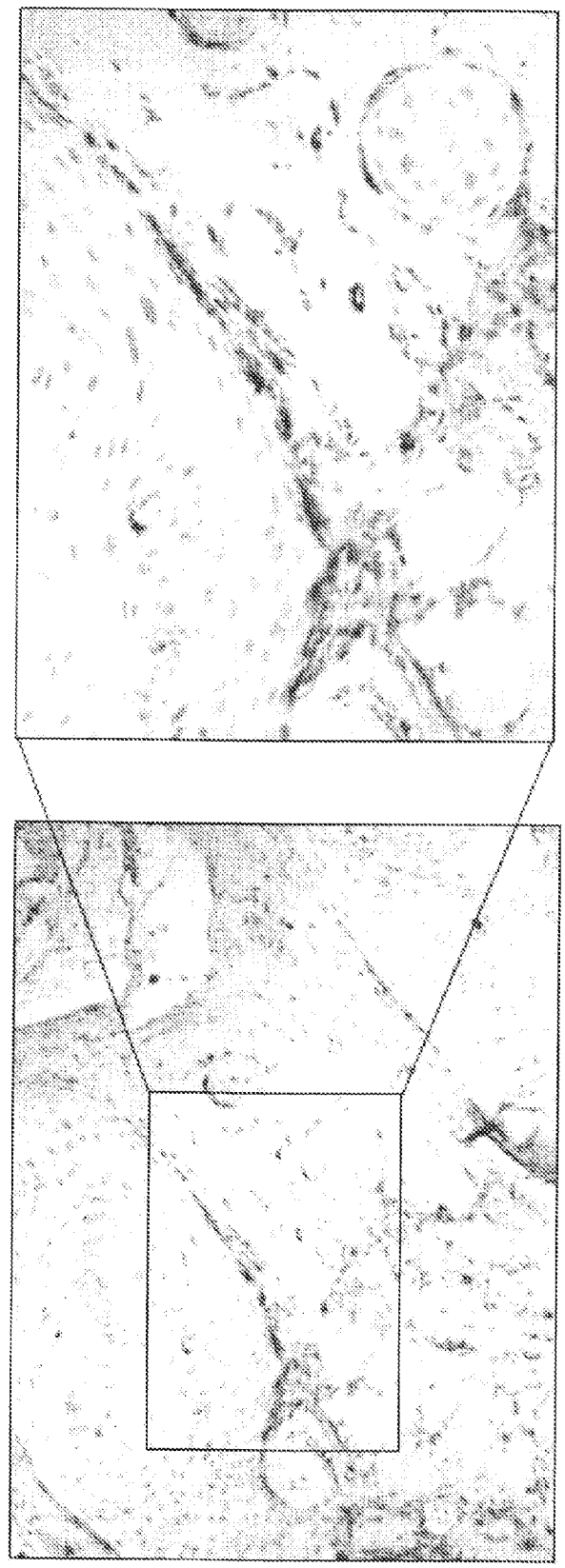

We have recently reported that genetically defined transformed esophageal epithelial cells subcutaneously injected into athymic nude mice formed tumors that phenocopy human esophageal squamous cell carcinomas (FIG. 17A-C). There was invasion through the ECM by the tumor cells (FIG. 17D) with recruitment of activated fibroblasts (alpha-smooth muscle actin positive) surrounding the tumor (FIG. 17E).
Ability of Fibroblasts to Promote in vivo Tumor Formation and Progression The importance of the fibroblast component to tumor progression in vivo will be tested. In order to allow for in vivo live imaging, all fibroblast lines will be infected with a retroviral construct expressing GFP (green) and EPC2-hTERT-EGFR-p53$^{R175H}$. Cells will also be infected with a retroviral construct expressing TdTomato (red). We will mix EPC2-hTERT-EGFR-p53$^{R175H}$ with an equal number of fibroblasts and inject these mixtures in 30% Matrigel® into the dorsal skin of athymic nude mice to determine the rate of tumor formation by the transformed epithelial cells. Mice will be injected for each combination of EPC2-hTERT-EGFR-p53$^{R175H}$ cells and fibroblasts from the four different groups (fetal esophageal, fetal skin, adult esophageal, and tumor associated fibroblasts) and one set of mice will be injected with just EPC2-hTERT-EGFR-p53$^{R175H}$ to serve as a control. 6 mice will be injected per test group. Mice will be checked twice weekly for tumor formation and live imaging will be done using the IVIS bioluminescence and fluorescence imaging system (Xenogen) in Penn's Small Animal Imaging Facility. Once tumors reach 10×10 mm size, tumors will be histologically analyzed for the presence of both cell populations within the tumor by fluorescence analysis for GFP and TdTomato as well as recruitment of non-fluorescently labeled cells from the mouse (fibroblasts, immune cells). The lungs and the liver of all tumor-bearing mice will be harvested and analyzed for metastatic lesions by histology. We report in preliminary data the formation of tumors upon subcutaneous implantation of EPC2-hTERT-EGFR-p53$^{R175H}$ cells into nude mice as well as recruitment of activated mouse fibroblasts and invasion of the tumor cells into stromal and muscle. We will look for the development of tumor desmoplasia upon co-implantation with human fibroblasts. We will also use the modified fibroblasts described in preliminary data that have been genetically modified to stably knock-down or over-express AKT in co-injections with the EPC2-hTERT-EGFR-p53$^{R175H}$ cells to elucidate if AKT activation in the fibroblasts can influence tumor formation in vivo.

EXAMPLE III

As mentioned above, human squamous cell cancers are the most common epithelially derived malignancies. In this example, we provided evidence demonstrating that periostin, a highly expressed cell adhesion molecule, is a key component of the novel tumor invasive signature obtained from an organotypic culture model of engineered ESCC described above. This tumor invasive signature classifies with human ESCC microarrays, underscoring its utility in human cancer. Genetic modulation of periostin promotes tumor cell migration and invasion as revealed in gain of and loss of function experiments. Inhibition of EGFR signaling and restoration of wild-type p53 function were each found to attenuate periostin action, suggesting interdependence of two common genetic alterations with periostin function. Collectively, our studies reveal periostin as an important mediator of ESCC tumor invasion and they indicate that organotypic (3D) culture can offer an important tool to discover novel biologic effectors in cancer.

Identification of Periostin from Tumor Invasion Signature Derived from Gene Expression Profile Analysis on Invading EPC2-hTERT-EGFR-p53$^{R175H}$ Cells and ESCC Tumor Microarrays To determine whether the invasive signature derived from invading EPC2-hTERT-EGFR-p53$^{R175H}$ cells grown in organotypic culture provided in Table 2 can be extended to human ESCC, we analyzed gene expression profiles from five paired human ESCCs. We found that overall gene expression patterns of invasive cells grown in organotypic culture are highly similar to those from ESCC tumors and this tumor invasive signature was able to discriminate esophageal tumors from adjacent normal tissue and classified all tumors and 80% of the normal samples correctly (FIGS. 18A and 18B). To validate this tumor invasive signature, we performed a secondary analysis on an independent cohort of five paired human ESCC tumors using this tumor invasive signature and observed that it was capable of classifying 80% of ESCC tumors and all adjacent normal tissues correctly (FIG. 18C). Using the t-test statistic to rank the probesets in this tumor invasive signature,

TABLE 2

Genes with at least two fold higher expression in invasive EPC.hTERT.EGFR-p53$^{R175H}$ cell lines compared to non-invasive EPC2.hTERT.EGFR.p53$^{R175H}$/EPC.hTERT.EGFR.puro/ EPC2.hTERT.neo.p53$^{R175H}$ cell lines by GO Biological Processes

| Cellular Component Organization and Biogenesis GO: 0016043 | | | Biological Adhesion and Cellular Adhesion GO: 0022610 & GO: 0007155 | | | Developmental Processes GO: 0048856, 0032502, 0048731, 0009888, 0048513 & 0007275 | | |
|---|---|---|---|---|---|---|---|---|
| Probe Set | Gene Name | Ratio* | Probe Set | Gene Name | Ratio* | Probe Set | Gene Name | Ratio* |
| 210809_s_at | POSTN | 6.54 | 210809_s_at | POSTN | 6.54 | 210809_s_at | POSTN | 6.54 |
| 211964_at | COL4A2 | 4.28 | 226237_at | COL8A1 | 5.43 | 206300_s_at | PTHLH | 4.01 |
| 216250_s_at | LPXN | 4.17 | 201109_s_at | THBS1 | 5.11 | 212667_at | SPARC | 3.72 |
| 210511_s_at | INHBA | 3.93 | 204955_at | SRPX | 4.61 | 209270_at | LAMB3 | 3.27 |
| 201162_at | IGFBP7 | 3.72 | 216250_s_at | LPXN | 4.17 | 202267_at | LAMC2 | 2.76 |
| 231766_s_at | COL12A1 | 3.67 | 209651_at | TGFB1I1 | 4.15 | 229404_at | TWIST2 | 2.65 |
| 213869_x_at | THY1 | 3.60 | 227566_at | HNT | 3.98 | 200827_at | PLOD | 2.24 |
| 201389_at | ITGA5 | 3.50 | 231766_s_at | COL12A1 | 3.67 | 213139_at | SNAI2 | 2.14 |
| 202760_s_at | AKAP2 | 3.47 | 213869_x_at | THY1 | 3.60 | 203695_s_at | DFNA5 | 2.07 |
| 201645_at | TNC | 3.44 | 201389_at | ITGA5 | 3.50 | | | |
| 203562_at | FEZ1 | 3.37 | 201645_at | TNC | 3.44 | | | |
| 224911_s_at | DCBLD2 | 3.31 | 203562_at | FEZ1 | 3.37 | | | |
| 212233_at | MAP1B | 3.26 | 224911_s_at | DCBLD2 | 3.31 | | | |
| 209210_s_at | PLEKHC1 | 3.24 | 209270_at | LAMB3 | 3.27 | | | |
| 230175_s_at | ESDN | 3.08 | 209210_s_at | PLEKHC1 | 3.24 | | | |
| 205120_s_at | SGCB | 2.94 | 212489_at | COL5A1 | 3.17 | | | |
| 221916_at | NEFL | 2.93 | 202998_s_at | LOXL2 | 3.15 | | | |
| 204682_at | LTBP2 | 2.89 | 230175_s_at | ESDN | 3.08 | | | |
| 37408_at | MRC2 | 2.87 | 52255_s_at | COL5A3 | 3.02 | | | |
| 219257_s_at | SPHK1 | 2.86 | 212464_s_at | FN1 | 2.93 | | | |
| 218638_s_at | SPON2 | 2.74 | 211340_s_at | MCAM | 2.79 | | | |
| 208637_x_at | ACTN1 | 2.72 | 202267_at | LAMC2 | 2.76 | | | |
| 224252_s_at | FXYD5 | 2.66 | 218638_s_at | SPON2 | 2.74 | | | |
| 204466_s_at | SNCA | 2.61 | 208637_x_at | ACTN1 | 2.72 | | | |
| 218980_at | FHOD3 | 2.56 | 222108_at | AMIGO2 | 2.71 | | | |
| 218368_s_at | TNFRSF12A | 2.55 | 205534_at | PCDH7 | 2.66 | | | |
| 208079_s_at | STK6 | 2.53 | 224252_s_at | FXYD5 | 2.66 | | | |
| 201042_at | TGM2 | 2.53 | 218368_s_at | TNFRSF12A | 2.55 | | | |
| 202095_s_at | BIRC5 | 2.51 | 201042_at | TGM2 | 2.53 | | | |
| 201505_at | LAMB1 | 2.48 | 204359_at | FLRT2 | 2.52 | | | |
| 202796_at | SYNPO | 2.47 | 201505_at | LAMB1 | 2.48 | | | |
| 210026_s_at | CARD10 | 2.47 | 204345_at | COL16A1 | 2.47 | | | |
| 221748_s_at | TNS | 2.40 | 242064_at | SDK2 | 2.45 | | | |
| 203131_at | PDGFRA | 2.35 | 201474_s_at | ITGA3 | 2.35 | | | |
| 218644_at | PLEK2 | 2.32 | 226609_at | DCBLD1 | 2.29 | | | |
| 221898_at | T1A-2 | 2.27 | 225293_at | COL27A1 | 2.15 | | | |
| 201185_at | PRSS11 | 2.23 | | | | | | |
| 204170_s_at | CKS2 | 2.22 | | | | | | |
| 211725_s_at | BID | 2.20 | | | | | | |
| 201540_at | FHL1 | 2.13 | | | | | | |
| 214752_x_at | FLNA | 2.03 | | | | | | |

*Multivariate logistic regression models were used to test each probeset and adjusted for false discovery rate (p < 0.01)

we identified periostin, a cell adhesion molecule, with the most significant difference in gene expression between invading transformed esophageal epithelial cells compared to non-invading normal or dysplastic epithelial cells (t-test for two independent groups, p<0.0001). Strikingly, periostin was also found to be significantly upregulated in both independent cohorts of human ESCC tumors compared to adjacent normal tissue, the fold change in mean periostin expression was found to be 5.0 and 5.7 in the respective cohorts.

To explore the biological processes associated with invasion of ESCC, we tested for enrichment of gene ontology (GO) terms within this tumor invasive signature. This tumor invasive signature was found to be significantly enriched in nine biological processes (FDR, p<0.01). To investigate the cellular processes altered within the tumor microenvironment, we selected three biological processes for further investigation and observed that probesets clustered in each biological process (cell/biological adhesion, development-related and cellular component organization and biogenesis) were able to classify invading transformed esophageal epithelial cells from non-invading cells (Table 2 and FIG. 19A-C). Interestingly, periostin was found to be the highest upregulated gene (6.54 fold) across the three biological processes (Table 2), and was unique in this feature amongst all the genes in the datasets. In aggregate, these results reveal a tumor invasive signature derived from the organotypic culture model which is applies faithfully to human ESCC and highlights periostin as an important gene required for facilitating tumor cell invasion.

Periostin is Expressed Preferentially in Invading EPC2-hTERT-EGFR-p53$^{R175H}$ Cells Both in vitro and in vivo We next sought to validate whether the upregulation of periostin is concomitant with invading transformed esophageal cells as well as establish the localization of periostin expression in these cells. Consistent with the results of the microarray analysis, increased periostin mRNA expression in invading EPC2-hTERT-EGFR-p53$^{R175H}$ cells was confirmed by LCM isolation of invading and non-invading EPC2-hTERT-EGFR-p53$^{R175H}$ cells in the organotypic culture model followed by RNA isolation, amplification and qPCR analysis (FIG. 20A). Furthermore, periostin protein accumulation in invading EPC2-hTERT-EGFR-p53$^{R175H}$ cells grown in organotypic culture was observed by immunohistochemical staining (FIG. 20B, Right panel b), but not in control EPC2-hTERT-EGFR cells (FIG. 20B, Left panel a). Interestingly, periostin protein expression was also observed in the epithelial-stromal interface in tumors formed by EPC2-hTERT-EGFR-p53$^{R175H}$ cells in a xenograft tumor model (FIG. 20C, white arrows). These results establish preferential expression of periostin in invading EPC2-hTERT-EGFR-p53$^{R175H}$ cells both in vitro and in vivo.

Loss of Periostin Leads to Decreased Migration and Invasion in EPC2-hTERT-EGFR-p53$^{R175H}$ Cells Previous efforts involving other epithelial cancers had indicated that periostin promotes invasion and anchorage-independent growth in several epithelial cancer cell lines and in tumors such as head and neck cell carcinoma, oral, breast and ovarian cancers (Kudo, Y. et al. (2006) Cancer Res, 66: 6928-6935; Siriwardena, B. S., et al., (2006) Br J Cancer, 95: 1396-1403; Puglisi, F., et al., (2008) J Clin Pathol, 61: 494-498; Gillan, L., et al. (2002) Cancer Res, 62: 5358-5364). Elevated levels of periostin have been detected in sera of patients with breast, thymoma and non-small cell lung cancer, suggesting periostin secretion during tumorigenesis (Sasaki, H., et al., (2003) Breast Cancer Res Treat, 77: 245-252; Sasaki, H., et al., (2001) Cancer, 92: 843-848; Sasaki, H., et al., (2001) Cancer Lett, 172: 37-42). We sought to investigate directly whether periostin had a functional role in facilitating tumor cell migration and invasion in ESCC. An RNA interference approach with shRNA was used to induce stable knockdown of periostin expression in EPC2-hTERT-EGFR-p53$^{R175H}$ cells (FIG. 21A). Knockdown of periostin in EPC2-hTERT-EGFR-p53$^{R175H}$ cells led to significant decrease in cell migration and invasion compared to control shscrambled cells (FIG. 21B, 21C). Notably, reduced periostin expression in EPC2-hTERT-EGFR-p53$^{R175H}$ cells also resulted in decreased invasion of these cells into the underlying matrix in organotypic culture (FIG. 21D).

Periostin Overexpression Promotes Increased Migration and Invasion in EPC2-hTERT-EGFR-p53$^{R175H}$ Cells In parallel studies, periostin was retrovirally overexpressed in two independent cell lines (EPC2-hTERT-EGFR-p53$^{R175H}$-1 and EPC2-hTERT-EGFR-p53$^{R175H}$-2) (FIG. 22A) and while overexpression of periostin showed no effect on proliferation (data not shown), we observed that these cells displayed increased migration and invasion (FIG. 22B, 22C). Furthermore, when EPC2-hTERT-EGFR- p53$^{R175H}$ cells overexpressing periostin were grown in organotypic culture, increased invasion into the underlying matrix was also observed (FIG. 22D). Collectively, these results demonstrate the direct functional role of periostin in promoting tumor cell migration and invasion, particularly within the context of the tumor microenvironment.

Upregulation of Periostin Expression in Primary ESCC Tumors and in a Cancer Tissue Microarray We next sought to determine if upregulation of periostin is also found in human ESCC by assessing periostin expression in primary ESCC (Grade III) tumors. Increased periostin mRNA expression was observed in ESCC tumors compared to their matched normal controls (FIG. 23A). A marked increase in periostin protein levels was observed in all ESCC tumors studied compared with their matched normal mucosa controls (FIG. 23B and data not shown). To determine the localization of periostin in human ESCC, further immunohistochemical analysis of periostin expression was performed in a tissue microarray containing 73 ESCC tumors and adjacent normal tissue and revealed periostin expression in invasive ESCC tumor cells (FIG. 23C, Bottom panel c, arrowheads) and consistent accumulation in tumor stroma (FIG. 23C, Bottom panel c, arrows) compared to normal esophageal tissue where periostin expression was detected primarily in and around blood vessels (FIG. 23C, Left panel a, arrows). Periostin expression was also detected in high grade esophageal intraepithelial neoplasia (EIN), which was found in a restricted number of cases, particularly in the epithelial-stromal interface (FIG. 23C, Right panel b, arrows). In addition, the stroma in all 73 ESCC cases were scored for periostin immunohistochemical staining intensity and it was shown to have higher levels of periostin staining compared to matched normal esophagus which showed weak to no periostin staining. Specifically, the ESCC scored either 2 or 3, meaning moderate or intense staining, whereas the normal esophagus was 0 or 0.5 (FIG. 23C, panel d), which would suggest that induction of periostin could also arise in the stroma during ESCC progression.

Induction of Periostin is Dependent Upon EGFR Signaling and p53 Mutation

It is believed, but not established, that periostin might enhance tumor cell invasion and metastasis through increased integrin signaling, augmenting cell survival through the PI3K/Akt pathway or fostering epithelial-to-mesenchymal transition (EMT). Given that periostin was identified initially in invading EPC-hTERT-EGFR-p53$^{R175H}$ cells through functional genomics and bioinformatic analysis, we hypothesized that periostin expression is dependent upon both activated EGFR signaling and p53 mutation. Notably, periostin expression was upregulated in EPC2-hTERT-EGFR-p53$^{R175H}$ cells compared to control cells overexpressing EGFR alone (EPC2-hTERT-EGFR) or mutant p53 alone (EPC2-hTERT-p53$^{R175H}$) (FIG. 24A). In addition, periostin promoter reporter assays in EPC2-hTERT-EGFR-p53$^{R175H}$ cells displayed the highest promoter activity compared to control cells with either EGFR overexpression or p53 mutation alone (data not shown), suggesting that both genetic alterations may be required to activate periostin expression at a transcriptional level. This result was further corroborated when EPC2-hTERT-EGFR-p53$^{R175H}$ cells were stimulated with EGF and increased periostin protein expression was observed (FIG. 24B). This induction of periostin upon EGFR stimulation led us to test whether inhibition of EGFR signaling and/or restoration of wild-type p53 function could inhibit periostin by treating EPC2-hTERT-EGFR-p53$^{R175H}$ cells. We employed AG1478, a EGFR tyrosine kinase inhibitor, and 5-iminodaunorubicin, a small molecule compound which restores wild-type p53 signaling by inducing apoptosis and cell cycle arrest, as illustrated by induction of p21(Wang, W., et al., (2006) Proc Natl Acad Sci USA, 103: 11003-11008). Periostin protein expression was noted to be decreased when inhibited by AG1478 or 5-iminodaunorubicin or both (FIG. 24B). Taken together, these data support the notion that periostin expression is modulated mechanistically by activated EGFR signaling and p53 mutation.

Discussion

Overall, our results reveal a novel tumor invasive signature derived from invading transformed cells compared to control noninvading normal and dysplastic cells in organotypic (3D) culture. This signature is one that annotates primary invasive human esophageal squamous cell cancer as distinctive from adjacent normal human esophageal mucosa in two independent cohorts of tumors, underscoring the fidelity and utility of this tumor invasive signature. Indeed, this molecular signature might be informative for other squamous cell cancers arising in different tissues.

Gene ontology analysis (DAVID databases) of specific biological processes that are believed to be involved in the tumor microenvironment reveals the consistent and unique upregulation of periostin, suggesting its critical functional role. First, periostin was found to be upregulated in invading transformed cells and in primary esophageal squamous cell cancers based upon immunohistochemical and Western blot analysis. Second, periostin's direct functional role is underscored by overexpression and knockdown experiments in which genetic manipulation of periostin dramatically influences the degree of tumor invasion in organotypic culture. Third, EGFR signaling and p53 mutation, both canonical genetic alterations in ESCC, appear to converge upon periostin based upon luciferase reporter gene assays as well as inhibition of EGFR signaling and restoration of wild type p53 function. In aggregate, these novel results underscore the utility of the organotypic culture model for the discovery of direct biological effectors of tumor invasion into the microenvironment, which has been largely elusive to date. Local tumor invasion in the mesenchymal stromal compartment is important given that it temporally precedes tumor dissemination in the lymphatic and blood vessels for tumor metastasis.

Periostin has been shown also to have a role in bone, tooth and heart formation during development (Rios, H., et al. (2005) Mol Cell Biol, 25: 11131-11144; Butcher, J. T., et al., (2007) Dev Biol, 302: 256-266) and is only re-expressed and upregulated in adult tissue after vascular, skeletal or bone injuries. Periostin is similarly overexpressed in human cancers. Our results highlight that a tumor invasive signature defines genetically engineered ESCC that is reproduced in human ESCC. Our studies also suggest that induction of periostin, a secreted protein with a long half-life (FIG. 25), may alter the tumor microenvironment by accumulating in the stroma and facilitating invasion through matrix remodeling. This may be achieved through regulation of collagen I fibrillogenesis, serving as a bridge between tenascin C and the extracellular matrix, as well as through interaction with $\alpha_V\beta_3$ integrins. Furthermore, periostin may promote tumor cell survival in the matrix of the microenvironment by activating the Akt/PI3K pathway. Lack of periostin may lead to suppression of Notch1 signaling (Tkatchenko, T. V., et al., (2009) Physiol Genomics, 39: 160-168), conversely, it is conceivable that overexpression of periostin could activate Notch1 signaling in cancers. Indeed, we have evidence of activated Notch signaling in invasive tumor cells grown in organotypic culture (data not shown). Clearly, periostin provides an attractive therapeutic target, especially in a combinatorial fashion, for example, with inhibitors of receptor tryosine kinases.

Various avenues of investigation have highlighted the important role of the microenvironment in enhancing the initial dissemination of malignant tumor cells. Dynamic interactions between the epithelium and mesenchymal stroma contribute to boosting the invasive phenotype of tumor cells by activating a variety of genes facilitating cell proliferation, de-differentiation, migration and invasion. Significant changes such as loss of cell-cell contacts, disruptions in cell adhesion junctions and altered cell-extracellular matrix interactions within the tumor microenvironment converge to increase the ultimate metastatic potential of tumor cells. Therefore, identification of gene expression pattern changes during initial stages of tumor progression within the tumor microenvironment is crucial to understanding the causes of tumor invasion, and ultimately, tumor metastasis to distant organ sites. The 3D organotypic-cell cultures and method of use described herein provide genetic signatures that mediate tumor cell migration and invasion and further elucidate the molecular mechanisms of stromatogenesis (activation of mesenchymal stromal fibroblasts). The processes and targets described herein provide new avenues for the development of therapeutic and diagnostic agents for the treatment of cancer and other hyperproliferative disorders.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An organotypic culture comprising an artificial stroma including a mixture of collagen and human fibroblasts isolated from a tissue of interest, said stroma being overlayed with primary keratinocytes, said keratinocytes comprising transduced nucleic acids encoding at least one activated oncogene and a transduced nucleic acid molecule which inhibits p120ctn action, said molecule being selected from the group consisting of small hairpin RNA (shRNA), siRNA, and microRNA, said culture exhibiting enhanced cell migration and invasion in an artificial extracellular matrix relative to control keratinocytes which lack said nucleic acids.

2. The organotypic culture according to claim 1 wherein said keratinocytes are obtained from a tissue type selected from the group consisting of skin, oral cavity, tracheal, esophageal, cervical, head/neck, and anogenital tissue types.

3. The organotypic culture according to claim 1, wherein said keratinocytes are obtained from esophageal tissue.

4. The culture according to claim 1, wherein said at least one activated oncogene is selected from the group of epidermal growth factor receptor, and cyclin D1, H-tert, CDK4, CDK6, ras, and myc.

5. The culture according to claim 4 wherein said at least one activated oncogene is epidermal growth factor receptor and H-tert and wherein said keratinocytes further comprise transduced nucleic acids encoding at least one non functional tumor suppressor gene selected from the group of p53, BRCA1, BRCA2, p14, and p16.

6. The culture according to claim 1, wherein said keratinocytes are esophageal cells which comprise transduced nucleic acids encoding the epidermal growth factor receptor and hTERT.

7. The culture according to claim 1, wherein said keratinocytes are esophageal cells which comprise transduced nucleic acids encoding the epidermal growth factor receptor, hTERT, and an altered p53 protein.

8. The culture according to claim 7, wherein said altered p53 is selected from the group consisting of $p53^{R175H}$, $p53^{V143A}$, $p53^{R248W}$, and $p53^{R273H}$.

9. The culture according to claim 1, wherein said keratinocytes are esophageal cells which comprise transduced nucleic acids encoding the epidermal growth factor receptor, hTERT, and p14.

10. The culture of claim 9, wherein said p14 is $p14^{ARF}$.

11. The culture according to claim 1, wherein said keratinocytes are esophageal cells which comprise transduced nucleic acids encoding the epidermal growth factor receptor, hTERT, and p16.

12. The culture of claim 11, wherein said p16 is $p16^{INK4A}$.

13. The culture according to claim 1, wherein said collagen is selected from the group consisting of human collagen type I, bovine collagen type I, and synthetic collagen, or a combination thereof.

14. The culture according to claim 1, wherein said fibroblasts are selected from the group consisting of adult human fibroblasts, human fetal fibroblasts, and fibroblast stem cells.

15. The culture according to claim 3, wherein said fibroblasts are of esophageal origin.

16. The culture according to claim 1, further comprising human smooth muscle cells embedded into said collagen.

17. The culture according to claim 1, further comprising a layer of endothelial cells underlying said collagen and fibroblast mixture, wherein said endothelial cells form a capillary network induced by fibroblasts in said mixture.

18. The culture according to claim 1, wherein said nucleic acid is introduced into said keratinocytes in a vector.

19. The culture of claim 18, wherein said vector is a viral vector or a plasmid vector.

20. A method of in vitro screening of a compound comprising incubating an organotypic culture of claim 7 in the presence and absence of said compound, and observing the effect of said compound upon the migration and invasive characteristics of said keratinocytes relative to cells which are not incubated with said compound.

21. The method of claim 20, further comprising observing the effect of said compound on cultures which do not contain said transduced nucleic acids.

22. The method according to claim 20, further comprising seeding a malignant cell on an artificial stroma to create a positive control model of tumor formation, tumor invasion or tumor-stroma interaction.

23. The method of claim 20, wherein said method comprises contacting said culture with a cellular migration and invasive process altering agent and assessing the effect of said compound on said culture in the presence of said agent.

24. The method of claim 23, wherein said agent is an MMP-9 inhibitor.

25. The method of claim 23, wherein the agent in an AKT inhibitor.

26. The method of claim 20, further comprising determining whether said compound modulates the expression level of at least one cell adhesion molecule selected from the group of N-cadherin, melanoma cell adhesion molecule, periostin and cadherin11.

27. The method of claim 20, further comprising determining whether said compound modulates the expression level of fibroblast hepatocyte growth factor.

28. The method according to claim 20, wherein said compound is screened for toxicity to human tissue, and wherein said observing step comprises observing the effects of said compound on the morphology and life span of said keratinocytes thereby identifying a compound which reduces the life span of the cells or has a negative impact on the morphology of said cells.

29. A method of in vitro screening of a compound comprising contacting an organotypic culture as claimed in claim 1 comprising cells obtained from a tumor isolated from a human patient with said compound and observing the effect of said compound upon said migration and invasive characteristics of said cells relative to tumor derived organotypic cultures which are not contacted with said compound.

30. The method of claim 29, wherein said method comprises contacting said culture with a cellular migration and invasive process altering agent and assessing the effect of said compound on said culture in the presence of said agent.

31. The culture of claim 14, wherein said human fetal fibroblasts are human fetal skin fibroblasts.

32. The culture of claim 5 or 19, wherein said viral vector is selected from the group consisting of an adenoviral vector, a lentiviral vector, and a retroviral vector and wherein said non functional tumor suppressor gene, if present is a non functional p53 gene.

33. An organotypic culture comprising an artificial stroma including a mixture of collagen and human fibroblasts isolated from a tissue of interest, said stroma being overlayed with primary keratinocytes, said keratinocytes comprising transduced nucleic acids encoding epidermal growth factor receptor and H-tert and a transduced nucleic acid molecule which inhibits p120ctn action, wherein said molecule is selected from the group consisting of small hairpin RNA (shRNA), siRNA, and microRNA, said culture exhibiting enhanced cell migration and invasion in an artificial extracellular matrix relative to control keratinocytes which lack said nucleic acids.

34. The culture according to claim 33, further comprising a non functional p53 tumor suppressor gene and wherein said nucleic acid molecule which inhibits p120ctn action is an shRNA.

35. The culture according to claim 33 or 34, wherein said collagen is selected from the group consisting of human collagen type I, bovine collagen type I, and synthetic collagen, or a combination thereof.

36. The culture according to claim 33 or 34, wherein said fibroblasts are selected from the group consisting of adult human fibroblasts, human fetal fibroblasts, and fibroblast stem cells.

37. The culture according to claim 33 or 34, further comprising human smooth muscle cells embedded into said collagen.

* * * * *